US011225687B2

(12) United States Patent
Ju et al.

(10) Patent No.: US 11,225,687 B2
(45) Date of Patent: Jan. 18, 2022

(54) DNA SEQUENCING BY SYNTHESIS WITH NUCLEOTIDE ANALOGUES AND RAMAN DETECTION

(71) Applicant: THE TRUSTEES OF COLUMBIA UNIVERSITY IN THE CITY OF NEW YORK, New York, NY (US)

(72) Inventors: Jingyue Ju, Englewood Cliffs, NJ (US); Shiv Kumar, Belle Mead, NJ (US); James J. Russo, New York, NY (US); Steffen Jockusch, New York, NY (US); Zengmin Li, Flushing, NY (US); Xiaoxu Li, New York, NY (US); Sergey Kalachikov, Bronx, NY (US); Irina Morozova, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 263 days.

(21) Appl. No.: 16/091,435

(22) PCT Filed: Apr. 4, 2017

(86) PCT No.: PCT/US2017/025850
§ 371 (c)(1),
(2) Date: Oct. 4, 2018

(87) PCT Pub. No.: WO2017/176679
PCT Pub. Date: Oct. 12, 2017

(65) Prior Publication Data
US 2019/0112650 A1  Apr. 18, 2019

Related U.S. Application Data

(60) Provisional application No. 62/317,846, filed on Apr. 4, 2016.

(51) Int. Cl.
*C12Q 1/68* (2018.01)
*C12Q 1/6869* (2018.01)
(Continued)

(52) U.S. Cl.
CPC ............ *C12Q 1/6869* (2013.01); *B82Y 5/00* (2013.01); *B82Y 30/00* (2013.01); *C12N 9/1241* (2013.01);
(Continued)

(58) Field of Classification Search
CPC ...... C12Q 1/68; C12Q 1/6869; C12Q 1/6825; G01N 21/658
See application file for complete search history.

(56) References Cited

U.S. PATENT DOCUMENTS 10,648,026 B2 * 5/2020 Ju .................... C12Q 1/6869
2006/0188901 A1 * 8/2006 Barnes .............. C07H 19/10
435/6.11

(Continued)

FOREIGN PATENT DOCUMENTS

WO  WO-2012083249 A2 * 6/2012 ........... C12Q 1/6869

OTHER PUBLICATIONS

International Search Report dated Aug. 10, 2017 in connection with PCT International Application No. PCT/US2017/025850.
(Continued)

*Primary Examiner* — Jezia Riley
(74) *Attorney, Agent, or Firm* — Gary J. Gershik

(57) ABSTRACT

This invention provides nucleoside polyphosphate analogues each of which comprises a tag comprising a plurality of Raman-scattering moieties; compounds comprising said nucleoside polyphosphate analogs. This invention also provides nucleotide polymerases with one or more attached and/or conjugated noble metal nanoparticles, wherein the noble metal nanoparticles are surface-enhanced Raman
(Continued)

spectroscopy (SERS) substrates thereby creating a region of enhanced sensitivity for surface enhanced Raman spectroscopy (SERS) within or adjacent to the polymerase. This invention also provides a surface with regions of enhanced sensitivity for surface enhanced Raman spectroscopy comprising interspersed rough or nanostructured noble metal surface. This invention also provides methods for determining the sequence of a single stranded DNA or RNA polynucleotide using one or more of nucleoside polyphosphate analogues, polymerase with noble metal nanoparticles, and surface with noble metal.

19 Claims, 29 Drawing Sheets

(51) Int. Cl.
  *C12N 9/12* (2006.01)
  *B82Y 5/00* (2011.01)
  *B82Y 30/00* (2011.01)
  *C12Q 1/6825* (2018.01)
  *G01N 21/65* (2006.01)

(52) U.S. Cl.
  CPC ............ *C12Q 1/68* (2013.01); *C12Q 1/6825* (2013.01); *G01N 21/658* (2013.01); *C12Q 2565/00* (2013.01); *C12Q 2600/106* (2013.01); *C12Y 207/07* (2013.01)

(56) References Cited

U.S. PATENT DOCUMENTS

| | | |
|---|---|---|
| 2011/0097729 A1 | 4/2011 | Densham |
| 2015/0118688 A1 | 4/2015 | Weidemaier et al. |
| 2015/0140561 A1* | 5/2015 | Bergmann ............ C07H 19/10 435/6.11 |
| 2016/0024570 A1* | 1/2016 | Ju ........................ C12Q 1/6874 435/6.11 |

OTHER PUBLICATIONS

Written Opinion of the International Searching Authority dated Aug. 10, 2017 in connection with PCT International Application No. PCT/US2017/025850.
Communication forwarding a Partial Supplementary European Search Report, issued by the European Patent Office dated Feb. 10, 2020, concerning counterpart European Patent Application No. 17779619.0.
Communication forwarding an Extended European Search Report, issued by the European Patent Office dated Jun. 26, 2020, concerning counterpart European Patent Application No. 17779619.0.
Wabuyele et al. (2005) "Hyperspectral surface-enhanced Raman imaging of labeled silver nanoparticles in single cells" Rev. Sci. Instrum. 76:063710-1-7.
Thacker et al. (2014) "DNA origami based assembly of gold nanoparticle dimers for surface-enhance Raman scattering" Nat. Commun. 5:3448-1-7.
Response to Jul. 14, 2020 Communication Pursuant to Rules 70(2) and 70a (2) EPC and dated Jun. 26, 2020 Extended European Search Report filed Jan. 22, 2021 in connection with counterpart European Patent Application No. 17779619.0.

* cited by examiner

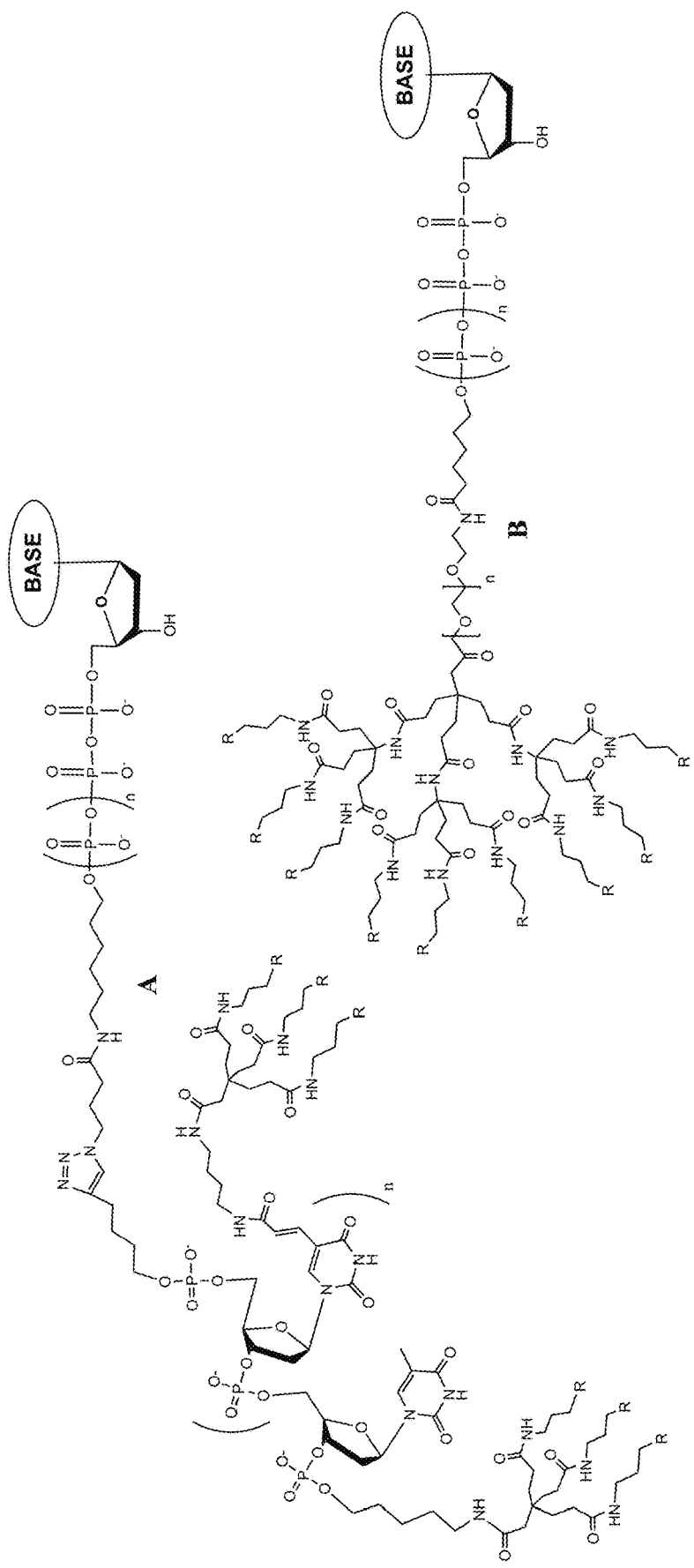

Example of Raman Cluster Tag labeled nucleotides: clusters are attached at terminal phosphate as:
A: Multiple Raman active groups (Raman Tags) are attached on oligonucleotides;
B: Multiple Raman active groups (Raman Tags) are attached on dendrimer BASE: Adenine, Guanine, Thymine, Cytosine, Uracil or derivatives thereof
n = 0-6
R = Raman active groups: $-N_3$, $-C\equiv N$, $-C\equiv CH$, $-C\equiv CD$, $-C\equiv C-CH_3$

Figure 8

Raman Cluster Tag labeled 3'-O reversibly blocked nucleotides in which cluster is attached at the terminal phosphate (A) or attached via cleavable linker to base (B)

BASE: Adenine, Guanine, Thymine, Cytosine, Uracil or derivatives thereof
n = 0-6

R' and Cleavable linker = Allyl (-CH$_2$-CH=CH$_2$), MOM (-CH$_2$OCH$_3$), AZM (-CH$_2$N$_3$), -CH$_2$S-S-alkyl and 2-Nitrobenzyl Example of 3'-O blocked nucleotides labled with Raman Cluster Tags at the terminal phosphate.

BASE: Adenine, Guanine, Thymine, Cytosine, Uracil or derivatives thereof
n = 0-6
R = Raman active groups: $-N_3$, $-C\equiv N$, $-C\equiv CH$, $-C\equiv CD$, $-C\equiv C-CH_3$
    MOM ($-CH_2OCH_3$), AZM ($-CH_2N_3$),
R' = Allyl ($-CH_2-CH=CH_2$), $-CH_2S$-S-alkyl and 2-Nitrobenzyl

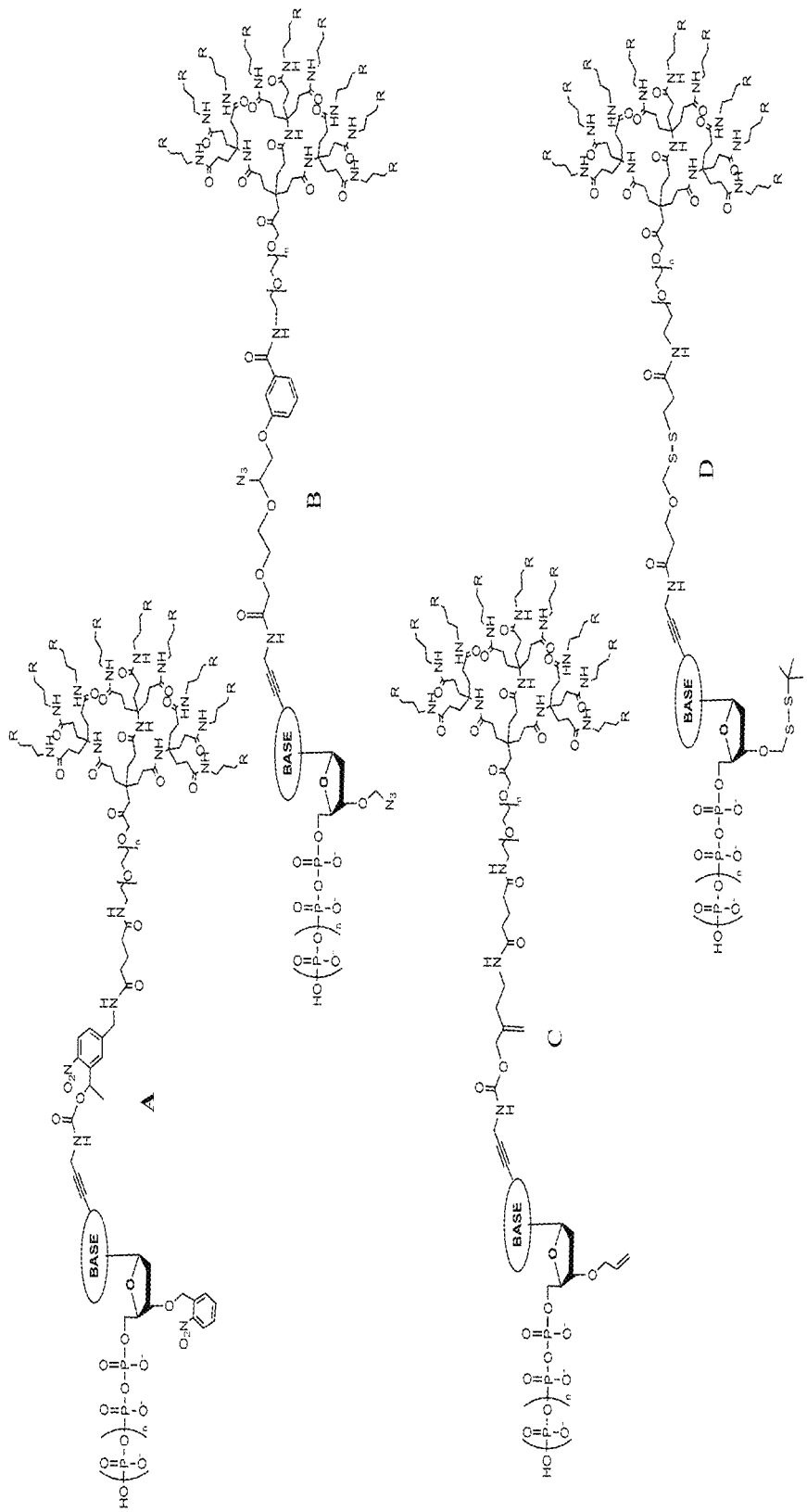

Figure 13

Example of Raman Cluster Tag labeled nucleotides in which clusters are attached at the base via cleavable linker and 3'-O are reversibly blocked using allyl, AZM (azido methyl) ,2-nitrobenzyl and alkyl disulfide methyl blocking groups. The dendrimer Raman cluster is shown as example.
A, Raman cluster tag is attached with 2-nitrobenzyl linker; B, Raman cluster tag is attached with azido methyl linker;
C, Raman cluster tag is attached with allyl linker and D, Raman cluster tag is attached with disulfide methyl linker.
BASE: Adenine, Guanine, Thymine, Cytosine, Uracil or derivatives thereof
n = 0-6
R = Raman active groups: -N₃, -C≡N, -C≡CH, -C≡CD, -C≡C-CH₃

Example of Raman Cluster Tag labeled nucleotides: clusters are attached at base.

BASE: Adenine, Guanine, Thymine, Cytosine, Uracil or derivatives thereof
n = 0-6
R: Raman active groups : $-N_3, -C{\equiv}N, -C{\equiv}CH, -C{\equiv}CD, -C{\equiv}C-CH_3$ Example of Raman Cluster Tag labeled nucleotides in which clusters are attached at both terminal phosphate and base (Dendrimer clusters are shown as example)

BASE: Adenine, Guanine, Thymine, Cytosine, Uracil or derivatives thereof
n = 0-6
R: Raman active groups: $-N_3$, $-C\equiv N$, $-C\equiv CH$, $-C\equiv CD$, $-C\equiv C-CH_3$ Raman Cluster Tag labeled nucleotides in which clusters are attached via cleavable linker to base (A) or clusters are attached at both terminal phosphate and base via cleavable linker without blocking the 3'- position (B)

BASE: Adenine, Guanine, Thymine, Cytosine, Uracil or derivatives thereof
n = 0-6

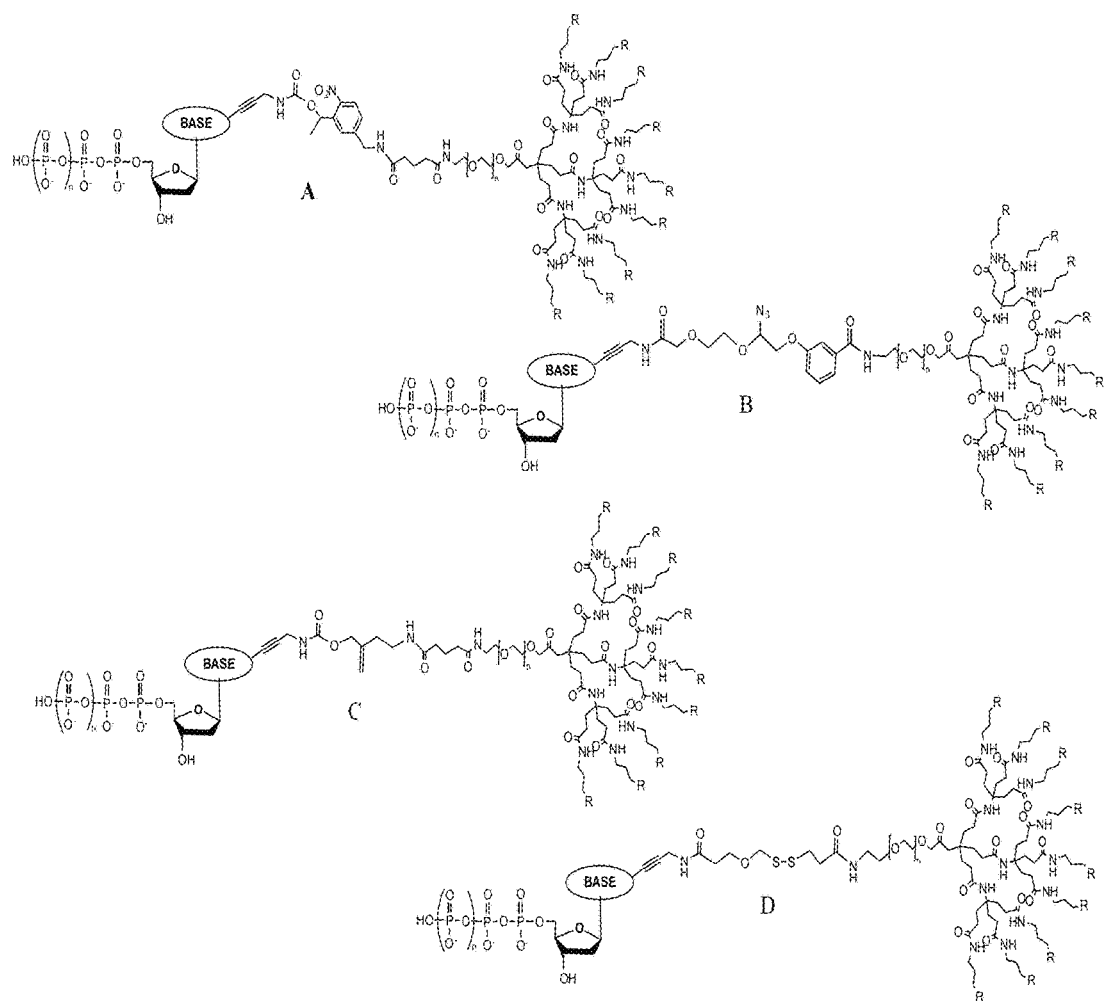

Example of Raman Cluster Tag labeled nucleotides in which clusters are attached at the base via cleavable linker without blocking at 3' position. The dendrimer Raman cluster is shown as example.
A, Raman cluster tag is attached with 2-nitrobenzyl linker; B, Raman cluster tag is attached with azido methyl linker;
C, Raman cluster tag is attached with allyl linker and D, Raman cluster tag is attached with disulfide methyl linker.
BASE: Adenine, Guanine, Thymine, Cytosine, Uracil or derivatives thereof
n = 0-6
R = Raman active groups: $-N_3$, $-C\equiv N$, $-C\equiv CH$, $-C\equiv CD$, $-C\equiv C-CH_3$

Figure 18

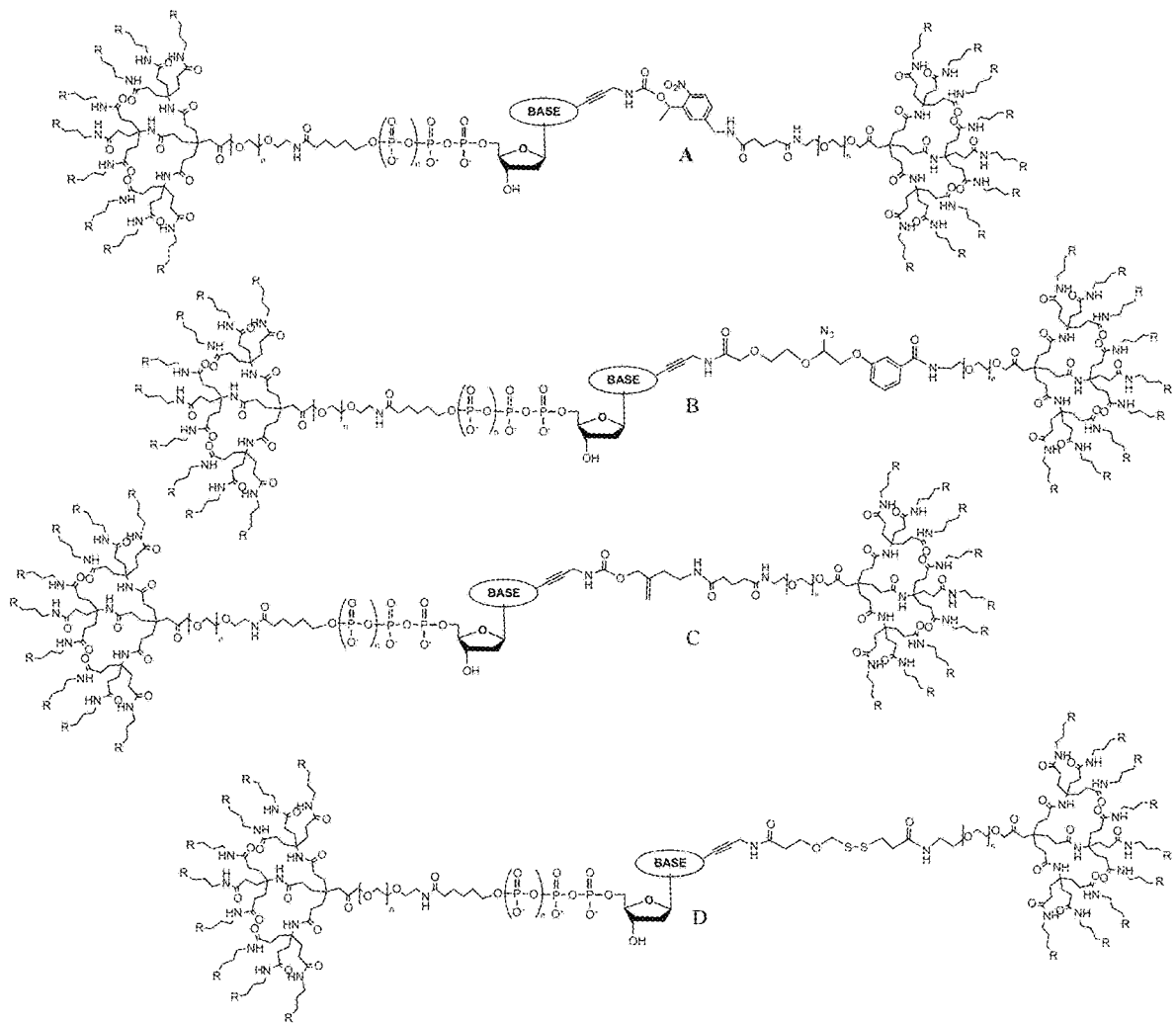

Example of Raman Cluster Tag labeled nucleotides in which clusters are attached at both terminal phosphate and base via cleavable linker without blocking of 3' position. The dendrimer Raman cluster is shown as example.
A, Raman cluster tag is attached with 2-nitrobenzyl linker; B, Raman cluster tag is attached with azido methyl linker;
C, Raman cluster tag is attached with allyl linker and D, Raman cluster tag is attached with disulfide methyl linker.
BASE: Adenine, Guanine, Thymine, Cytosine, Uracil or derivatives thereof
n = 0-6
R = Raman active groups: $-N_3$, $-C\equiv N$, $-C\equiv CH$, $-C\equiv CD$, $-C\equiv C-CH_3$

Figure 19

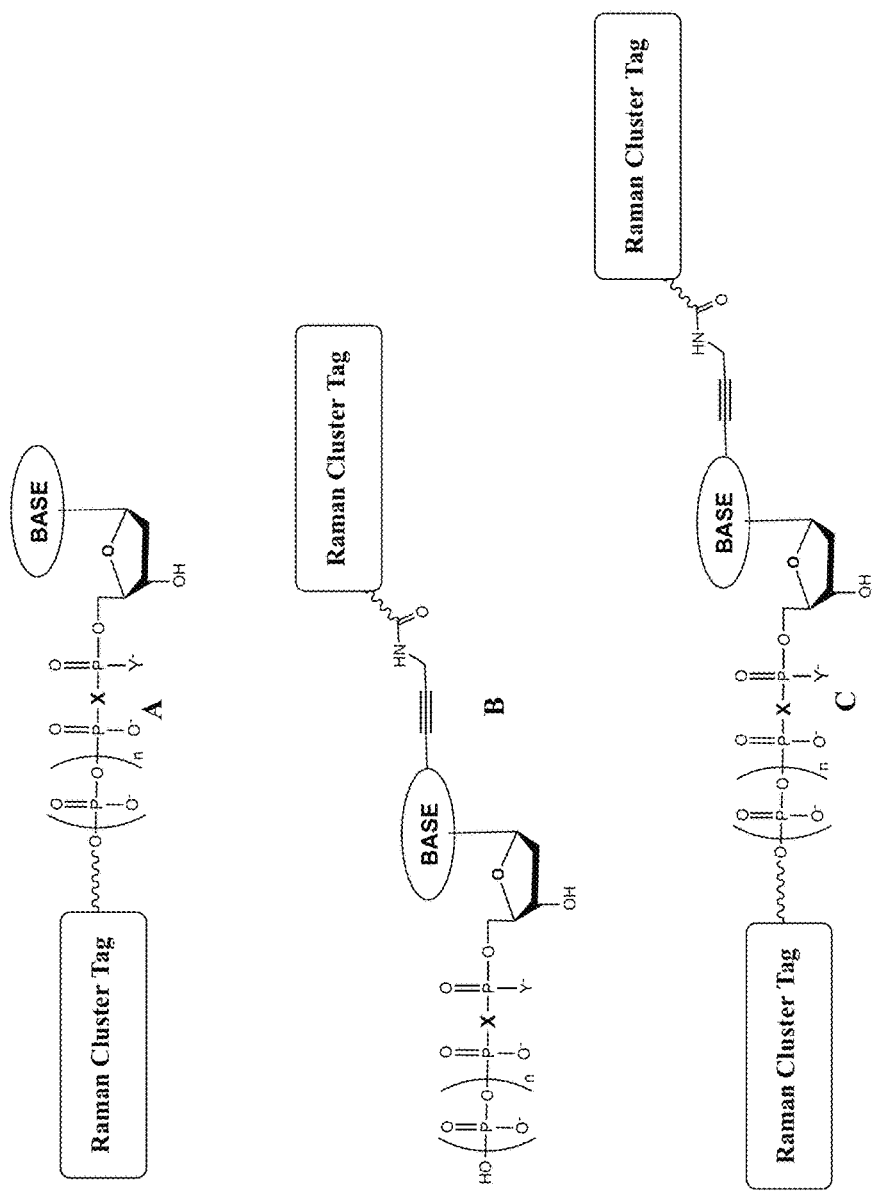

Raman Cluster Tag labled non-incorporable nucleotide derivatives for SERS. A: Raman cluster tag is attached at the terminal phosphate; B: Raman cluster tag is attached at the base; C: Raman cluster tags are attached at both terminal phosphate and base.
X = $CH_2$, NH, $CHF-$, $CF_2$
Y = O, S, $BH_3$
BASE = Adenine, Guanine, Thymine, Cytosine, Uracil or derivatives thereof
n = 0-6
Raman Cluster Tag = Chemical structures containing multiple Raman active groups, such as: $-N_3$, $-C\equiv N$, $-C\equiv CH$, $-C\equiv CD$, $-C\equiv C-CH_3$

Figure 20

Example of Raman Cluster Tag labeled unincorporable nucleotides: clusters are attached at terminal phosphate.

BASE: Adenine, Guanine, Thymine, Cytosine, Uracil or derivatives thereof
n = 0-6
R: Raman active groups : $-N_3$, $-C\equiv N$, $-C\equiv CH$, $-C\equiv CD$, $-C\equiv C-CH_3$
X = $CH_2$, NH, CHF, $CF_2$
Y = O, S, $BH_3$ Example of Raman Cluster Tag labeled unincorporable nucleotides: clusters are attached at base.

BASE: Adenine, Guanine, Thymine, Cytosine, Uracil or derivatives thereof
n = 0-6
R: Raman active groups: $-N_3$, $-C\equiv N$, $-C\equiv CH$, $-C\equiv CD$, $-C\equiv C-CH_3$
X = $CH_2$, NH, CHF, $CF_2$
Y = O, S, $BH_3$ Example of Raman Cluster Tag labeled unincorporable nucleotides in which clusters are attached at both terminal phosphate and base (Dendrimer clusters are shown as example)

BASE: Adenine, Guanine, Thymine, Cytosine, Uracil or derivatives thereof
n = 0-6
R: Raman active groups: $-N_3$, $-C\equiv N$, $-C\equiv CH$, $-C\equiv CD$, $-C\equiv C-CH_3$
X = $CH_2$, NH, CHF, $CF_2$
Y = O, S, $BH_3$

DNA SEQUENCING BY SYNTHESIS WITH NUCLEOTIDE ANALOGUES AND RAMAN DETECTION

CROSS-REFERENCE TO RELATED APPLICATIONS

This application is a § 371 national stage of PCT International Application PCT/US2017/025850, filed Apr. 4, 2017, claiming the benefit of U.S. Provisional Application No. 62/317,846, filed Apr. 4, 2016, the contents of each of which are hereby incorporated by reference into the application.

Throughout this application, certain publications are referenced, by authors and publication year. Full citations for these publications may be found immediately preceding the claims. The disclosures of these publications in their entireties are hereby incorporated by reference into this application in order to describe more fully the state of the art to which this invention relates.

BACKGROUND OF THE INVENTION

High throughput DNA sequencing is essential to a broad array of genomic studies, such as whole genome and meta-genome sequencing, expression profiling of mRNAs and miRNAs, discovery of alternatively spliced and polyadenylated transcripts, histone and chromatin changes involved in epigenetic events, and identification of binding sites for transcription factors and RNA binding proteins. Sequencing of individual human genomes is especially appealing, with its potentially unlimited but as yet unachieved promise for personalized medicine.

Given the ever-growing importance of high throughput DNA sequencing for biological and anthropological research, agriculture and medicine, there is a need for sequencing technologies that are low-cost and rapid on the one hand, and have high sensitivity and accuracy on the other. Sequencing by Synthesis (SBS) has driven much of the "next generation" sequencing technology, allowing the field to approach the $100,000 Genome [Fuller et al. 2009, Hawkins et al. 2010, Morozova et al. 2009, and Park 2009]. With further improvements in nucleotide incorporation detection methods, SBS could be an engine that drives third-generation platforms leading to the reality of the "$1,000 Genome". At the same time, since non-fluorescent detection approaches are likely to decrease the cost of obtaining data by avoiding expensive cameras and imaging tools, SBS also offers the possibility of high sensitivity, leading to both longer reads and permitting single molecule sequencing, thereby removing one of the most time-consuming and biased steps—the generation and amplification of DNA templates.

Current commercial next-generation sequencing platforms have certainly made substantial inroads in this direction, with the current cost of sequencing a human genome at high draft coverage significantly below $10,000 [Fuller et al. 2009, Hawkins et al. 2010, Morozova et al. 2009, and Metzker 2010]. Expression studies (e.g. using RNA-Seq) and epigenetic studies (e.g. using Methyl-Seq, ChIP-Seq), among many others, have also benefited greatly from these platforms [Ozsolak et al. 2011, Varley et al. 2010, and Park 2009]. Nonetheless, these costs are still prohibitive for most laboratories and for clinical applications.

All of the current approaches have one or more additional limitations: biased coverage of GC-rich or AT-rich portions of genomes; inability to accurately sequence through homopolymer stretches; inability to directly sequence RNA; high reagent costs; difficulty in sequencing beyond 200 or so nucleotides resulting in difficulty in de novo assembly of previously unsequenced genomes; insufficient throughput due to ceiling on number of possible reads per run.

To overcome these obstacles, a number of third-generation sequencing platforms have appeared on the market, or are in development. All of these have issues with accuracy and most have limited throughput. For example, attempts to sequence DNA using Raman detection have been reported [Kneipp et al. 1998] but thus far have been unsuccessful.

In addition to high throughput DNA sequencing, detection of protein-protein interactions are essential for study of cell biology. Examples of protein-protein interactions include generation of protein assemblies for enzymatic reactions in metabolic pathways (e.g., fatty acid synthesis), ribosomes (protein synthesis), ubiquitin association with proteins destined to be degraded, for transport of ions (multi-subunit membrane channels and pumps), for enhancing or inhibiting transcription of genes (cooperating transcription factors), formation of cellular junctions and cell-cell interactions, and countless other examples. Mutations in these proteins affecting their assembly or interactions are crucial for a number of diseases, and particularly relevant to the development of tumors.

Numerous assays have been developed for detection of specific protein-protein interactions. Biochemical approaches include gel shift assays, cross-linking assays, immunoprecipitation, immunoblotting, etc. The yeast two-hybrid and three-hybrid systems are genetic approaches that have been developed to identify target proteins that can bind to a bait protein molecule. Several of these methods characterize the partners and the complexes by gel electrophoresis with at least one of the partners radiolabeled. Other assays including surface binding assays, for example protein arrays, may use fluorescent tags. Finally, it is possible to reveal the interacting proteins by mass spectrometry.

Recently, use of Raman spectroscopy for molecular detection has been considered. As described in prior patent applications (Ju et al 2015, 2016), Raman spectroscopy, which is based on the inelastic scattering of light, has the ability to distinguish a set of nucleotide tags due to their ability to produce Raman shifts in the spectral region, 2100-2300 $cm^{-1}$, where proteins, nucleic acids, amino acids and nucleotides do not produce any Raman signals. Moreover, these small chemical groups produce very sharp peaks in the Raman spectrum compared to much broader peaks in the visible spectrum associated with bulky fluorescent tags, making it possible to select sets of 4 or more tags for labeling the different nucleotides. On the other hand, spontaneous Raman signals are substantially weaker than fluorescent signals.

However, it has been shown that the Raman signals can be enhanced dramatically, by as much as 11 orders of magnitude (Le Ru et al 2007), by taking advantage of localizing the Raman active molecules within 10 nm of rough or nanostructured noble metal surfaces, an effect thought to be due to the excitement of localized surface plasmons. The phenomenon is referred to as surface-enhanced Raman spectroscopy (SERS). Though several metals can be used to achieve this effect, the most common SERS substrates are made with gold or silver nanoparticles. Accordingly, herein described are molecular tags utilizing a variety of chemical groups, which have been verified in that they produce discrete signals in the aforementioned Raman spectral window surrounding 2200 $cm^{-1}$.

Moreover, 4-step DNA sequencing with Raman detection on a SERS surface has been demonstrated using four nucleotide analogues with a 3'-O-azidomethyl group (Palla et al 2014). The novel invention disclosed herein combines the advantages of sequencing by synthesis (SBS) in terms of sequencing accuracy and the power of SERS in a number of approaches for nucleic acid sequencing with both ensembles of identical template molecules and single template molecules. Further disclosed methods for real-time single molecule sequencing by synthesis that use these same principles.

SUMMARY OF THE INVENTION

This invention provides a nucleotide polymerase with one or more attached and/or conjugated noble metal nanoparticles, wherein the noble metal nanoparticles are surface-enhanced Raman spectroscopy (SERS) substrates thereby creating a region of enhanced sensitivity for surface enhanced Raman spectroscopy (SERS) within or adjacent to the polymerase.

This invention also provides a compound having the structure:

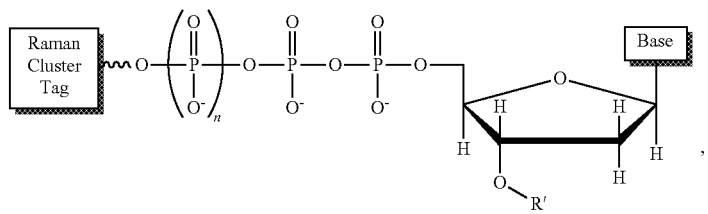

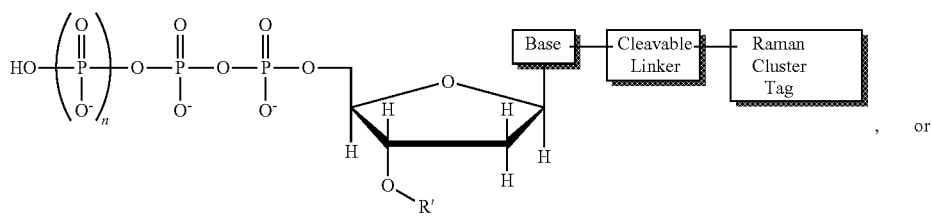

, or

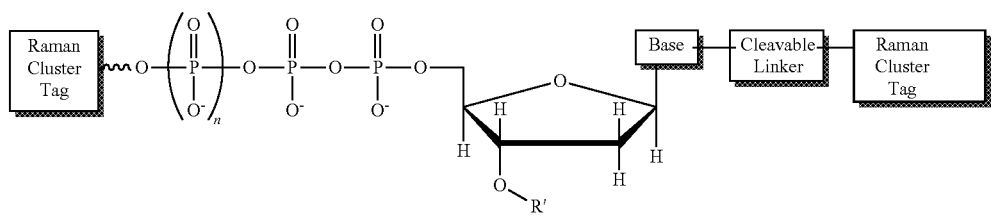

wherein the base is A, G, T, C, or U, or derivatives thereof, wherein n=0, 1, 2, 3, 4, 5, or 6, wherein R' is H, a reversible 3'-0 blocking moiety that prevents a subsequent nucleotide polymerase event, and/or a Raman cluster tag, wherein the Raman cluster tag(s) comprise one or more Raman active groups.

This invention also provides a compound having the structure:

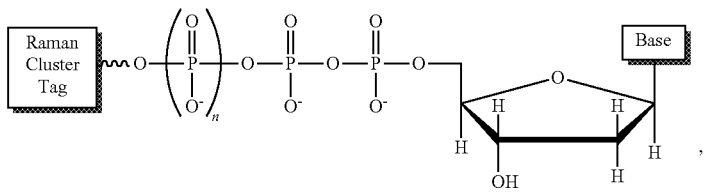

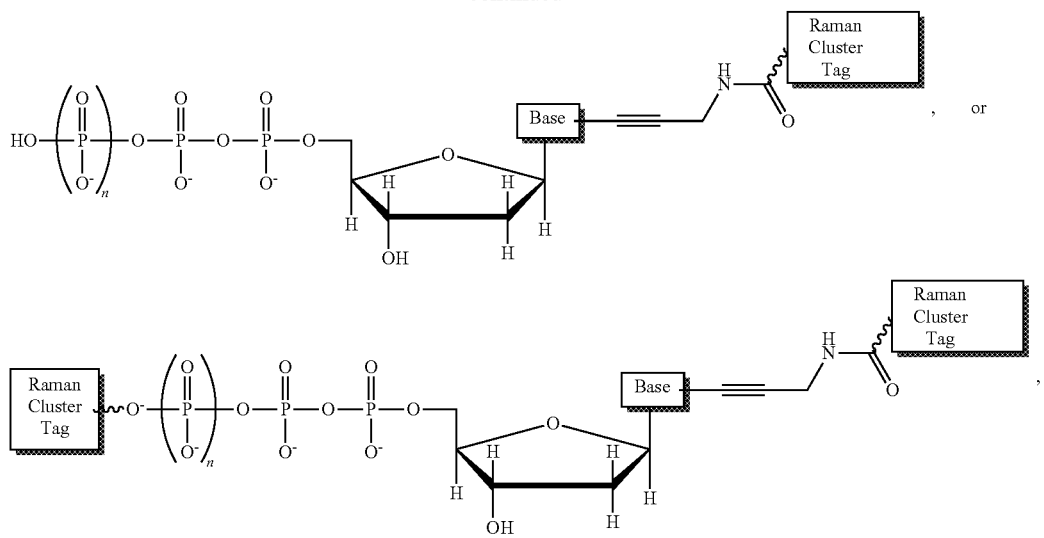

wherein base is any one of A, G, T, C, or U, or derivatives thereof, wherein n=0, 1, 2, 3, 4, 5, or 6, and wherein the Raman Cluster Tag is a chemical structure comprising one or more Raman active groups.

This invention also provides a compound that have the structure:

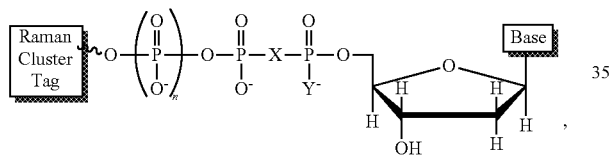

wherein base is any one of A, G, T, C, or U, or derivatives thereof, wherein n=0, 1, 2, 3, 4, 5, or 6, wherein the Raman Cluster Tag comprises Raman active groups, wherein X is any one of $CH_2$, NH, CHF—, or $CF_2$, and wherein Y is any one of O, S, or $BH_3$, wherein X and/or Y prevent the nucleotide polymerase from cleaving the bond between the α and β phosphates.

This invention also provides a method for sequencing a polynucleotide sequence, comprising:
  a) contacting an nucleotide sequence having a primer hybridized to a portion thereof, with a nucleotide polymerase and nucleoside polyphosphate analogues:
    (i) under conditions that permit the nucleotide polymerase to catalyze incorporation onto the primer of a nucleoside polyphosphate analogue if the analogue is complementary to a nucleotide residue of oligonucleotide sequence which is immediately 5' to a nucleotide residue of the nucleotide sequence hybridized to the 3' terminal nucleotide of the primer, so as to form a DNA extension product, or
    (ii) further contacting with one or more non-catalytic metal ions under conditions permitting the nucleotide polymerase to form a ternary complex with the single-stranded DNA, primer, and the nucleoside polyphosphate analogue if the analogue is complementary to a nucleotide residue of the single-stranded DNA which is immediately 5' to a nucleotide residue of the single-stranded DNA hybridized to the 3' terminal nucleotide of the primer, wherein one or more of the polymerase, single-stranded DNA, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

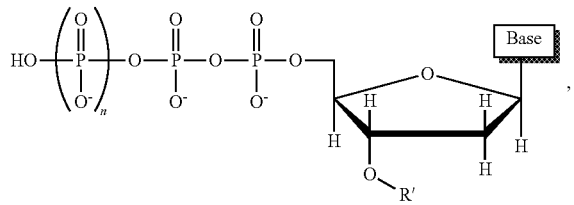

wherein base is any one of A, G, T, C, or U, or derivatives thereof, wherein n=0, 1, 2, 3, 4, 5, or 6, and R' comprises H, a 3'-O blocking group, a cleavable linker and/or a Raman cluster tag, and optionally wherein the analogue has a Raman cluster tag attached to the base, wherein said Raman cluster attached to the base is optionally attached via a cleavable linker, and wherein optionally a Raman cluster tag is attached to the terminal phosphate of the analogue, and wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein each analogue comprises a base which is different from the base of each of the remaining three analogues, and wherein when the cleavable linker is cleaved it results in a 3'-OH, b) determining the wavenumber of the Raman spectroscopy peak of the incorporated nucleoside polyphosphate analogue Raman cluster tag, so as to thereby determine the identity of the incorporated nucleoside polyphosphate analogue and the identity of the complementary nucleotide residue in the single-stranded DNA;

c) wherein R' or a linker attaching a base to a Raman cluster tag contain cleavable linkers, cleaving the linkers;

d) wherein the base contains a terminal phosphate bound Raman cluster tag, adding catalytic metal ions, thereby allowing the polymerase to catalyze incorporation of the analogue while also cleaving the terminal phosphate with the bound Raman cluster tag, or optionally adding nucleotide reversible terminators to replace the analogue in the ternary complex, and subsequently adding a catalytic metal ion so as to permit the polymerase to incorporate the nucleotide reversible terminator;

e) iteratively performing steps a) through d) for each nucleotide residue of the nucleotide sequence to be sequenced so as to thereby determine the sequence of the nucleotide sequence.

This invention also comprises a method for sequencing a polynucleotide sequence, comprising:

a) contacting the nucleotide sequence having a primer hybridized to a portion thereof, with a nucleotide polymerase, four nucleoside polyphosphate analogues, under conditions permitting the nucleotide polymerase to form a ternary complex with the single-stranded DNA, primer, and the nucleoside polyphosphate analogue if the analogue is complementary to a nucleotide residue of the single-stranded DNA which is immediately 5' to a nucleotide residue of the single-stranded DNA hybridized to the 3' terminal nucleotide of the primer, wherein one or more of the polymerase, single-stranded DNA, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

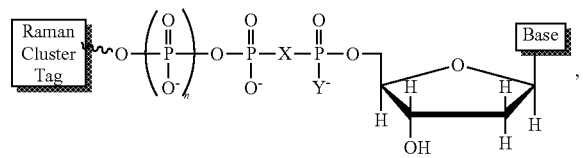

wherein base is any one of A, G, T, C, or U, or derivatives thereof, wherein n=0, 1, 2, 3, 4, 5, or 6, wherein the Raman Cluster Tag comprises Raman active groups, wherein X is any one of $CH_2$, NH, CHF—, or $CF_2$, and wherein Y is any one of O, S, or $BH_3$, wherein X and/or Y prevent the nucleotide polymerase from cleaving the bond between the α and β phosphate, wherein the Raman spectroscopy peaks of the Raman cluster tag are predetermined, wherein the Raman spectroscopy peaks of the tag on each analogue are distinguishable from the Raman spectroscopy peaks of the tags on each of the remaining analogues, wherein each analogue comprises a base which is different from the base of each of the remaining three analogues;

b) determining the wavenumber of the Raman spectroscopy peaks of the Raman cluster tag of the analogue in the ternary complex, so as to thereby determine the identity of the nucleoside polyphosphate and the identity of the complementary nucleotide residue in the nucleotide sequence;

c) contacting the ternary complex with four nucleotide reversible terminators thereby replacing the nucleoside polyphosphate analogue with a nucleotide reversible terminator with the proviso that the nucleotide reversible terminator is complementary to a nucleotide residue of the single-stranded DNA which is immediately 5' to a nucleotide residue of the single-stranded DNA hybridized to the 3' terminal nucleotide of the primer, wherein each nucleotide reversible terminator has the structure:

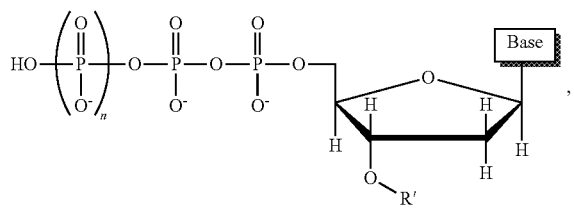

wherein base is any one of A, G, T, C, or U, or derivatives thereof, wherein n=0, 1, 2, 3, 4, 5, or 6, wherein R' comprises a cleavable 3' blocking group, wherein each nucleotide reversible terminator comprises a base which is different from the base of each of the remaining nucleotide reversible terminators;

d) removing some or all of the non-catalytic metal ions, and adding catalytic metal ions, thereby permitting the nucleotide polymerase to incorporate the nucleotide reversible terminator into the primer so as to form a nucleotide extension product;

e) cleaving the blocking group thereby resulting in a 3'-OH;

f) iteratively performing steps a) through e) for each nucleotide residue of the single-stranded DNA to be sequenced so as to thereby determine the sequence of the nucleotide sequence.

This invention also provides a method for sequencing an nucleotide sequence, comprising:

a) contacting an nucleotide sequence having a primer hybridized to a portion thereof, with a nucleotide polymerase and nucleoside polyphosphate analogues:
(i) under conditions that permit the nucleotide polymerase to catalyze incorporation onto the primer of a nucleoside polyphosphate if the analogue is complementary to a nucleotide residue of oligonucleotide sequence which is immediately 5' to a nucleotide residue of the nucleotide sequence hybridized to the 3' terminal nucleotide of the primer, so as to form a DNA extension product, or
(ii) further contacting with or more non-catalytic metal ions under conditions permitting the nucleotide polymerase to form a ternary complex with the single-stranded DNA, primer, and the nucleoside polyphosphate analogue if the analogue is complementary to a nucleotide residue of the single-stranded DNA which is immediately 5' to a nucleotide residue of the single-stranded DNA hybridized to the 3' terminal nucleotide of the primer, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

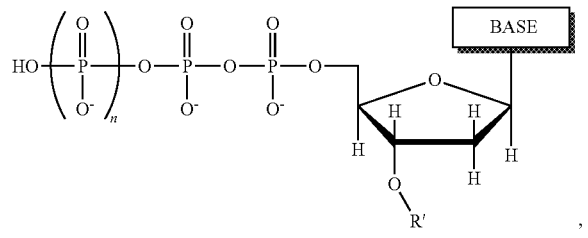

wherein base is any one of A, G, T, C, or U, or derivatives thereof, wherein n=0, 1, 2, 3, 4, 5, or 6, and R' comprises H, a 3'-O blocking group, a cleavable linker and/or a Raman cluster tag, and optionally wherein the analogue has a Raman cluster tag attached to the base, wherein said Raman cluster attached to the base is optionally attached via a cleavable linker, and wherein optionally a Raman cluster tag is attached to the terminal phosphate of the analogue, and wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein each analogue comprises a base which is different from the base of each of the remaining three analogues, and wherein when the cleavable linker is cleaved it results in a 3'-OH;

b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded DNA;

c) wherein R' or a linker attaching a base to a Raman cluster tag contain cleavable linkers, cleaving the linkers;

d) wherein the base contains a terminal phosphate bound Raman cluster tag, adding catalytic metal ions, thereby allowing the polymerase to catalyze incorporation of the analogue while also cleaving the terminal phosphate with the bound Raman cluster tag, or optionally adding nucleotide reversible terminators to replace the analogue in the ternary complex, and subsequently adding a catalytic metal ion so as to permit the polymerase to incorporate the nucleotide reversible terminator;

e) iteratively performing steps a) through d) for each nucleotide residue of the nucleotide sequence to be sequenced so as to thereby determine the sequence of the nucleotide sequence.

BRIEF DESCRIPTION OF THE FIGURES

FIG. 8: Example Raman cluster (RC) labeled nucleotides in which RC is attached at the terminal phosphate. Multiple Raman active groups can be either linked to an oligonucleotide (A) or linked to a dendrimer (B). The method of synthesizing the dendrimer shown in (B) is presented in FIG. 9.

FIG. 13: Example Raman cluster (RC) labeled 3'-O reversibly blocked nucleotides. RC is attached to base via a variety of cleavable linkers.

FIG. 18: Example Raman cluster (RC) labeled nucleotides. RC is attached to base via a variety of cleavable linkers.

FIG. 19: Example Raman cluster (RC) labeled nucleotides. RC is attached to base via a variety of cleavable linkers and also attached to the terminal phosphate.

FIG. 20: Raman cluster (RC) labeled non-incorporable nucleotides. RC is attached to the terminal phosphate (A), to base (B) or to both the terminal phosphate and base (C).

DETAILED DESCRIPTION OF THE INVENTION

Figure 1:
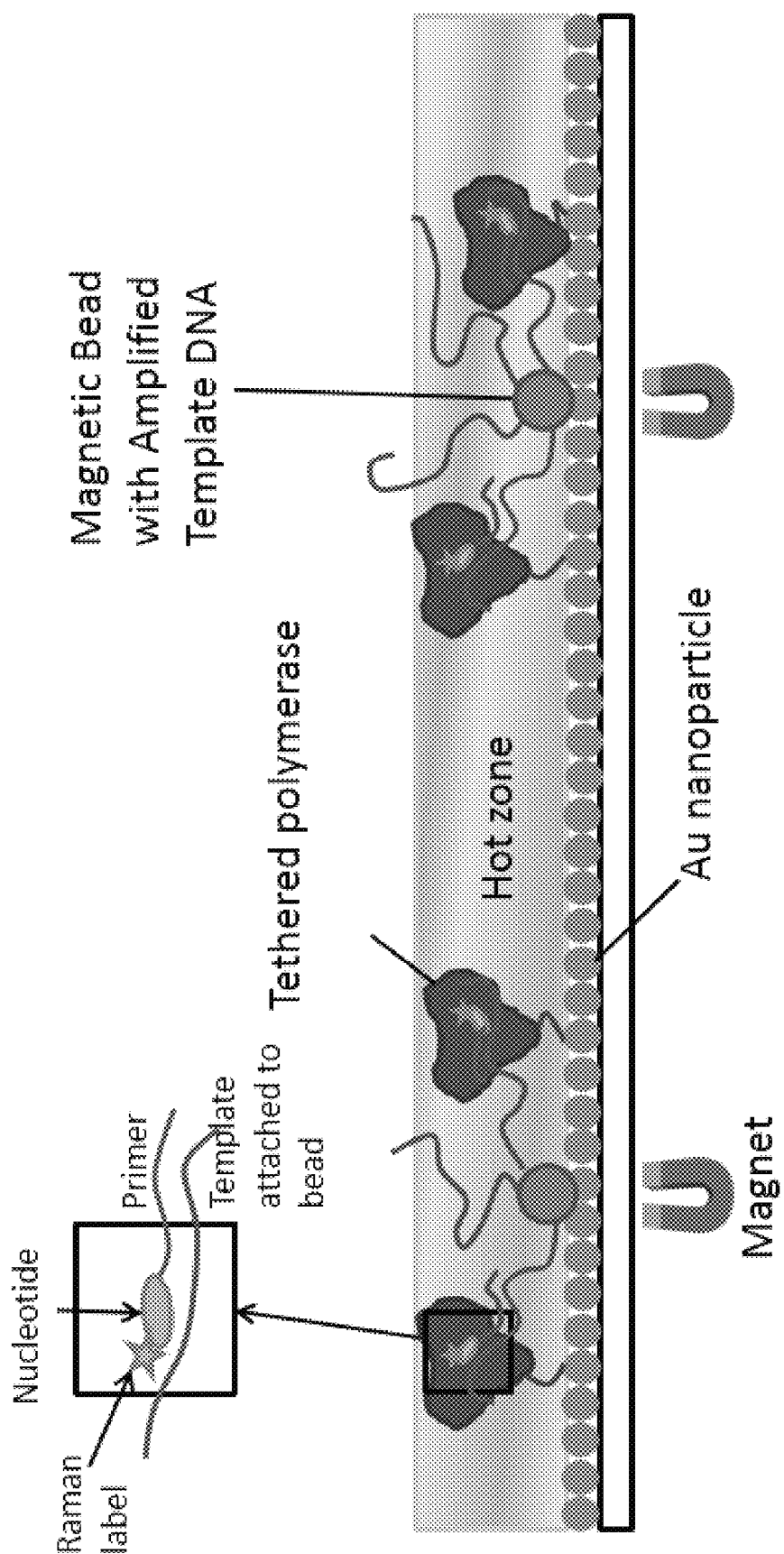
FIG. 1: Schematic of set-up for ensemble SBS on SERS substrate with template amplified on beads attached to surface. Gold nanoparticles are distributed on a glass slide. DNA is amplified on magnetic beads by emulsion PCR or equivalent approach and attracted to the gold surface by a magnetic field. The surface is derivatized with a large excess of tethered polymerases. This keeps the enzyme's active site within the SERS hot zone. The use of the magnetic beads permits washing and maintains the reactions in a particular location for multiple sequencing cycles. The solution contains primer and nucleotides bearing single Raman active groups (RAGs) or RAG clusters. After the first template complementary nucleotide is bound in the ternary complex where it is held either by the use of non-catalytic metals, unincorporable nucleotides, reversible terminators, or combinations of these, see Examples 1-10), the Raman signal is detected, and the block to incorporation of the current or subsequent nucleotide is removed, the next round is initiated.

This invention provides a nucleotide polymerase having 1 or more attached and/or conjugated noble metal nanoparticles, wherein the noble metal nanoparticles are a surface-enhanced Raman spectroscopy (SERS) substrates. In another embodiment the noble metal nanoparticles are either gold or silver nanoparticles. In another embodiment the metal nanoparticles are between 3 nm and 10 nm. In another embodiment there are 2, 3, 4, or 5 metal nanoparticles. In another embodiment the metal nanoparticles are attached and/or conjugated to the polymerase 1 nm-3 nm from the active site of the polymerase. In another embodiment the metal nanoparticles are attached and/or conjugated to the polymerase 1 nm-3 nm from the active site of the polymerase, thereby creating a region of enhanced sensitivity for surface enhanced Raman spectroscopy (SERS) at the active site. In another embodiment the metal nanoparticles are attached and/or conjugated to the polymerase such that when a nucleoside and/or nucleotide are in the active site of the polymerase, and wherein the nucleoside and/or nucleotide are tagged with a Raman active molecule, the metal nanoparticles are located 1 nm-3 nm from the Raman active molecule. In another embodiment wherein the attached and/or conjugated metal nanoparticles create a region of enhanced sensitivity for surface enhanced Raman spectroscopy (SERS) at the location of the Raman active molecule.

This invention also provide for a compound having the structure:

wherein the base is A, G, T, C, or U, or derivatives thereof, wherein n=0, 1, 2, 3, 4, 5, or 6, wherein R' is a reversible blocking moiety that prevents a 3' hydroxyl group and thereby prevents a nucleotide polymerase from incorporating the nucleoside polyphosphate analogue into a polynucleotide strand.

In another embodiment the cleavable linker and reversible blocking moiety independently comprise any one of an allyl, alkyl, carbonyl, Sieber linkers, indole, disulfide, dithiomethyl, azidomethyl, nitrobenzyl, or any derivative thereof. In another embodiment R' comprises a Raman cluster tag. In another embodiment the Raman cluster tag is one or more of $-N{=}N^{+}{=}N^{-}$, $-C{\equiv}CH$, $-C{\equiv}CD$, $-C{\equiv}C-$ alkyl, $-C{\equiv}C$-aryl and $-C{\equiv}N$ moieties. In another embodiment the Raman cluster tag and/or tags has a Raman spectroscopy peak with a wave number from 2100 cm$^{-1}$ to 2300 cm$^{-1}$. In another embodiment the reversible blocking moiety may be cleaved, and thereby result in a 3'-OH. In another embodiment the reversible blocking moiety is photo cleavable or chemically cleavable. In another embodiment the reversible blocking moiety is cleavable with one or more of Pd(0), tetrabutylammonium, DTT, a triphosphine, peroxydisulphate, iodine, or any derivative thereof.

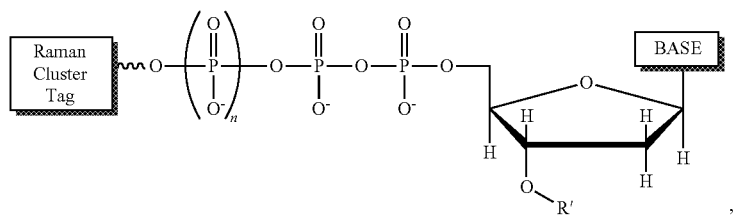

,

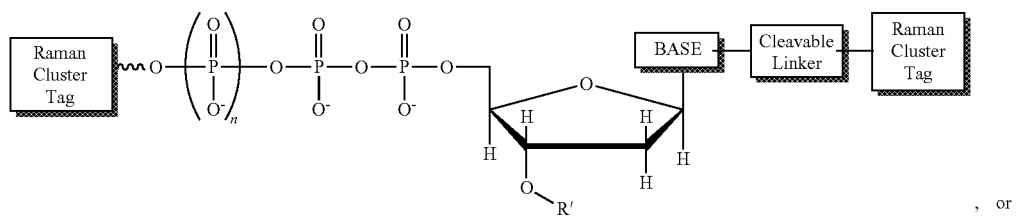

, or

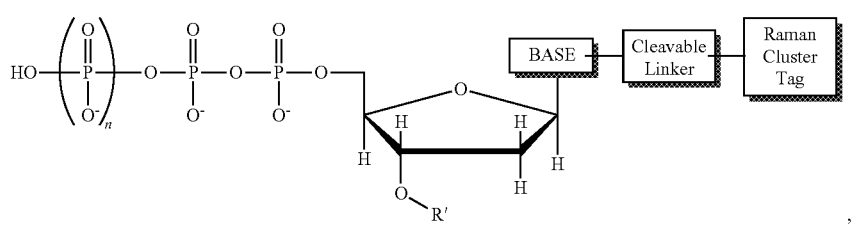

,

In another embodiment the compound has the structure:
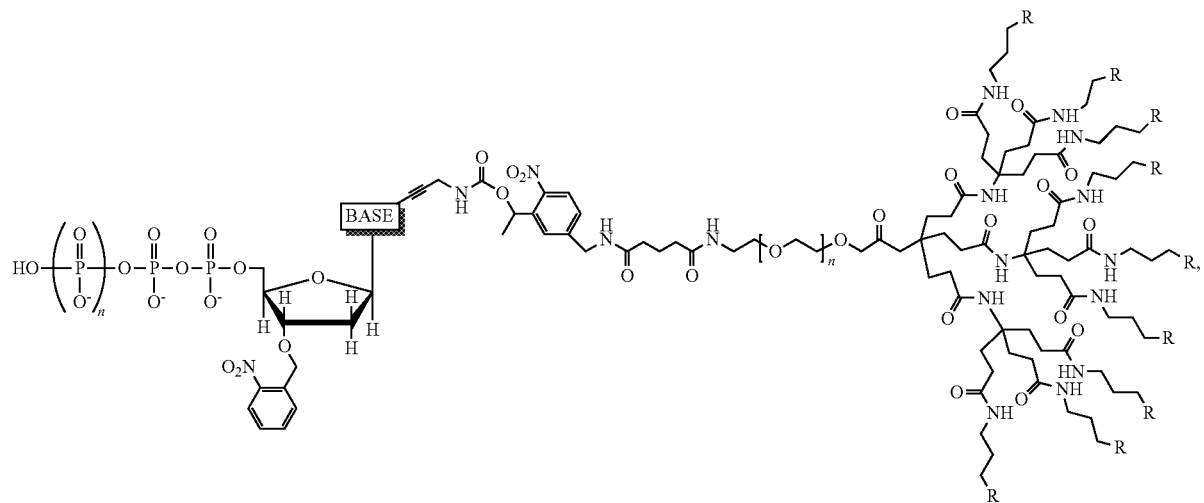
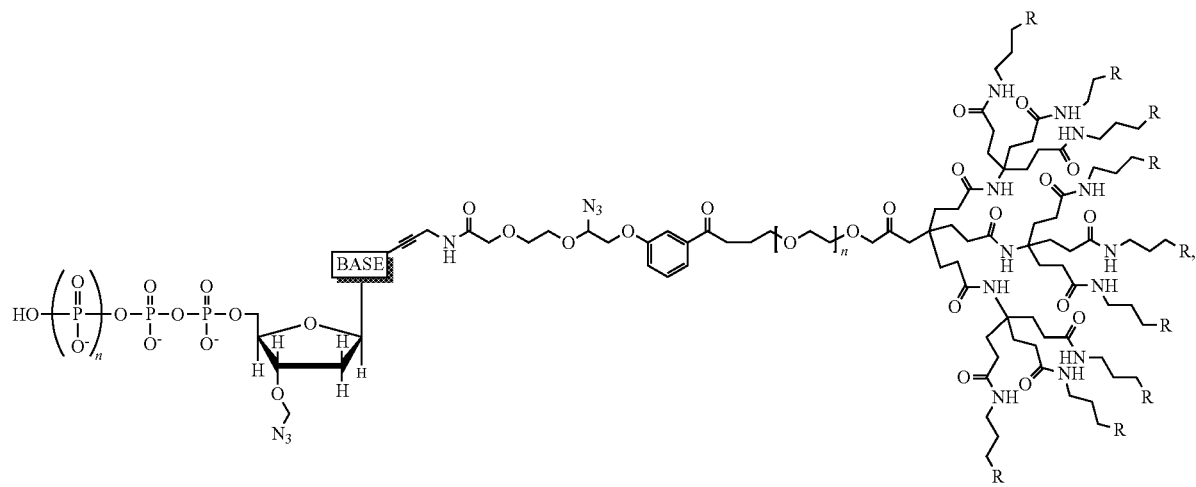
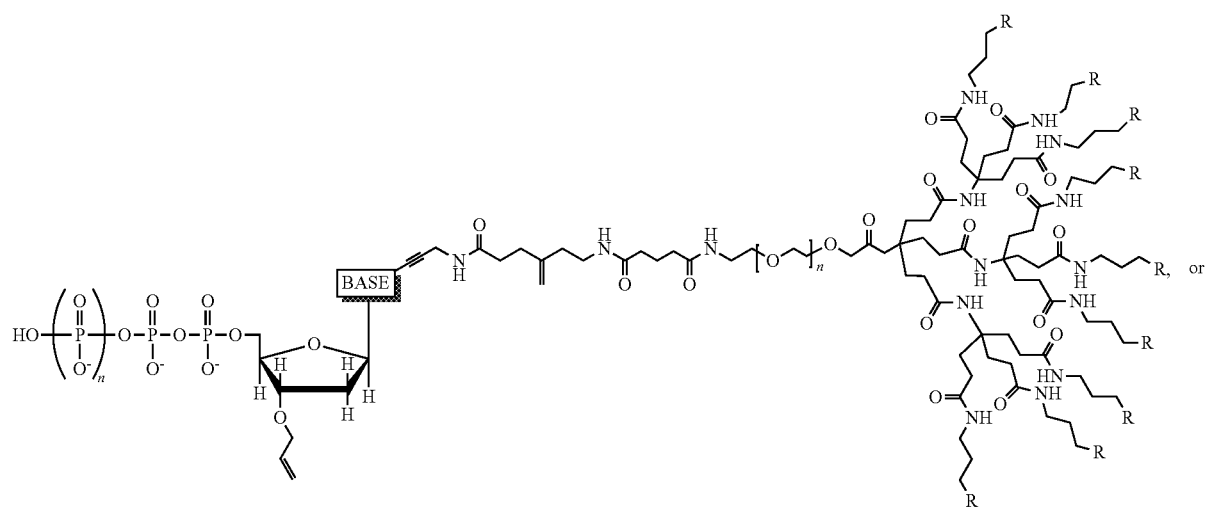

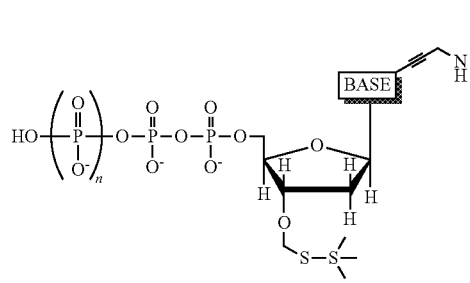
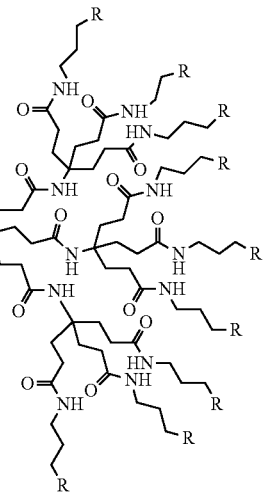

wherein, n=0, 1, 2, 3, 4, 5, or 6, and wherein R is a Raman active group.

In a further embodiment the Raman active group is any one of —N=N$^+$=N$^-$, —C≡CH, —C≡CD, —C≡CH$_3$ and —C≡N. In another embodiment a Raman cluster tag is attached to the 2' position of the sugar.

The invention also provides a compound having the structure:

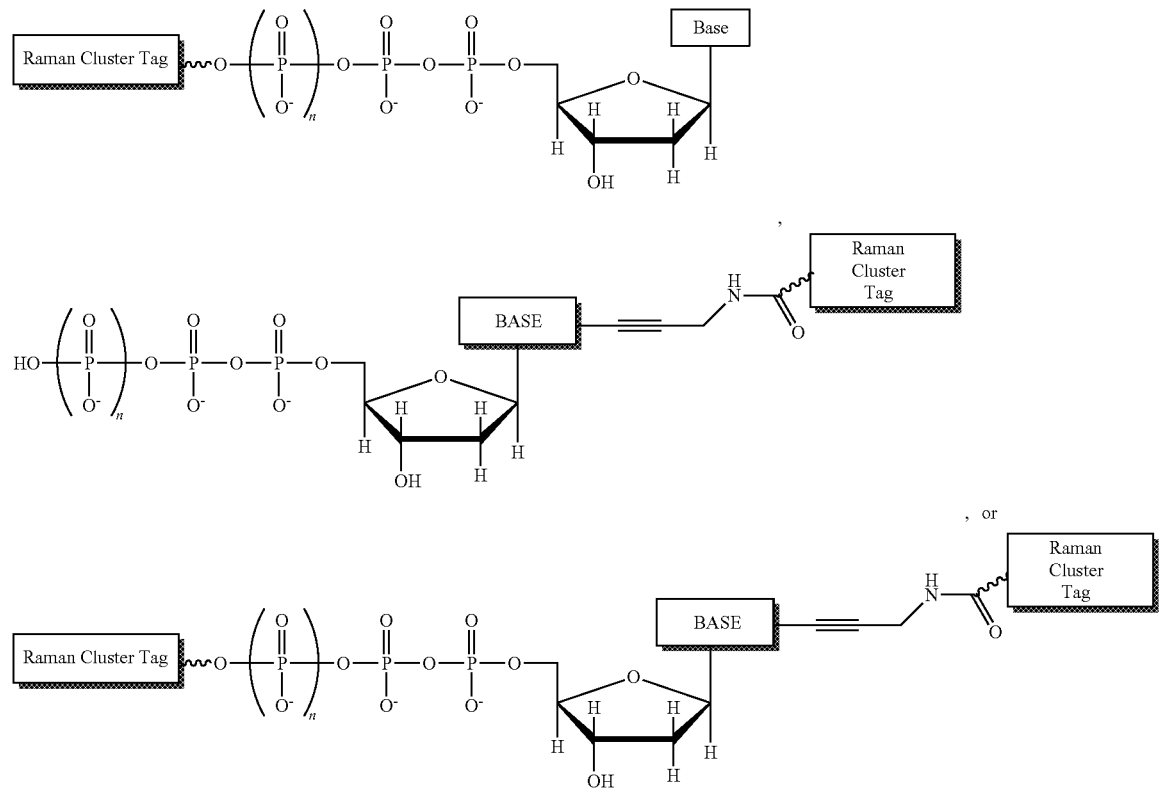

wherein base is any one of A, G, T, C, or U, or derivatives thereof, wherein n=0, 1, 2, 3, 4, 5, or 6, and wherein the Raman Cluster Tag is a chemical structure comprising one or more Raman active groups.

In another embodiment the compound has the structure:

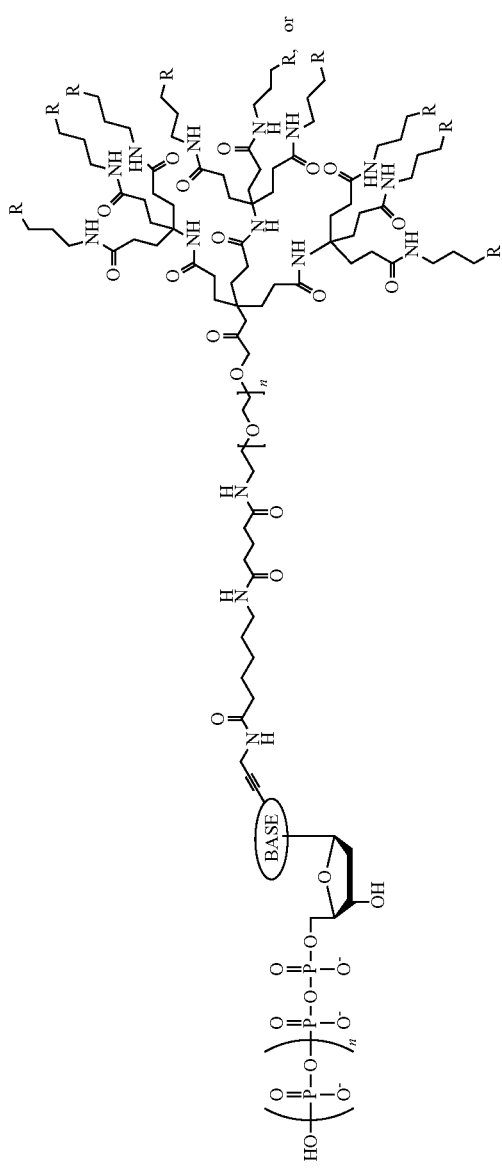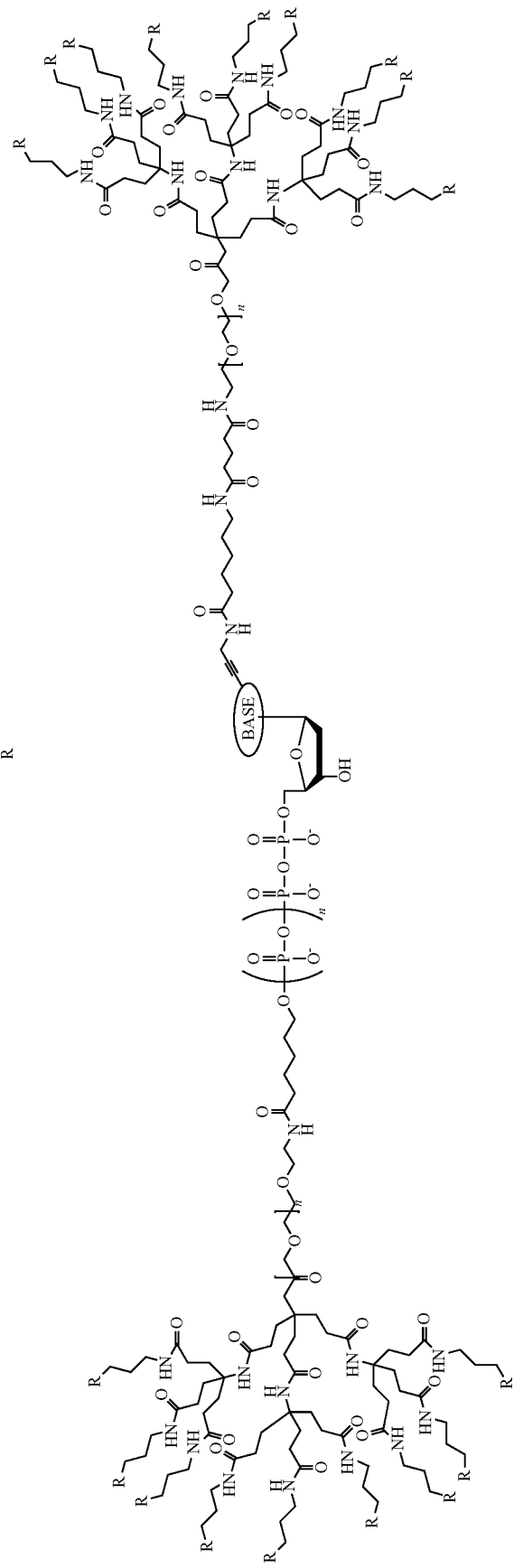

wherein R is a Raman active group and n=0, 1, 2, 3, 4, 5, or 6.

The invention also provides a compound having the structure:

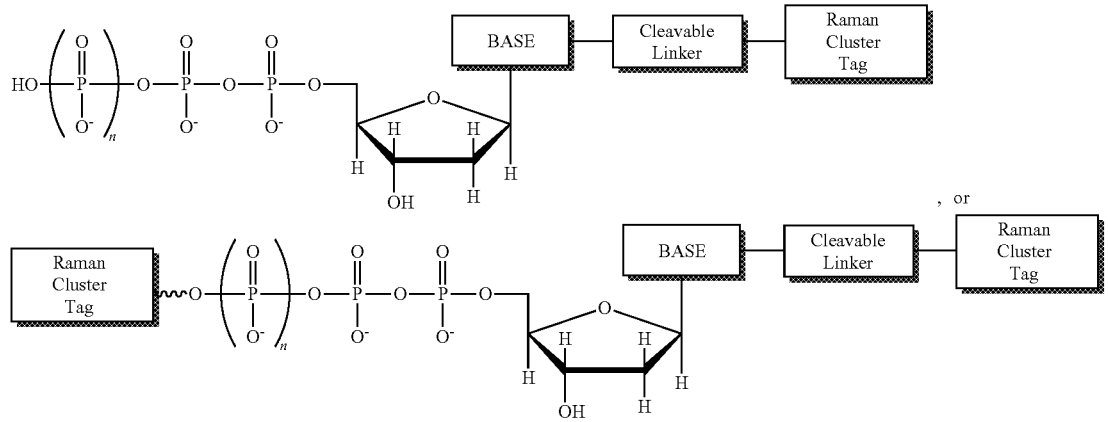

, or wherein base is A, G, T, C, or U, or derivatives thereof, wherein n 0, 1, 2, 3, 4, 5, or 6, and wherein the Raman Cluster Tag comprises one or more Raman active groups.

In another embodiment the cleavable linker is either chemically cleavable or photo cleavable. In another embodiment the cleavable linker comprises any one of an allyl, alkyl, carbonyl, Sieber linkers, indole, disulfide, dithiomethyl, azidomethyl, nitrobenzyl, or any derivative thereof. In another embodiment the cleavable linker is cleavable with one or more of Pd(0), tetrabutylammonium, DTT, a triphosphine, peroxydisulphate, iodine, or any derivative thereof. In another embodiment the compound has the structure:

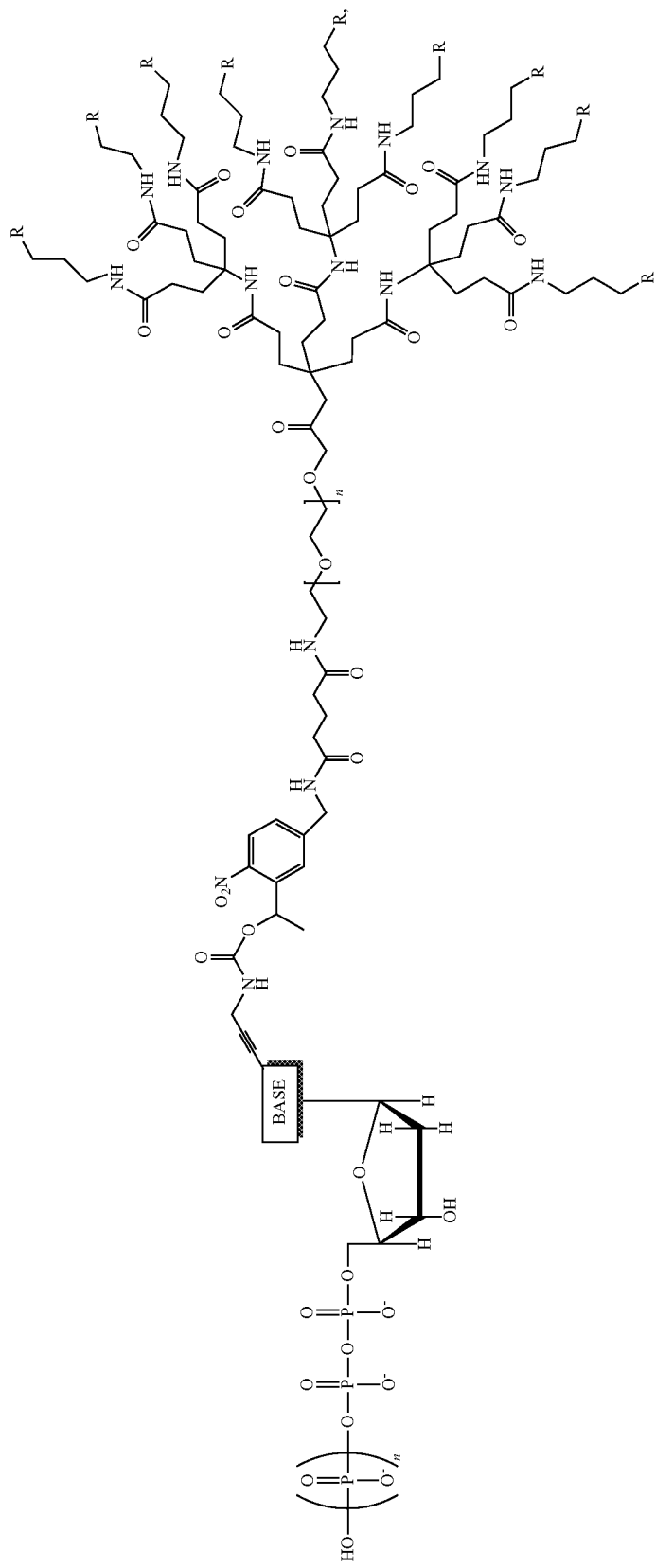

-continued
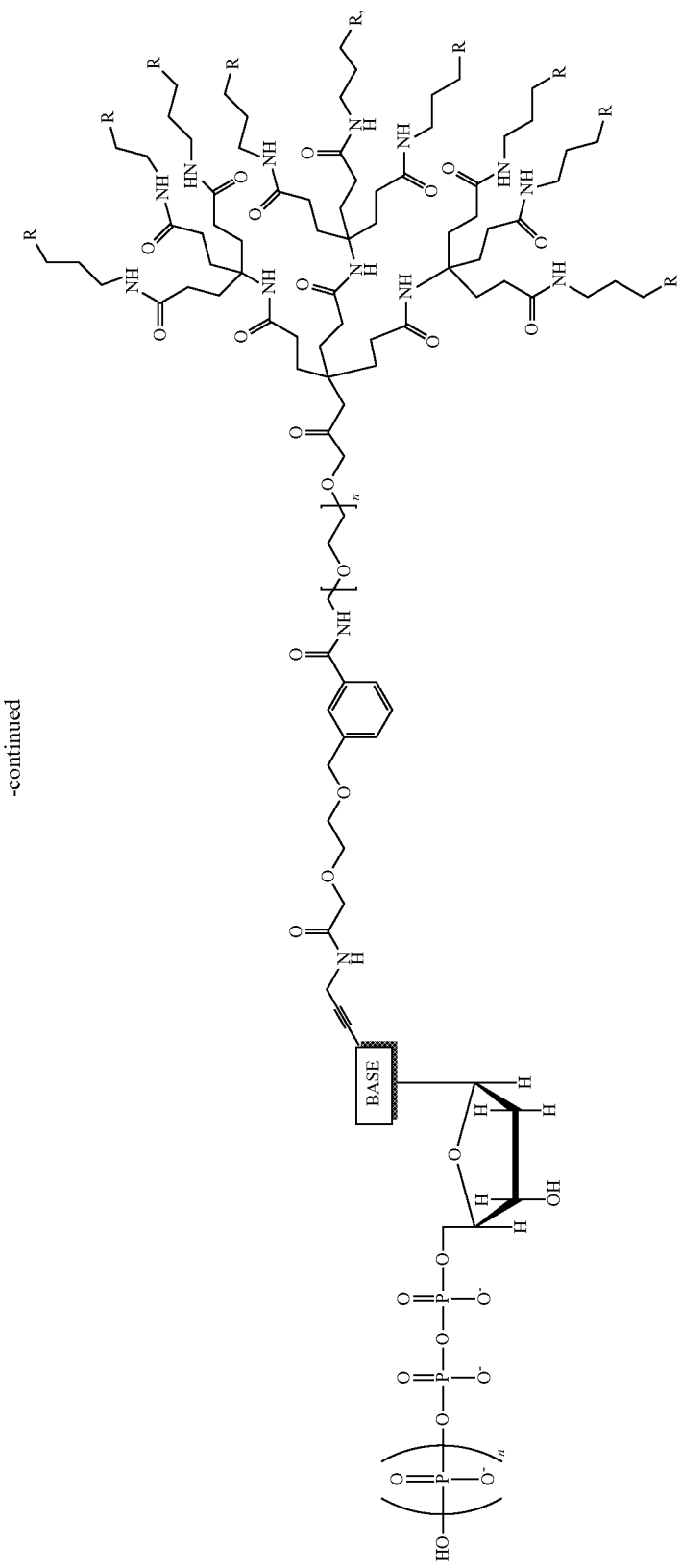

-continued
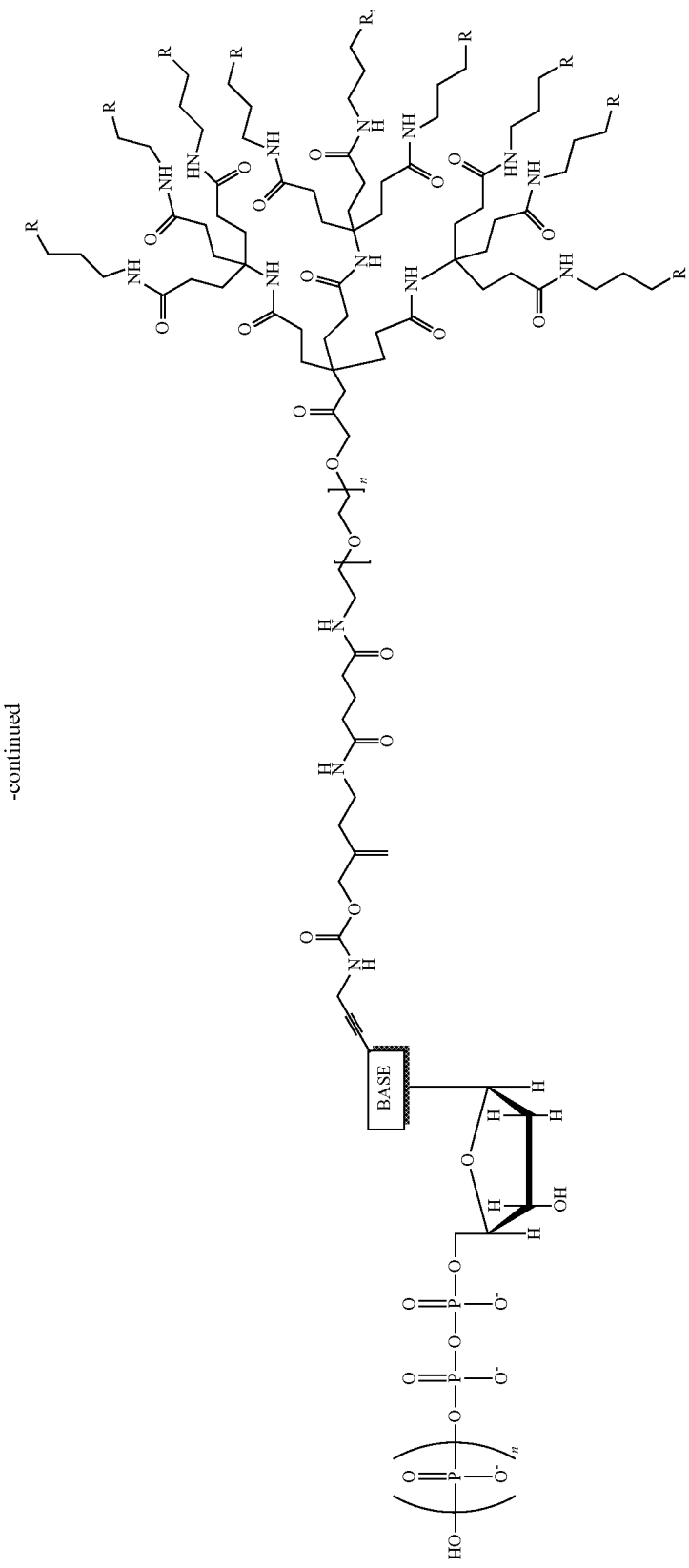

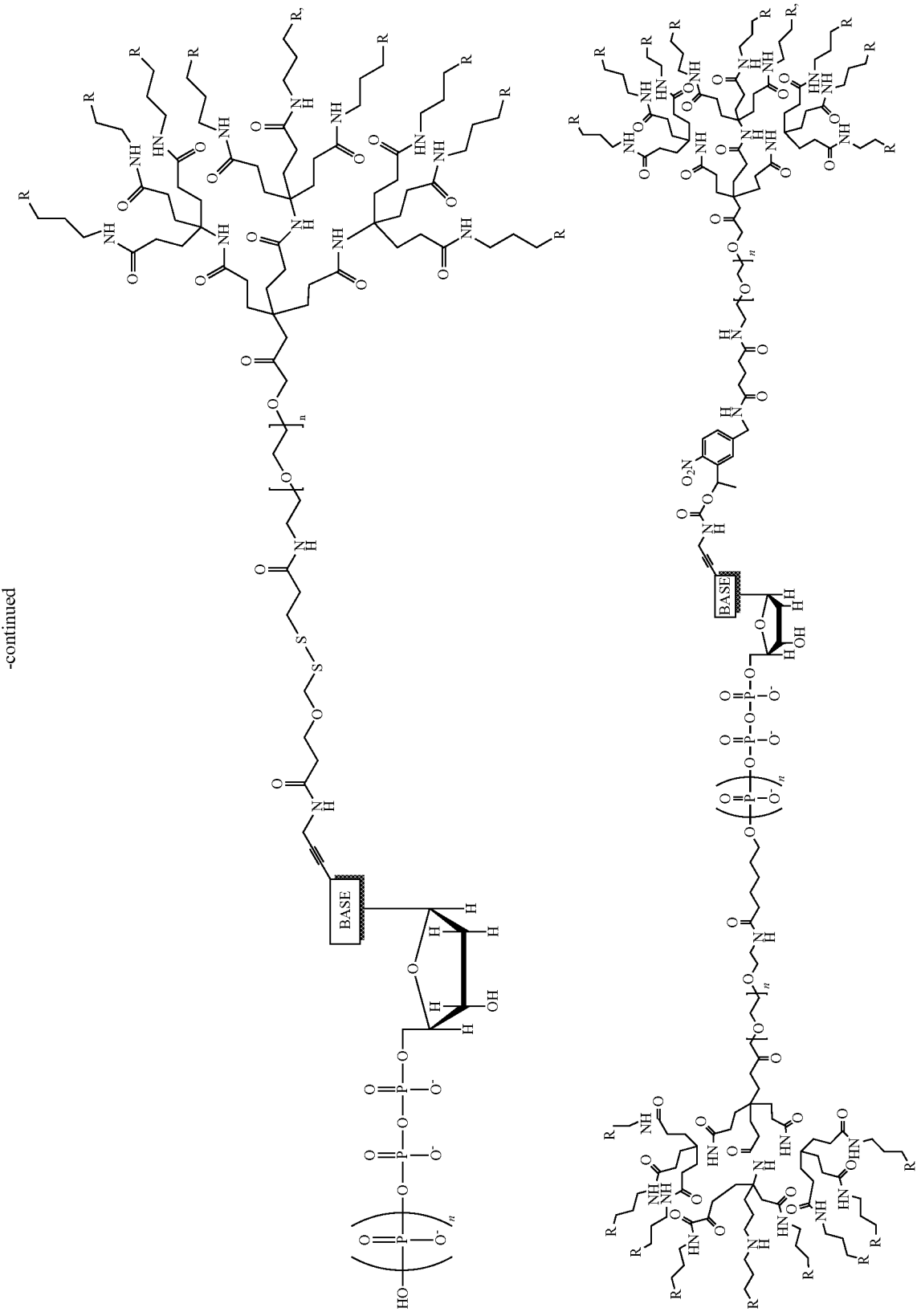

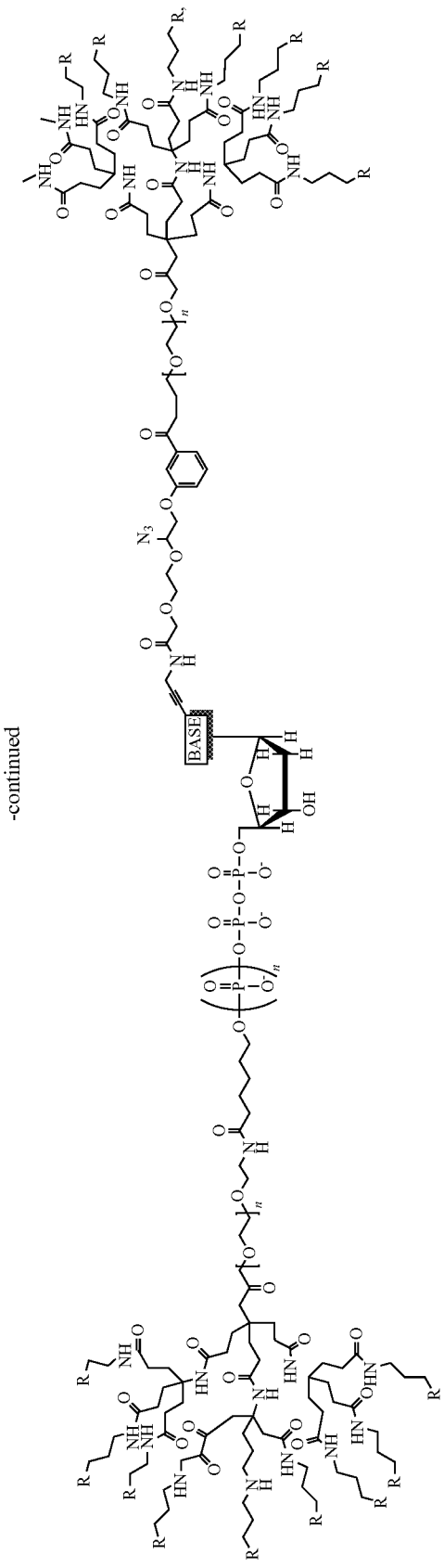

-continued
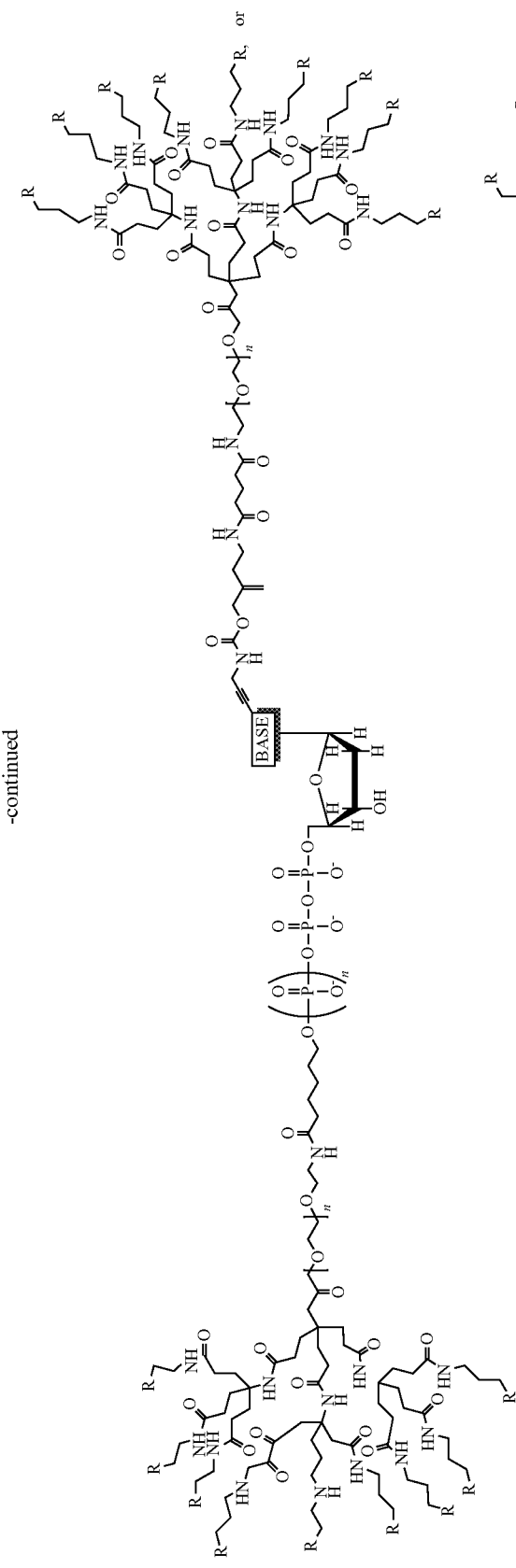
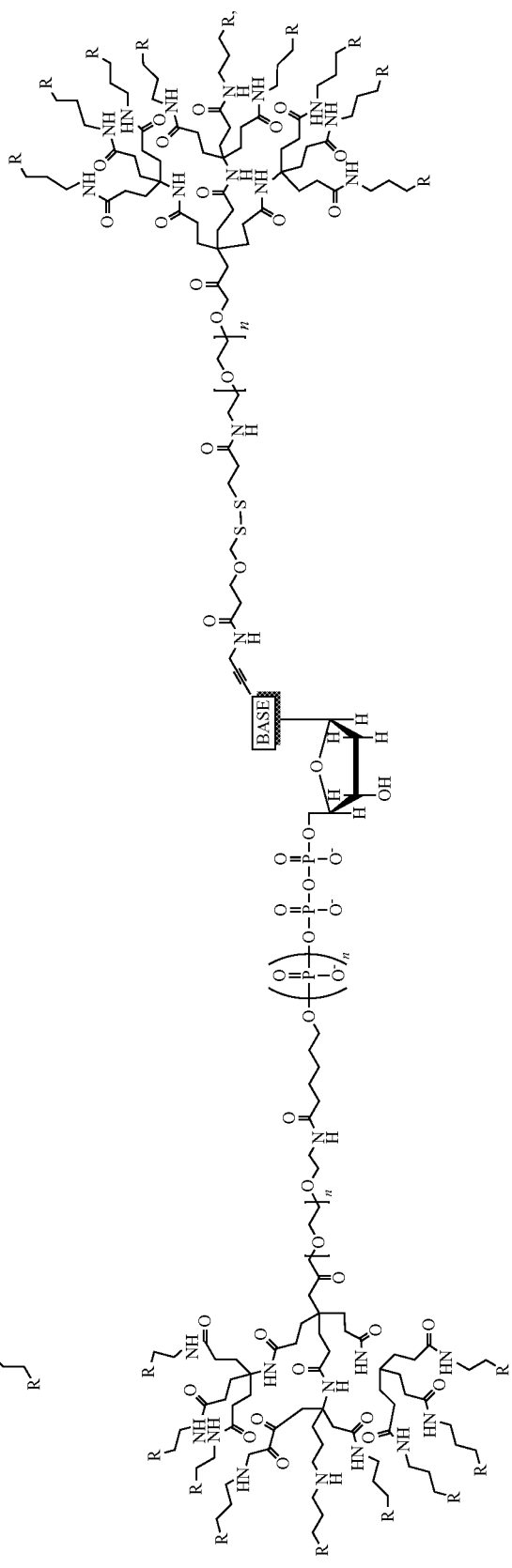

wherein R is a Raman active group and n=0, 1, 2, 3, 4, 5, or 6.

The invention also provides a compound having the structure:

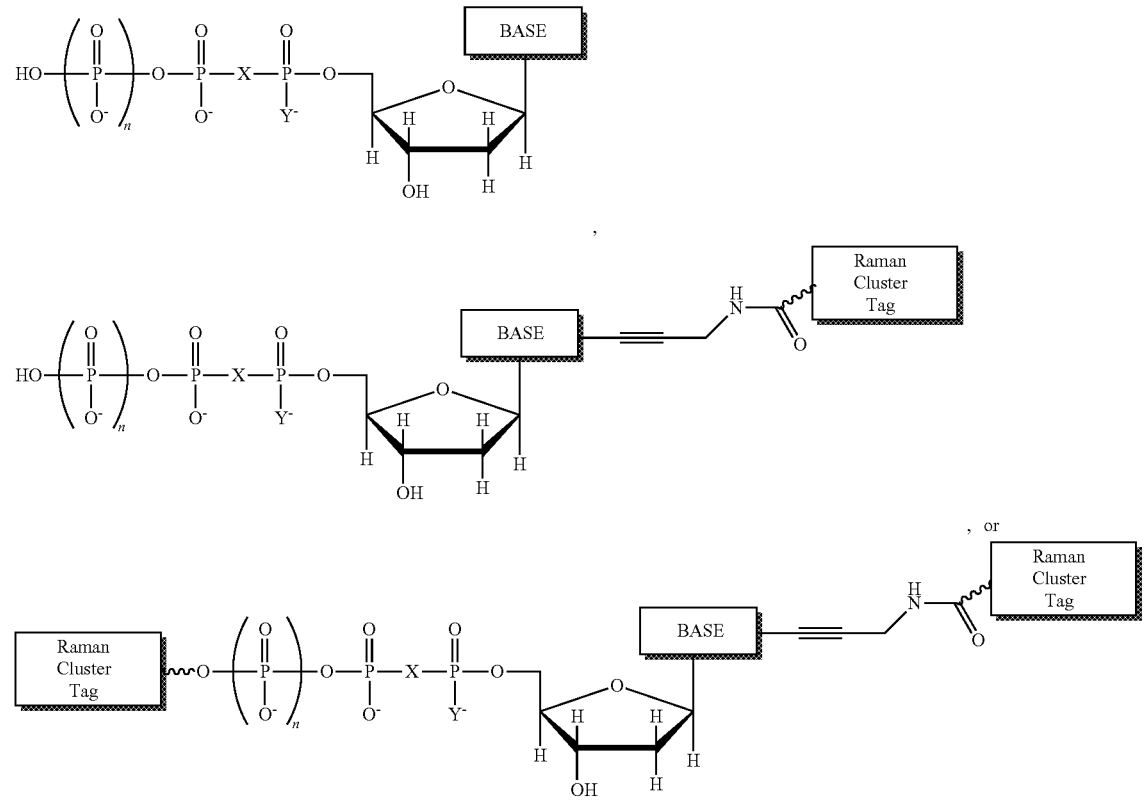

wherein base is any one of A, G, T, C, or U, or derivatives thereof, wherein n=0, 1, 2, 3, 4, 5, or 6, wherein the Raman Cluster Tag comprises Raman active groups, wherein X is any one of $CH_2$, NH, CHF—, or $CF_2$, and wherein Y is any one of O, S, or $BH_3$.

In another embodiment the compound has the structure:

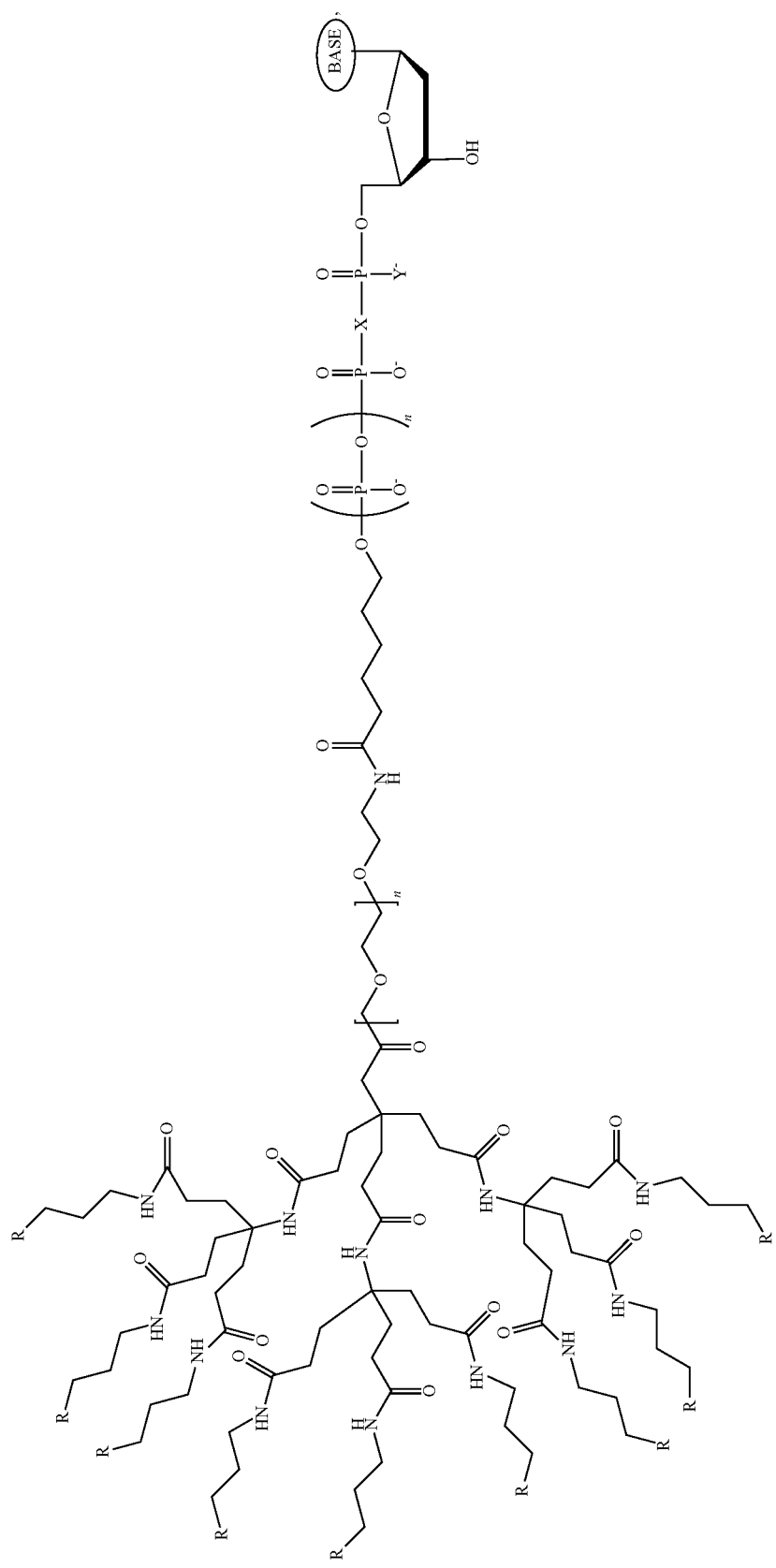

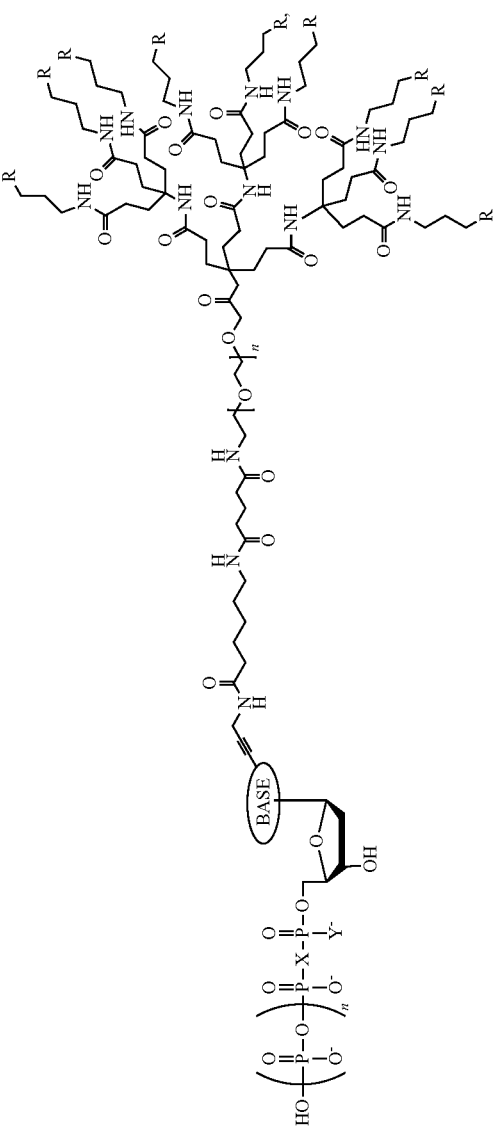
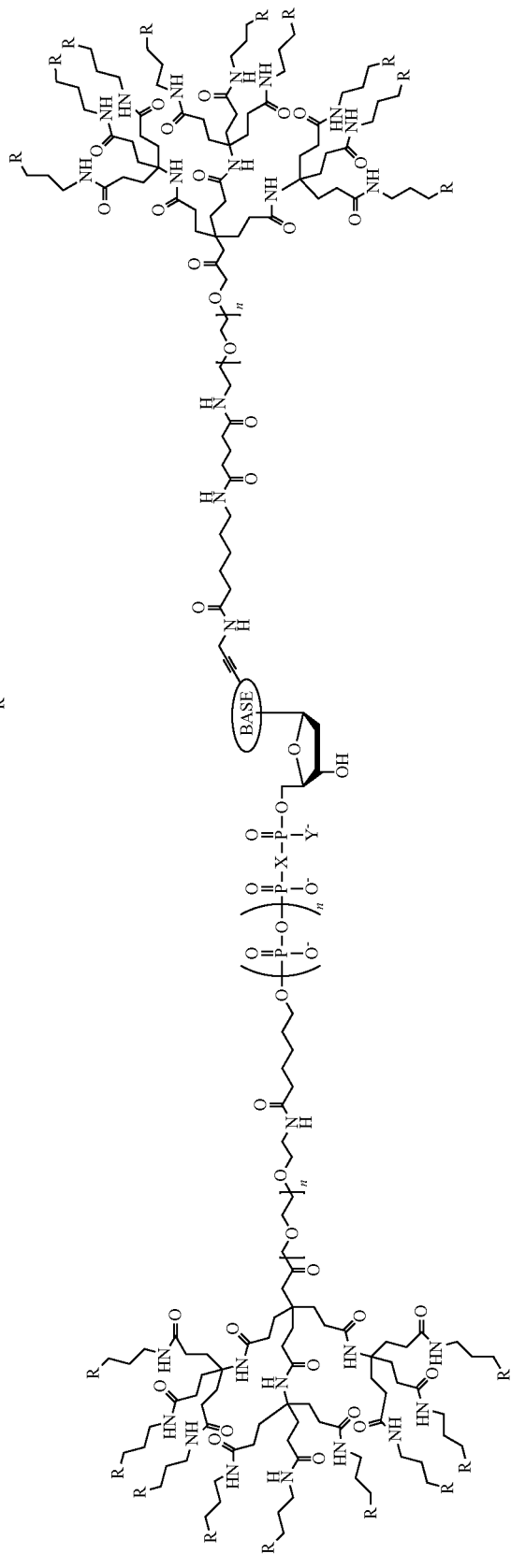

wherein R is a Raman active group and n=0, 1, 2, 3, 4, 5, or 6.

The invention also provides a compound having the structure:

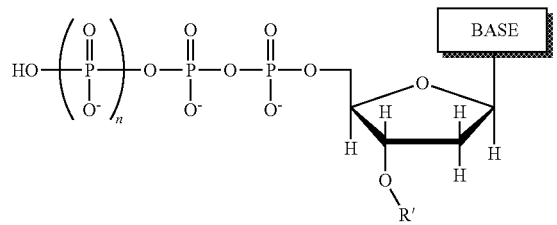

wherein base is any one of A, G, T, C, or U, or derivatives thereof, wherein n=0, 1, 2, 3, 4, 5, or 6, wherein R' comprises a Raman Cluster Tag, and wherein the Raman Cluster Tag comprises Raman active groups, and optionally the Raman cluster tag comprises a cleavable linker wherein cleaving the linker results in a 3'-OH.

In another embodiment the compound has structure:

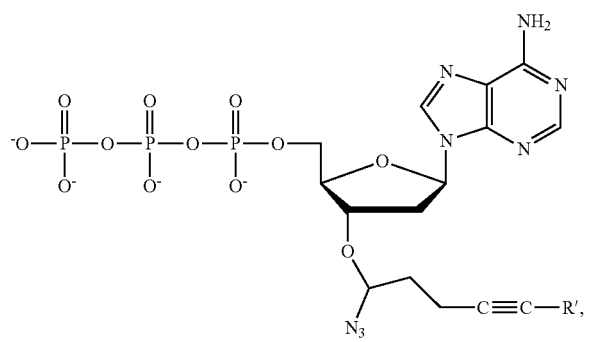

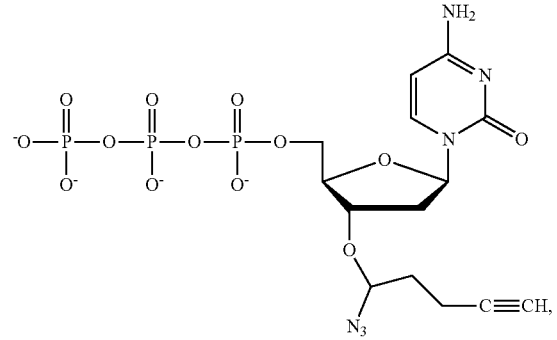

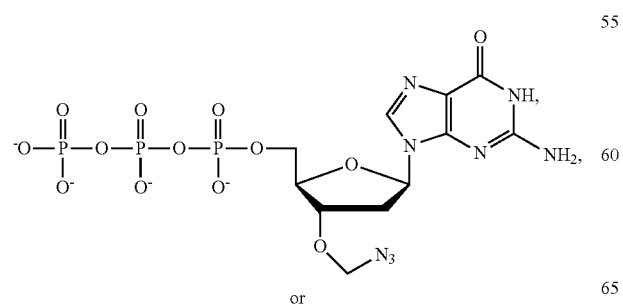

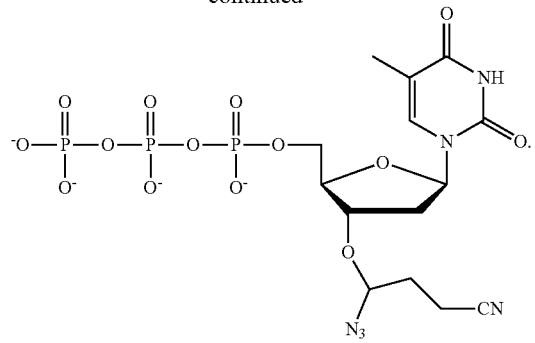

In another embodiment the Raman active groups are one or more of —N=N$^+$=N$^-$, —C≡CH, —C≡CD, —C≡CH$_3$ and —C≡N. In a another embodiment the Raman active groups have a Raman spectroscopy peak with a wave number from 2100 cm$^{-1}$ to 2300 cm$^{-1}$.

The invention also provides a method for sequencing a single-stranded polynucleotide molecule, comprising:

a) contacting the single-stranded polynucleotide having a primer hybridized to a portion thereof, with a nucleotide polymerase and a nucleoside polyphosphate analogue under conditions permitting the nucleotide polymerase to catalyze incorporation onto the primer of the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, so as to form a DNA extension product, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogue has the structure:

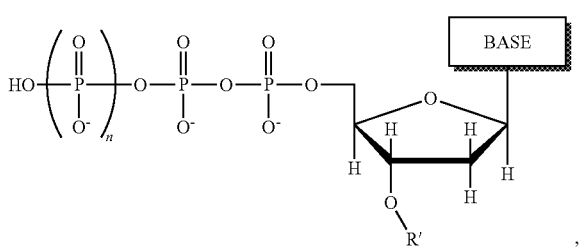

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tag comprises one or more Raman active groups, wherein the Raman spectroscopy peak of the Raman cluster tag is predetermined, and wherein when the cleavable linker is cleaved it results in a 3'-OH, and wherein if the base of the analogue is not complementary to the nucleotide residue of the single-stranded polynucleotide which is immediately 5' to the nucleoside residue of the single-stranded polynucleotide hybridized to the 3' terminal nucleotide residue of the primer, then iteratively repeating the contacting with a nucleoside polyphosphate having a different base until the nucleoside polyphosphate analogue has a base that is complementary;
b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded polynucleotide;
c) cleaving the cleavable linker, so as to thereby create a 3'-OH;
d) iteratively performing steps a) through c) for each nucleotide residue of the single-stranded polynucleotide to be sequenced so as to thereby determine the sequence of the single-stranded polynucleotide.

The invention also provides a method for sequencing a single-stranded polynucleotide molecule, comprising:
a) contacting the single-stranded polynucleotide having a primer hybridized to a portion thereof, with a nucleotide polymerase and four nucleoside polyphosphate analogues under conditions permitting the nucleotide polymerase to catalyze incorporation onto the primer of a nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, so as to form a DNA extension product, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

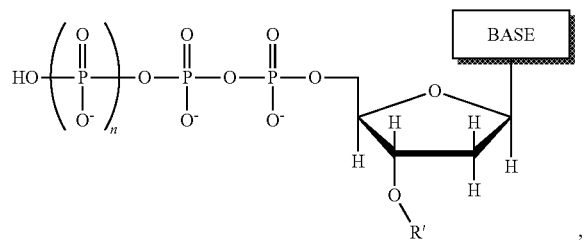

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein each analogue comprises a base which is different from the base of each of the remaining three analogues, and wherein when the cleavable linker is cleaved it results in a 3'-OH;
b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded polynucleotide;
c) cleaving the cleavable linker of R', so as to thereby create a 3'-OH;
d) iteratively performing steps a) through c) for each nucleotide residue of the single-stranded polynucleotide to be sequenced so as to thereby determine the sequence of the single-stranded polynucleotide.

In another embodiment the nucleoside polyphosphate analogues have the structure:

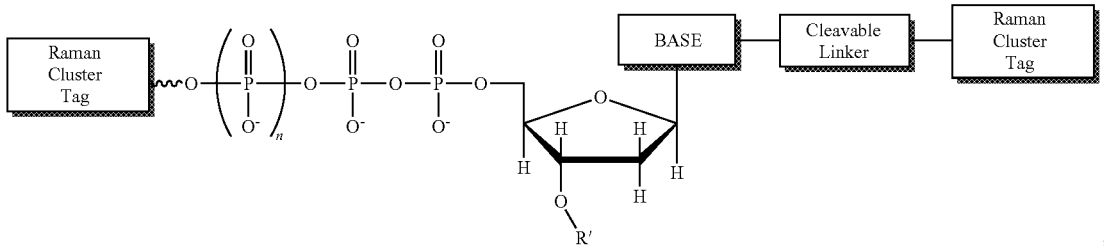

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein each analogue comprises a base which is different from the base of each of the remaining three analogues, and wherein when the cleavable linker of R' is cleaved it results in a 3'-OH,
wherein in step c) the cleavable linker attached to the base and the cleavable linker of R' are cleaved under identical circumstances.

The invention also provides a method for sequencing a single-stranded polynucleotide molecule, comprising:
a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

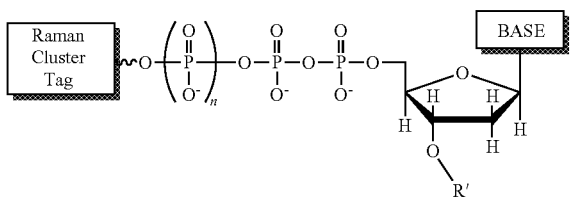

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tags comprise one or more Raman active groups, wherein the Raman spectroscopy peaks of the Raman cluster tags are predetermined, wherein the Raman spectroscopy peaks of the tags on each analogue are distinguishable from the Raman spectroscopy peaks of the tags on each of the remaining analogues, wherein each analogue comprises a base which is different from the base of each of the remaining three analogues, and wherein when the cleavable linker is cleaved it results in a 3'-OH;

b) determining the wavenumber of the Raman spectroscopy peaks of the Raman cluster tags of the analogue in the ternary complex, so as to thereby determine the identity of the nucleoside polyphosphate and the identity of the complementary nucleotide residue in the single-stranded polynucleotide;

c) cleaving the cleavable linker, so as to thereby create a 3'-OH, removing some or all of the non-catalytic metal ions, and adding catalytic metal ions, thereby permitting the nucleotide polymerase to cleave the terminal phosphate with the bound Raman cluster tag and catalyze the incorporation of the analogue into the primer so as to form a DNA extension product;

d) iteratively performing steps a) through c) for each nucleotide residue of the single-stranded polynucleotide to be sequenced so as to thereby determine the sequence of the single-stranded polynucleotide.

In another embodiment the nucleoside polyphosphate analogues have the structure:

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tags comprise one or more Raman active groups, wherein the Raman spectroscopy peaks of the Raman cluster tags are predetermined, wherein the Raman spectroscopy peaks of the tags on each analogue are distinguishable from the Raman spectroscopy peaks of the tags on each of the remaining analogues, wherein each analogue comprises a base which is different from the base of each of the remaining three analogues, and wherein when the cleavable linker of R' is cleaved it results in a 3'-OH, and wherein step c) also includes cleaving the cleavable linker attached to the base.

In another embodiment the cleavable linker of R' comprises any one of an allyl, alkyl, carbonyl, Sieber linkers, indole, disulfide, dithiomethyl, azidomethyl, nitrobenzyl, or any derivative thereof.

In another embodiment the cleavable linker of R' is cleavable with one or more of Pd(0), tetrabutylammonium, DTT, a triphosphine, peroxydisulphate, iodine, or any derivative thereof.

The invention also provides a method for sequencing a single-stranded polynucleotide molecule, comprising:

a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

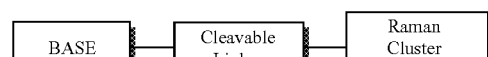
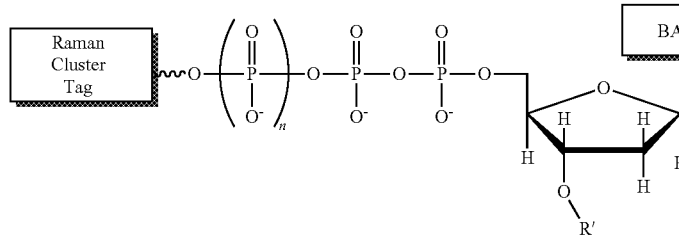
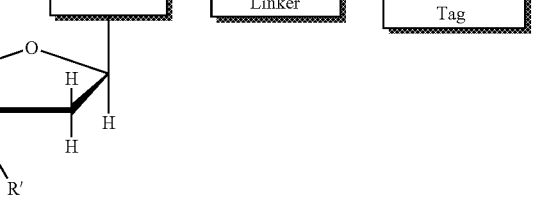

,

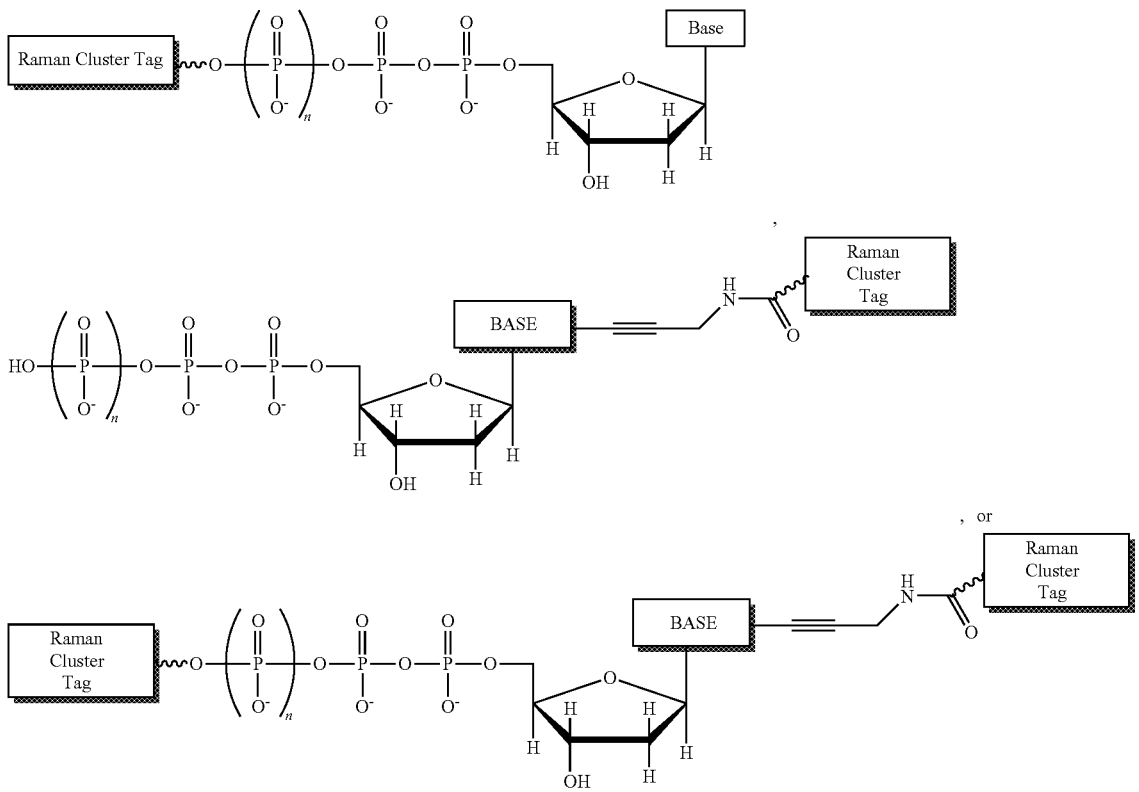

wherein base is any one of A, G, T, C, or U, or derivatives thereof, wherein n=0, 1, 2, 3, 4, 5, or 6, wherein the Raman cluster tag comprises one or more Raman active groups, wherein the Raman spectroscopy peaks of the Raman cluster tag is predetermined, wherein the Raman spectroscopy peaks of the tag on each analogue are distinguishable from the Raman spectroscopy peaks of the tags on each of the remaining analogues, wherein each analogue comprises a base which is different from the base of each of the remaining three analogues;

b) determining the wavenumber of the Raman spectroscopy peaks of the Raman cluster tag of the analogue in the ternary complex, so as to thereby determine the identity of the nucleoside polyphosphate and the identity of the complementary nucleotide residue in the single-stranded polynucleotide;

c) contacting the ternary complex with four nucleotide reversible terminators thereby replacing the nucleoside polyphosphate analogue with a nucleotide reversible terminator with the proviso that the nucleotide reversible terminator is complementary to a nucleotide residue of the single-stranded polynucleotide which is immediately 5' to a nucleotide residue of the single-stranded polynucleotide hybridized to the 3' terminal nucleotide of the primer, wherein the nucleotide reversible terminators have the structure:

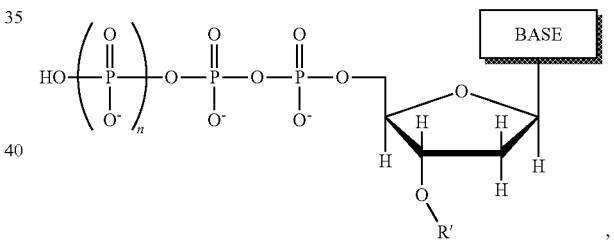

wherein base is any one of A, G, T, C, or U, or derivatives thereof, wherein n=0, 1, 2, 3, 4, 5, or 6, wherein R' comprises a cleavable 3' blocking group, wherein each nucleotide reversible terminator comprises a base which is different from the base of each of the remaining nucleotide reversible terminators;

d) removing some or all of the non-catalytic metal ions, and adding catalytic metal ions, thereby permitting the nucleotide polymerase to incorporate the nucleotide reversible terminator into the primer so as to form a DNA extension product;

e) cleaving the blocking group thereby resulting in a 3'-OH;

f) iteratively performing steps a) through e) for each nucleotide residue of the single-stranded polynucleotide to be sequenced so as to thereby determine the sequence of the single-stranded polynucleotide.

The invention also provides a method for sequencing a single-stranded polynucleotide molecule, comprising:

a) contacting the single-stranded polynucleotide having a primer hybridized to a portion thereof, with a nucleotide polymerase and four nucleoside polyphosphate analogues under conditions permitting the nucleotide polymerase to catalyze incorporation onto the primer of a nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, so as to form a DNA extension product, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

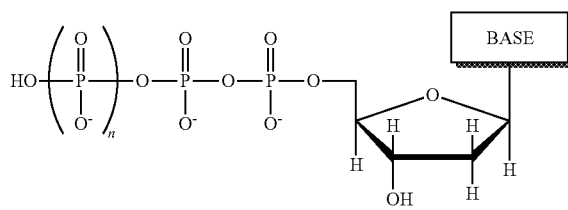

, wherein base is any one of A, G, T, C, or U, or derivatives thereof, wherein n=0, 1, 2, 3, 4, 5, or 6, and wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein the presence of the Raman cluster tag prevents the polymerase from incorporating a subsequent nucleotide, wherein each analogue comprises a base which is different from the base of each of the remaining three analogues, b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded polynucleotide;

c) cleaving the cleavable linker, thereby permitting the polymerase to incorporate a subsequent nucleoside polyphosphate analogue;

d) iteratively performing steps a) through c) for each nucleotide residue of the single-stranded polynucleotide to be sequenced so as to thereby determine the sequence of the single-stranded polynucleotide.

The invention also provides a method for sequencing a single-stranded polynucleotide molecule, comprising:

a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

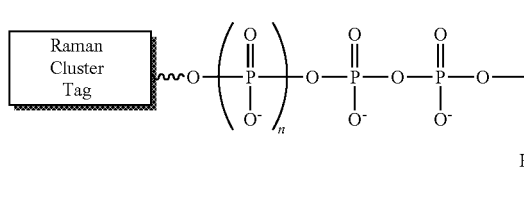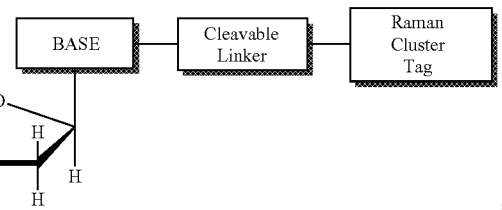

, wherein base is any one of A, G, T, C, or U, or derivatives thereof, wherein n=0, 1, 2, 3, 4, 5, or 6, wherein the Raman cluster tags comprise one or more Raman active groups, wherein the Raman spectroscopy peaks of the Raman cluster tags are predetermined, wherein the Raman spectroscopy peaks of the tags on each analogue are distinguishable from the Raman spectroscopy peaks of the tags on each of the remaining analogues, wherein the presence of the Raman cluster tag linked to the base prevents the polymerase from incorporating a subsequent nucleoside polyphosphate, wherein each analogue comprises a base which is different from the base of each of the remaining three analogues, b) determining the wavenumber of the Raman spectroscopy peaks of the Raman cluster tags of the analogue in the ternary complex, so as to thereby determine the identity of the nucleoside polyphosphate and the identity of the complementary nucleotide residue in the single-stranded polynucleotide;

c) cleaving the cleavable linker so as to remove the tag attached to the base, removing some or all of the non-catalytic metal ions, adding one or more catalytic metal ions, thereby permitting the nucleotide polymerase to cleave the terminal phosphate with the bound Raman cluster tag and catalyze the incorporation of the analogue into the primer so as to form a DNA extension product;

d) iteratively performing steps a) through c) for each nucleotide residue of the single-stranded polynucleotide to be sequenced so as to thereby determine the sequence of the single-stranded polynucleotide.

The invention also provides a method for sequencing a single-stranded polynucleotide molecule, comprising:

a) contacting the single-stranded polynucleotide having a primer hybridized to a portion thereof, with a nucleotide polymerase, four nucleoside polyphosphate analogues, under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein one or more of the polymerase, single-stranded polynucleotide, or primer are located within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, wherein the nucleoside polyphosphate analogues have the structure:

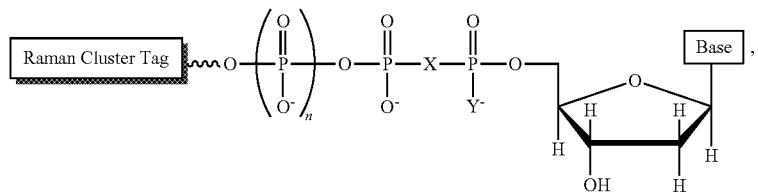

wherein base is any one of A, G, T, C, or U, or derivatives thereof, wherein n=0, 1, 2, 3, 4, 5, or 6, wherein the Raman Cluster Tag comprises Raman active groups, wherein X is any one of $CH_2$, NH, CHF—, or $CF_2$, and wherein Y is any one of O, S, or $BH_3$, wherein X and/or Y prevent the nucleotide polymerase from cleaving the bond between the α and β phosphate, wherein the Raman spectroscopy peaks of the Raman cluster tag is predetermined, wherein the Raman spectroscopy peaks of the tag on each analogue are distinguishable from the Raman spectroscopy peaks of the tags on each of the remaining analogues, wherein each analogue comprises a base which is different from the base of each of the remaining three analogues;

b) determining the wavenumber of the Raman spectroscopy peaks of the Raman cluster tag of the analogue in the ternary complex, so as to thereby determine the identity of the nucleoside polyphosphate and the identity of the complementary nucleotide residue in the single-stranded polynucleotide;

c) contacting the ternary complex with four nucleotide reversible terminators thereby replacing the nucleoside polyphosphate analogue with a nucleotide reversible terminator with the proviso that the nucleotide reversible terminator is complementary to a nucleotide residue of the single-stranded polynucleotide which is immediately 5' to a nucleotide residue of the single-stranded polynucleotide hybridized to the 3' terminal nucleotide of the primer, wherein each nucleotide reversible terminator has the structure:

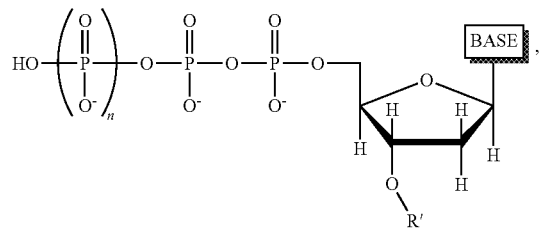

wherein base is any one of A, G, T, C, or U, or derivatives thereof, wherein n=0, 1, 2, 3, 4, 5, or 6, wherein R' comprises a cleavable 3' blocking group, wherein each nucleotide reversible terminator comprises a base which is different from the base of each of the remaining nucleotide reversible terminators;

d) removing some or all of the non-catalytic metal ions, and adding catalytic metal ions, thereby permitting the nucleotide polymerase to incorporate the nucleotide reversible terminator into the primer so as to form a DNA extension product;

e) cleaving the blocking group thereby resulting in a 3'-OH;

f) iteratively performing steps a) through e) for each nucleotide residue of the single-stranded polynucleotide to be sequenced so as to thereby determine the sequence of the single-stranded polynucleotide.

In further embodiments the cleavable linker attached to the base comprises any one of an allyl, alkyl, carbonyl, Sieber linkers, indole, disulfide, dithiomethyl, azidomethyl, nitrobenzyl, or any derivative thereof. In further embodiments the cleavable linker attached to the base is cleavable with one or more of Pd(0), tetrabutylammonium, DTT, a triphosphine, peroxydisulphate, iodine, or any derivative thereof.

In further embodiments the non-catalytic metal ions are one or more of $Sr^{++}$ and $Ca^{++}$. In further embodiments the catalytic metal ions are one or more of $Mg^{++}$ or $Mn^{++}$.

In a further embodiment the Raman active groups are one or more of —N=$N^+$=$N^-$, —C≡CH, —C≡CD, —C≡$CH_3$ and —C≡N. In another embodiment the Raman active groups have a Raman spectroscopy peak with a wave number from 2100 $cm^{-1}$ to 2300 $cm^{-1}$.

In another embodiment the primer is attached to the surface or other substrate.

In another embodiment single-stranded polynucleotide comprises an adapter that is a predetermined nucleotide sequence, and wherein the primer comprises a complementary nucleotide sequence.

In another embodiment prior to step a) the single-stranded polynucleotide is Polymerase Chain Reaction (PCR)-amplified so as to thereby produce a plurality of copies which are attached to a bead, and wherein the beads with the attached plurality of single-stranded polynucleotide copies are proximally located to the surface so as to thereby permit the contacting in a region of enhanced sensitivity for surface enhanced Raman spectroscopy.

In another embodiment there are a plurality of polymerases and primers so as to thereby permit simultaneous parallel sequencing of the single-stranded polynucleotide copies.

In another embodiment the polymerase or polymerases are tethered to the noble metal nanoparticles. In another embodiment the noble metal nanoparticles are silver and/or gold nanoparticles. In another embodiment the polymerase or polymerases have 1 or more attached and/or conjugated noble metal nanoparticles, wherein the noble metal nanoparticles are a surface-enhanced Raman spectroscopy (SERS) substrates.

In another embodiment the noble metal nanoparticles are either gold or silver nanoparticles.

In another embodiment the metal nanoparticles of the polymerase or polymerases are between 3 nm and 10 nm.

In another embodiment the polymerase or polymerases have 2, 3, 4, or 5 metal nanoparticles.

In another embodiment the metal nanoparticles of the polymerase or polymerases are attached and/or conjugated to the polymerase 1 nm-3 nm from the active site of the polymerase. In a further embodiment the metal nanoparticles of the polymerase or polymerases are attached and/or conjugated to the polymerase or polymerases 1 nm-3 nm from the active site of the polymerase, thereby creating a region of enhanced sensitivity for surface enhanced Raman spectroscopy (SERS) at the active site. In a further embodiment the metal nanoparticles are attached and/or conjugated to the polymerase such that when a nucleoside and/or nucleotide are in the active site of the polymerase, and wherein the nucleoside and/or nucleotide are tagged with a Raman active molecule, the metal nanoparticles are located 1 nm-3 nm from the Raman active molecule.

In another embodiment the attached and/or conjugated metal nanoparticles of the polymerase create a region of enhanced sensitivity for surface enhanced Raman spectroscopy (SERS) at the location of the Raman active molecule.

The invention also provides a method of single molecule real-time sequencing of a single-stranded polynucleotide, comprising:

a) first, contacting the single-stranded polynucleotide having a primer hybridized to a portion thereof, with a nucleotide polymerase, four nucleoside polyphosphate analogues, under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein the ternary complex is formed within 10 nm of a surface or other substrate with embedded, derivatized, attached, or conjugated noble metal nanoparticles that are interspersed between 1 nm-5 nm on the surface, thereby creating regions of enhanced sensitivity for surface enhanced Raman spectroscopy, and wherein the polymerase is attached to a noble metal nanoparticle on the surface or other substrate thereof, wherein the nucleoside polyphosphate analogues have the structure:

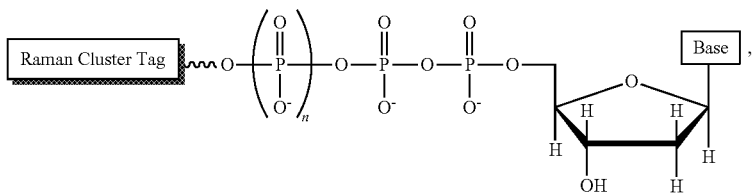

wherein base is any one of A, G, T, C, or U, or derivatives thereof, wherein n=0, 1, 2, 3, 4, 5, or 6, wherein the Raman cluster tag comprises one or more Raman active groups, wherein the Raman spectroscopy peaks of the Raman cluster tag are predetermined, wherein the Raman spectroscopy peaks of the tag on each analogue are distinguishable from the Raman spectroscopy peaks of the tags on each of the remaining analogues, wherein each analogue comprises a base which is different from the base of each of the remaining three analogues, b) determining the wavenumber of the Raman spectroscopy peaks of the Raman cluster tag of the analogue in the ternary complex, so as to thereby determine the identity of the nucleoside polyphosphate and the identity of the complementary nucleotide residue in the single-stranded polynucleotide;

c) permitting the polymerase to cleave the terminal phosphate with the attached Raman cluster tag, thereby allowing the polymerase to catalyze the incorporation of the nucleoside polyphosphate into the primer as a nucleotide extension product;

d) iteratively performing steps a) through c) for each nucleotide residue of the single-stranded polynucleotide to be sequenced so as to thereby determine the sequence of the single-stranded polynucleotide.

In another embodiment the nanoparticles are one of silver or gold.

In another embodiment the single-stranded polynucleotide comprises an adapter which is a predetermined nucleotide sequence, and wherein the hybridized primer comprises a nucleotide sequence complementary to portion of the adapter.

In another embodiment the single-stranded polynucleotide is completely sequenced, a subsequent single-stranded polynucleotide is sequenced using the same polymerase.

In another embodiment the subsequent single-stranded polynucleotide is sequenced, the Raman spectroscopy signals of the sequenced nucleotides corresponding to the predetermined adaptor sequence indicate that a subsequent single-stranded polynucleotide is being sequenced.

The invention also provides a method for sequencing a single-stranded polynucleotide molecule, comprising:

a) contacting the single-stranded polynucleotide having a primer hybridized to a portion thereof, with a nucleotide polymerase and a nucleoside polyphosphate analogue under conditions permitting the nucleotide polymerase to catalyze incorporation onto the primer of the nucleoside polyphosphate if the analogue is complementary to a nucleotide residue of the single-stranded polynucleotide which is immediately 5' to a nucleotide residue of the single-stranded polynucleotide hybridized to the 3' terminal nucleotide of the primer, so as to form a DNA extension product, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogue has the structure:

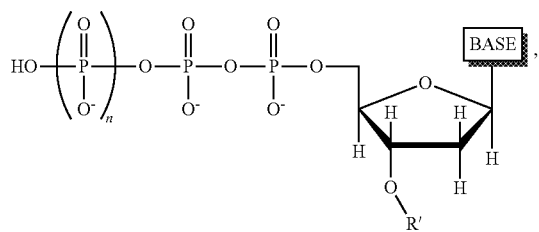

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tag comprises one or more Raman active groups, wherein the Raman spectroscopy peak of the Raman cluster tag is predetermined, and wherein when the cleavable linker is cleaved it results in a 3'-OH, and wherein if the base of the analogue is not complementary to the nucleotide residue of the single-stranded polynucleotide which is immediately 5' to the nucleoside residue of the single-stranded polynucleotide hybridized to the 3' terminal nucleotide residue of the primer, then iteratively repeating the contacting with a nucleoside polyphosphate having a different base until the nucleoside polyphosphate analogue has a base that is complementary;

b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded polynucleotide;

c) cleaving the cleavable linker, so as to thereby create a 3'-OH;

d) iteratively performing steps a) through c) for each nucleotide residue of the single-stranded polynucleotide to be sequenced so as to thereby determine the sequence of the single-stranded polynucleotide.

The invention also provides a method for sequencing a single-stranded polynucleotide molecule, comprising:

a) contacting the single-stranded polynucleotide having a primer hybridized to a portion thereof, with a nucleotide polymerase and four nucleoside polyphosphate analogues under conditions permitting the nucleotide polymerase to catalyze incorporation onto the primer of a nucleoside polyphosphate if the analogue is complementary to a nucleotide residue of the single-stranded polynucleotide which is immediately 5' to a nucleotide residue of the single-stranded polynucleotide hybridized to the 3' terminal nucleotide of the primer, so as to form a DNA extension product, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

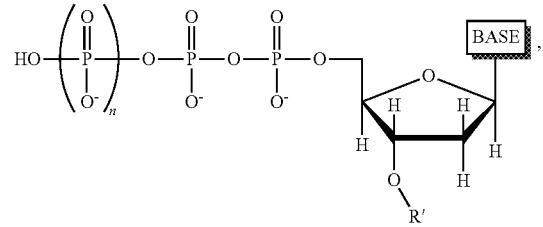

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein each analogue comprises a base which is different from the base of each of the remaining three analogues, and wherein when the cleavable linker is cleaved it results in a 3'-OH;

b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded polynucleotide;

c) cleaving the cleavable linker of R', so as to thereby create a 3'-OH;

d) iteratively performing steps a) through c) for each nucleotide residue of the single-stranded polynucleotide to be sequenced so as to thereby determine the sequence of the single-stranded polynucleotide.

In another embodiment the nucleoside polyphosphate analogues have the structure:

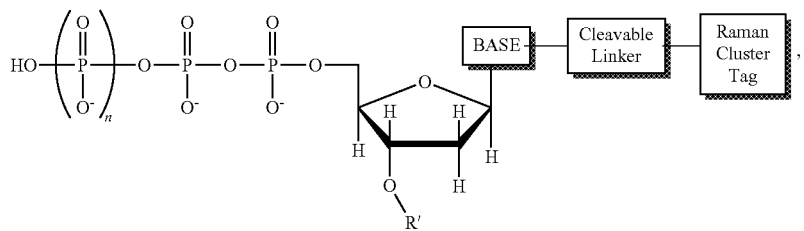

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein each analogue comprises a base which is different from the base of each of the remaining three analogues, and wherein when the cleavable linker of R' is cleaved it results in a 3'-OH, and wherein in step c) the cleavable linker attached to the base and the cleavable linker of R' are cleaved under identical circumstances.

The invention also provides a method for sequencing a single-stranded polynucleotide molecule, comprising a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate if the analogue is complementary to a nucleotide residue of the single-stranded polynucleotide which is immediately 5' to a nucleotide residue of the single-stranded polynucleotide hybridized to the 3' terminal nucleotide of the primer, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

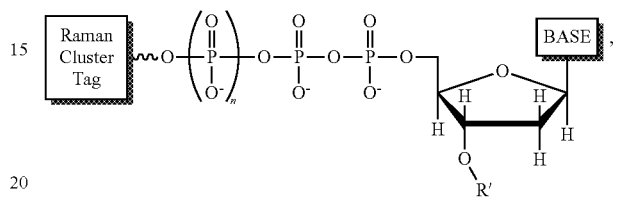

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tags comprise one or more Raman active groups, wherein the Raman spectroscopy peaks of the Raman cluster tags are predetermined, wherein the Raman spectroscopy peaks of the tags on each analogue are distinguishable from the Raman spectroscopy peaks of the tags on each of the remaining analogues, wherein each analogue comprises a base which is different from the base of each of the remaining three analogues, and wherein when the cleavable linker is cleaved it results in a 3'-OH;

b) determining the wavenumber of the Raman spectroscopy peaks of the Raman cluster tags of the analogue in the ternary complex, so as to thereby determine the identity of the nucleoside polyphosphate and the identity of the complementary nucleotide residue in the single-stranded polynucleotide;

c) cleaving the cleavable linker, so as to thereby create a 3'-OH, removing some or all of the non-catalytic metal ions, and adding catalytic metal ions, thereby permitting the nucleotide polymerase to cleave the terminal phosphate with the bound Raman cluster tag and catalyze the incorporation of the analogue into the primer so as to form a DNA extension product;

d) iteratively performing steps a) through c) for each nucleotide residue of the single-stranded polynucleotide to be sequenced so as to thereby determine the sequence of the single-stranded polynucleotide.

In another embodiment the nucleoside polyphosphate analogues have the structure:

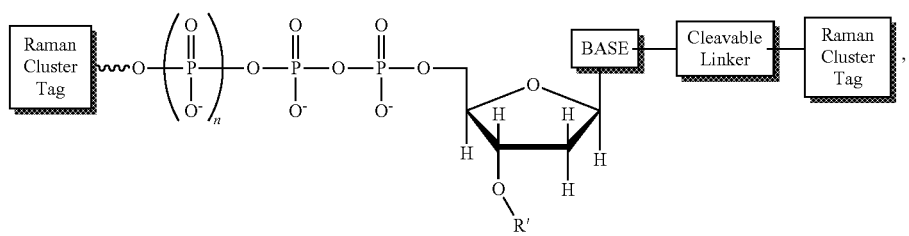

wherein base is any one of A, G, T, C, or U, or derivatives thereof, wherein n=0, 1, 2, 3, 4, 5, or 6, and R' comprises a cleavable linker and a Raman cluster tag, wherein R' is a 3' blocking group, wherein the Raman cluster tags comprise one or more Raman active groups, wherein the Raman spectroscopy peaks of the Raman cluster tags are predetermined, wherein the Raman spectroscopy peaks of the tags on each anawherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

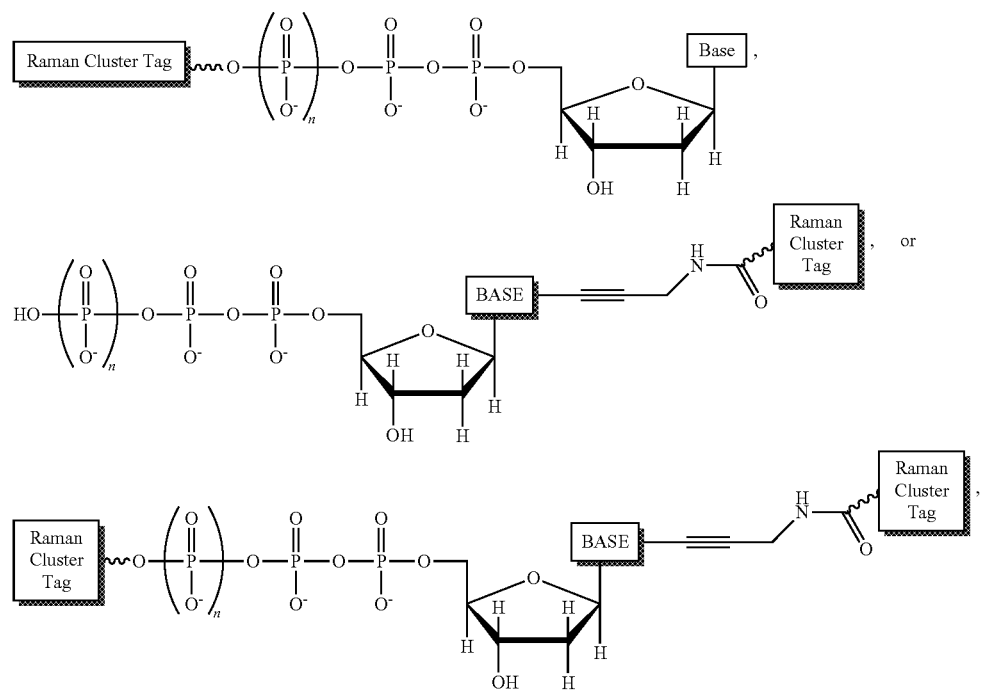

logue are distinguishable from the Raman spectroscopy peaks of the tags on each of the remaining analogues, wherein each analogue comprises a base which is different from the base of each of the remaining three analogues, and wherein when the cleavable linker of R' is cleaved it results in a 3'-OH, and wherein step c) also includes cleaving the cleavable linker attached to the base.

In another embodiment the cleavable linker of R' comprises any one of an allyl, alkyl, carbonyl, Sieber linkers, indole, disulfide, dithiomethyl, azidomethyl, nitrobenzyl, or any derivative thereof.

In another embodiment the cleavable linker of R' is cleavable with one or more of Pd(0), tetrabutylammonium, DTT, a triphosphine, peroxydisulphate, iodine, or any derivative thereof.

The invention also provides method for sequencing a single-stranded polynucleotide molecule, comprising:

a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein base is any one of A, G, T, C, or U, or derivatives thereof, wherein n=0, 1, 2, 3, 4, 5, or 6, wherein the Raman cluster tag comprises one or more Raman active groups, wherein the Raman spectroscopy peaks of the Raman cluster tag is predetermined, wherein the Raman spectroscopy peaks of the tag on each analogue are distinguishable from the Raman spectroscopy peaks of the tags on each of the remaining analogues, wherein each analogue comprises a base which is different from the base of each of the remaining three analogues;

b) determining the wavenumber of the Raman spectroscopy peaks of the Raman cluster tag of the analogue in the ternary complex, so as to thereby determine the identity of the nucleoside polyphosphate and the identity of the complementary nucleotide residue in the single-stranded polynucleotide;

c) contacting the ternary complex with four nucleotide reversible terminators thereby replacing the nucleoside polyphosphate analogue with a nucleotide reversible terminator with the proviso that the nucleotide reversible terminator is complementary to a nucleotide residue of the single-stranded polynucleotide which is immediately 5' to a nucleotide residue of the single-stranded polynucleotide hybridized to the 3' terminal nucleotide of the primer, wherein each nucleotide reversible terminator has the structure:

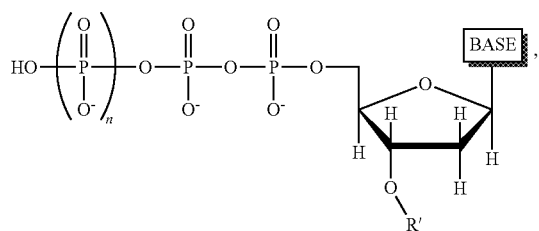

wherein base is any one of A, G, T, C, or U, or derivatives thereof, wherein n=0, 1, 2, 3, 4, 5, or 6, wherein R' comprises a cleavable 3' blocking group, wherein each nucleotide reversible terminator comprises a base which is different from the base of each of the remaining nucleotide reversible terminators;

d) removing some or all of the non-catalytic metal ions, and adding catalytic metal ions, thereby permitting the nucleotide polymerase to incorporate the nucleotide reversible terminator into the primer so as to form a DNA extension product;

e) cleaving the blocking group thereby resulting in a 3'-OH;

f) iteratively performing steps a) through e) for each nucleotide residue of the single-stranded polynucleotide to be sequenced so as to thereby determine the sequence of the single-stranded polynucleotide.

The invention also provides a method for sequencing a single-stranded polynucleotide molecule, comprising:

a) contacting the single-stranded polynucleotide having a primer hybridized to a portion thereof, with a nucleotide polymerase and four nucleoside polyphosphate analogues under conditions permitting the nucleotide polymerase to catalyze incorporation onto the primer of a nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, so as to form a DNA extension product, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

wherein base is any one of A, G, T, C, or U, or derivatives thereof, wherein n=0, 1, 2, 3, 4, 5, or 6, and wherein the Raman cluster tag comprises one or more Raman active groups, wherein the Raman spectroscopy peak of the Raman cluster tag is predetermined, wherein the Raman spectroscopy peak of the tag on each analogue is distinguishable from the Raman spectroscopy peak of the tag on each of the remaining analogues, wherein the presence of the Raman cluster tag prevents the polymerase from incorporating a subsequent nucleotide, wherein each analogue comprises a base which is different from the base of each of the remaining three analogues;

b) determining the wavenumber of the Raman spectroscopy peak of the incorporated nucleoside polyphosphate analogue Raman cluster tag, so as to thereby determine the identity of the incorporated nucleoside polyphosphate and the identity of the complementary nucleotide residue in the single-stranded polynucleotide;

c) cleaving the cleavable linker, thereby permitting the polymerase to incorporate a subsequent nucleoside polyphosphate analogue;

d) iteratively performing steps a) through c) for each nucleotide residue of the single-stranded polynucleotide to be sequenced so as to thereby determine the sequence of the single-stranded polynucleotide.

The invention also provides method for sequencing a single-stranded polynucleotide molecule, comprising:

a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate if the analogue is complementary to a nucleotide residue of the single-stranded polynucleotide which is immediately 5' to a nucleotide residue of the single-stranded polynucleotide hybridized to the 3' terminal nucleotide of the primer, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

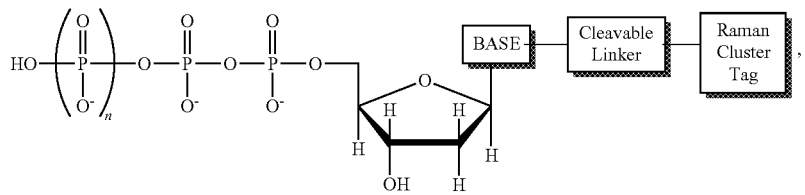

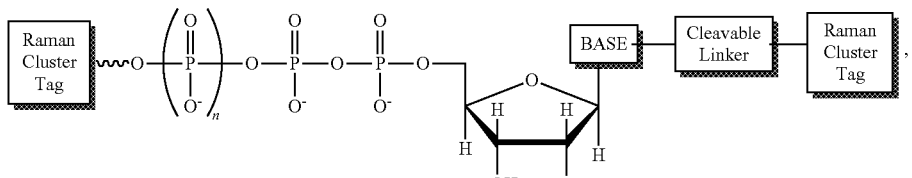

wherein base is any one of A, G, T, C, or U, or derivatives thereof, wherein n=0, 1, 2, 3, 4, 5, or 6, wherein the Raman cluster tags comprise one or more Raman active groups, wherein the Raman spectroscopy peaks of the Raman cluster tags are predetermined, wherein the Raman spectroscopy peaks of the tags on each analogue are distinguishable from the Raman spectroscopy peaks of the tags on each of the remaining analogues, wherein the presence of the Raman cluster tag linked to the base prevents the polymerase from incorporating a subsequent nucleoside polyphosphate, wherein each analogue comprises a base which is different from the base of each of the remaining three analogues, b) determining the wavenumber of the Raman spectroscopy peaks of the Raman cluster tags of the analogue in the ternary complex, so as to thereby determine the identity of the nucleoside polyphosphate and the identity of the complementary nucleotide residue in the single-stranded polynucleotide;

c) cleaving the cleavable linker so as to remove the tag attached to the base, removing some or all of the non-catalytic metal ions, adding one or more catalytic metal ions, thereby permitting the nucleotide polymerase to cleave the terminal phosphate with the bound Raman cluster tag and catalyze the incorporation of the analogue into the primer so as to form a DNA extension product;

d) iteratively performing steps a) through c) for each nucleotide residue of the single-stranded polynucleotide to be sequenced so as to thereby determine the sequence of the single-stranded polynucleotide.

The invention also provides a method for sequencing a single-stranded polynucleotide molecule, comprising:

a) contacting the single-stranded polynucleotide having a primer hybridized to a portion thereof, with a nucleotide polymerase, four nucleoside polyphosphate analogues, and one or more non-catalytic metal ions under conditions permitting the nucleotide polymerase to form a ternary complex with the single-stranded polynucleotide, primer, and the nucleoside polyphosphate analogue if the analogue is complementary to a nucleotide residue of the single-stranded polynucleotide which is immediately 5' to a nucleotide residue of the single-stranded polynucleotide hybridized to the 3' terminal nucleotide of the primer, wherein the polymerase has one or more embedded, derivatized, attached, and/or conjugated noble metal nanoparticles thereby creating a region or regions of enhanced sensitivity for surface enhanced Raman spectroscopy within or adjacent to the polymerase, wherein the nucleoside polyphosphate analogues have the structure:

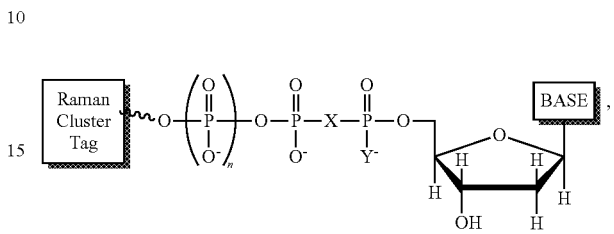

wherein base is any one of A, G, T, C, or U, or derivatives thereof, wherein n=0, 1, 2, 3, 4, 5, or 6, wherein the Raman Cluster Tag comprises Raman active groups, wherein X is any one of $CH_2$, NH, CHF—, or $CF_2$, and wherein Y is any one of O, S, or $BH_3$, wherein X and/or Y prevent the nucleotide polymerase from cleaving the bond between the $\alpha$ and $\beta$ phosphates, wherein the Raman spectroscopy peaks of the Raman cluster tag is predetermined, wherein the Raman spectroscopy peaks of the tag on each analogue are distinguishable from the Raman spectroscopy peaks of the tags on each of the remaining analogues, wherein each analogue comprises a base which is different from the base of each of the remaining three analogues;

b) determining the wavenumber of the Raman spectroscopy peaks of the Raman cluster tag of the analogue in the ternary complex, so as to thereby determine the identity of the nucleoside polyphosphate and the identity of the complementary nucleotide residue in the single-stranded polynucleotide;

c) contacting the ternary complex with four nucleotide reversible thereby replacing the nucleoside polyphosphate analogue with a nucleotide reversible terminator with the proviso that the nucleotide reversible terminator is complementary to a nucleotide residue of the single-stranded polynucleotide which is immediately 5' to a nucleotide residue of the single-stranded polynucleotide hybridized to the 3' terminal nucleotide of the primer, wherein the nucleotide reversible terminators have the structure:

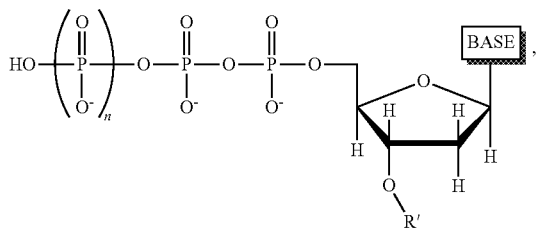

wherein base is any one of A, G, T, C, or U, or derivatives thereof, wherein n=0, 1, 2, 3, 4, 5, or 6, wherein R' comprises a cleavable 3' blocking group, wherein each nucleotide reversible terminator comprises a base which is different from the base of each of the remaining nucleotide reversible terminators;

d) removing some or all of the non-catalytic metal ions, and adding catalytic metal ions, thereby permitting the nucleotide polymerase to incorporate the nucleotide reversible terminator into the primer so as to form a DNA extension product;
e) cleaving the blocking group thereby resulting in a 3'-OH;
f) iteratively performing steps a) through e) for each nucleotide residue of the single-stranded polynucleotide to be sequenced so as to thereby determine the sequence of the single-stranded polynucleotide.

In another embodiment wherein the cleavable linker attached to the base comprises any one of an allyl, alkyl, carbonyl, Sieber linkers, indole, disulfide, dithiomethyl, azidomethyl, nitrobenzyl, or any derivative thereof.

In another embodiment the cleavable linker attached to the base is cleavable with one or more of Pd(0), tetrabutylammonium, DTT, a triphosphine, peroxydisulphate, iodine, or any derivative thereof.

In another embodiment the non-catalytic metal ions are one or more of $Sr^{++}$ and $Ca^{++}$. In another embodiment the catalytic metal ions are one or more of $Mg^{++}$ or $Mn^{++}$.

In another embodiment the Raman active groups are one or more of $—N=N^+=N^-$, $—C\equiv CH$, $—C\equiv CD$, $—C\equiv CH_3$ and $—C\equiv N$. In another embodiment the Raman active groups have a Raman spectroscopy peak with a wave number from $2100\ cm^{-1}$ to $2300\ cm^{-1}$.

In another embodiment the primer is attached to a surface or other substrate. In another embodiment the single-stranded polynucleotide comprises an adapter that is a predetermined nucleotide sequence, and wherein the primer comprises a complementary nucleotide sequence.

In another embodiment prior to step a) the single-stranded polynucleotide is Polymerase Chain Reaction (PCR)-amplified so as to thereby produce a plurality of copies which are attached to a bead, and wherein the beads with the attached plurality of single-stranded polynucleotide.

In another embodiment there are a plurality of polymerases and primers so as to thereby permit simultaneous parallel sequencing of the single-stranded polynucleotide copies.

In another embodiment the polymerase or polymerases are attached to a surface.

In another embodiment the noble metal nanoparticles are silver and/or gold nanoparticles.

In another embodiment the metal nanoparticles of the polymerase or polymerases are between 3 nm and 10 nm. In another embodiment the polymerase or polymerases have 2, 3, 4, or 5 metal nanoparticles. In another embodiment the metal nanoparticles of the polymerase or polymerases are attached and/or conjugated to the polymerase 1 nm-3 nm from the active site of the polymerase. In another embodiment the metal nanoparticles of the polymerase or polymerases are attached and/or conjugated to the polymerase or polymerases 1 nm-3 nm from the active site of the polymerase, thereby creating a region of enhanced sensitivity for surface enhanced Raman spectroscopy (SERS) at the active site. In another embodiment the metal nanoparticles are attached and/or conjugated to the polymerase such that when a nucleoside and/or nucleotide are in the active site of the polymerase, and wherein the nucleoside and/or nucleotide are tagged with a Raman active molecule, the metal nanoparticles are located 1 nm-3 nm from the Raman active molecule. In another embodiment the attached and/or conjugated metal nanoparticles of the polymerase create a region of enhanced sensitivity for surface enhanced Raman spectroscopy (SERS) at the location of the Raman active molecule.

In certain embodiments of the invention, the tag comprises a plurality of identical Raman-scattering moieties. In other embodiments, the tag comprises a plurality of different Raman-scattering moieties.

In certain specific embodiments, the tag comprises 3, 9, or 27 Raman-scattering moieties.

In an embodiment, the plurality of Raman-scattering moieties forms a linear tag. In another embodiment, the plurality of Raman-scattering moieties forms a non-linear tag. In a preferred embodiment, the non-linear tag is a dendrimer tag.

In an embodiment, the tag has a Raman spectroscopy peak with wavenumber from $2125\ cm^{-1}$ to $2260\ cm^{-1}$.

For the foregoing embodiments, each embodiment disclosed herein is contemplated as being applicable to each of the other disclosed embodiments. In addition, the elements recited in the compound embodiments can be used in the composition and method embodiments described herein and vice versa.

As used herein, and unless stated otherwise, each of the following terms shall have the definition set forth below.
A—Adenine;
C—Cytosine;
G—Guanine;
T—Thymine;
U—Uracil;
DNA—Deoxyribonucleic acid;
RNA—Ribonucleic acid;

"Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Substrate" or "Surface" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analog capable of forming a phosphodiester bond.

As used herein, unless otherwise specified, a base which is "different from" another base or a recited list of bases shall mean that the base has a different structure from the other base or bases. For example, a base that is "different from" adenine, thymine, and cytosine would include a base that is guanine or a base that is uracil.

As used herein, unless otherwise specified, a tag moiety which is different from the tag moiety of a referenced molecule means that the tag moiety has a different chemical structure from the chemical structure of the other/referenced tag moiety.

In some embodiments of the invention, vibrational spectroscopy is used to detect the presence of incorporated nucleotide analogs. Vibrational spectroscopy is a spectrographic analysis where the sample is illuminated with incident radiation in order to excite molecular vibrations. Vibrational excitation, caused by molecules of the sample absorbing, reflecting or scattering a particular discrete amount of energy, is detected and can be measured. The two major types of vibrational spectroscopy are infrared (usually FTIR) and Raman. If FTIR is employed, then the IR spectra of the nucleotide analogs are measured. If Raman is employed, then the Raman spectra of the nucleotide analogs is measured (for example of the nucleotide analogs and in the methods described herein).

In certain embodiments, the polymerase, single-stranded polynucleotide, RNA, or primer is bound to a solid substrate via 1,3-dipolar azide-alkyne cycloaddition chemistry. In an embodiment the polymerase, DNA, RNA, or primer, is bound to the solid substrate via a polyethylene glycol molecule. In an embodiment the polymerase, DNA, RNA, primer, or probe is alkyne-labeled. In an embodiment the polymerase, DNA, RNA, primer, or probe is bound to the solid substrate via a polyethylene glycol molecule and the solid substrate is azide-functionalized. In an embodiment the polymerase, DNA, RNA, or primer, is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded polynucleotide. In an embodiment the RNA is single-stranded RNA.

In other embodiments, the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In one embodiment, the surface or substrate is a SERS-prepared surface or substrate designed specifically for detection of a label nucleotide. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may include DNA functionalized sites, and may have a gap size range from 50 nm to 1 nm. In another embodiment, a nucleotide polymerase is immobilized within the gap.

In another embodiment the nucleotide polymerase SERS-prepared and designed specifically for detection of a labeled nucleotide and/or nucleoside. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may have a gap size range from 12 nm to 1 nm. In another embodiment, a nucleotide polymerase is immobilized within on a surface, substrate, or nanoplasmonic antenna on a surface.

In another embodiment, the surface comprises a DNA origami scaffold or an array of DNA origami scaffolds. It is also contemplated that the DNA origami scaffold further comprising a primer molecules positioned between Au and Ag nanoparticles and nanorods located at specified binding sites.

In a further embodiment, the surface comprises plasmonic crystals or an array of plasmonic structures. For example, the plasmonic structures may be periodic TiO—Au—TiO structures.

In various embodiments the polymerase, nucleic acid samples, DNA, RNA, primer, or probe are separated in discrete compartments, wells or depressions on a surface.

In this invention methods are provided wherein about 1000 or fewer copies of the polymerase, nucleic acid sample, DNA, RNA, or primer are bound to the substrate. This invention also provides the instant methods wherein $2 \times 10^7$, $1 \times 10^7$, $1 \times 10^6$ or $1 \times 10^4$ or fewer copies of the polymerase, nucleic acid sample, DNA, RNA, or primer are bound to the substrate or surface.

In some embodiments, the immobilized polymerase, nucleic acid sample, DNA, RNA, or primer, is immobilized at a high density. This invention also provides the instant methods wherein over or up to $1 \times 10^7$, $1 \times 10^8$, $1 \times 10^9$ copies of the polymerase, nucleic acid sample, DNA, RNA, or primer are bound to the substrate or surface.

In other embodiments of the methods and/or compositions of this invention, the DNA is single-stranded. In other embodiments of the methods or of the compositions described herein, the single-stranded polynucleotide is replaced with an RNA that is single-stranded.

In certain embodiments, UV light is used to photochemically cleave the photochemically cleavable linkers and moieties. In an embodiment, the photocleavable linker is a 2-nitrobenzyl moiety. In an embodiment of the processes and methods described herein monochromatic light is used to irradiate Raman-label-containing nucleotide analogs (e.g. incorporated into a primer or DNA extension product) so as to elicit a signal measurable by Raman spectroscopy. In one such embodiment, the laser is a 532 nm, 633 nm, or 785 nm laser. In another such embodiment, near infra-red light is used to irradiate Raman-label-containing nucleotide analogs. In certain embodiments of the processes and methods of this invention near infra-red light is used to irradiate Raman-label-containing polynucleotide analogs.

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

Because of well-understood base-pairing rules, determining the wavenumber of the Raman spectroscopy peak of a dNTP analog incorporated into a primer or DNA extension product, and thereby the identity of the dNTP analog that was incorporated, permits identification of the complementary nucleotide residue in the single-stranded polynucleotide that the primer or DNA extension product is hybridized to. Thus, if the dNTP analog that was incorporated has a unique wavenumber in the Raman spectroscopy peak identifying it as comprising an adenine, a thymine, a cytosine, or a guanine, then the complementary nucleotide residue in the single-stranded polynucleotide is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the dNTP analog that was incorporated comprises an adenine, a uracil, a cytosine, or a guanine, then the complementary nucleotide residue in the single-stranded RNA is identified as a uracil, an adenine, a guanine or a cytosine, respectively.

Incorporation into an oligonucleotide or polynucleotide (such as a primer or DNA extension strand) of a nucleotide and/or nucleoside analogue means the formation of a phosphodiester bond between the 3' carbon atom of the 3' terminal nucleotide residue of the polynucleotide and the 5' carbon atom of the dNTP analog resulting in the loss of pyrophosphate from the dNTP analog.

A Raman spectroscopy system, as can be used in the methods described herein, typically comprises an excitation source (such as a laser, including a laser diode in appropriate configuration, or two or more lasers), a sample illumination system and light collection optics, a wavelength selector (such as a filter or spectrophotometer), and a detection apparatus (such as a CCD, a photodiode array, or a photomultiplier). Interference (notch) filters with cut-off spectral range of $\pm 80\text{-}120\ cm^{-1}$ from the laser line can be used for stray light elimination. Holographic gratings can be used. Double and triple spectrometers allow taking Raman spectra without use of notch filters. Photodiode Arrays (PDA) or a Charge-Coupled Devices (CCD) can be used to detect Raman scattered light.

In an embodiment, surface enhanced Raman spectroscopy (SERS) is used which employs a surface treated with one or more of certain metals known in the art to cause SERS effects. In an embodiment the surface is a surface to which the polymerase, polynucleotide, single-stranded polynucleotide, single-stranded DNA polynucleotide, single-stranded RNA, primer, DNA extension strand, or oligonucleotide probe of the methods described herein is attached. Many suitable metals are known in the art. In an embodiment the surface is electrochemically etched silver or treated with/comprises silver and/or gold colloids with average particle size below 20 nm. The wavenumber of the Raman spectroscopy peak of an entity is identified by irradiating the entity with the excitation source, such as a laser, and collecting the resulting Raman spectrum using a detection apparatus. The wavenumber of the Raman spectroscopy peak is determined from the Raman spectrum. In an embodiment, the spectrum measured is from $2000\ cm^{-1}$ to $2300\ cm^{-1}$ and the wavenumber of the Raman spectroscopy peak is the peak wavenumber within that spectrum. In an embodiment the spectrum measured is a sub-range of $2000\ cm^{-1}$ to $2300\ cm^{-1}$ and the Raman spectroscopy peak wavenumber is the peak wavenumber within that spectrum sub-range.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n–1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Disclosed herein are novel methods of nucleic acid sequencing that combine the advantages of sequencing by synthesis (SBS) in terms of sequencing accuracy with the power of SERS to describe a number of approaches for nucleic acid sequencing with both ensembles of identical template molecules and single template molecules. Further disclosed are related methods for real-time single molecule sequencing by synthesis.

Figure 2:
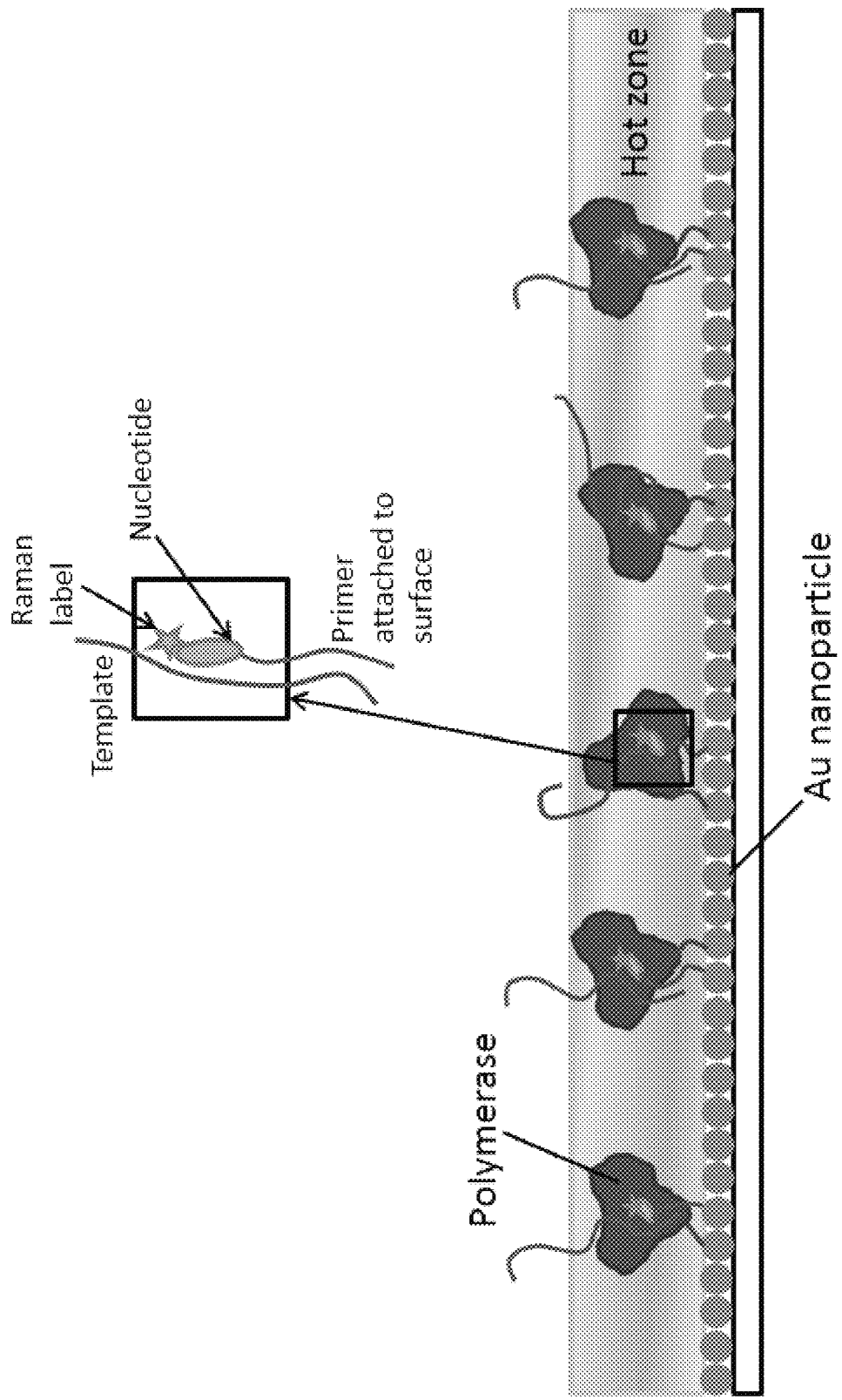
FIG. 2: Schematic of set-up for single molecule SBS on SERS substrate with primers bound to surface. Gold nanoparticles are distributed on a glass slide. Primer DNA is chemically attached to the gold surface where it is maintained in a constant position. Following binding of template, polymerase and nucleotides bearing single Raman active groups (RAGs) or RAG clusters, the rest of the procedure is carried out as indicated in the legend to FIG. 1. The tether on the polymerase maintains its active site within the hot zone.
Figure 3:
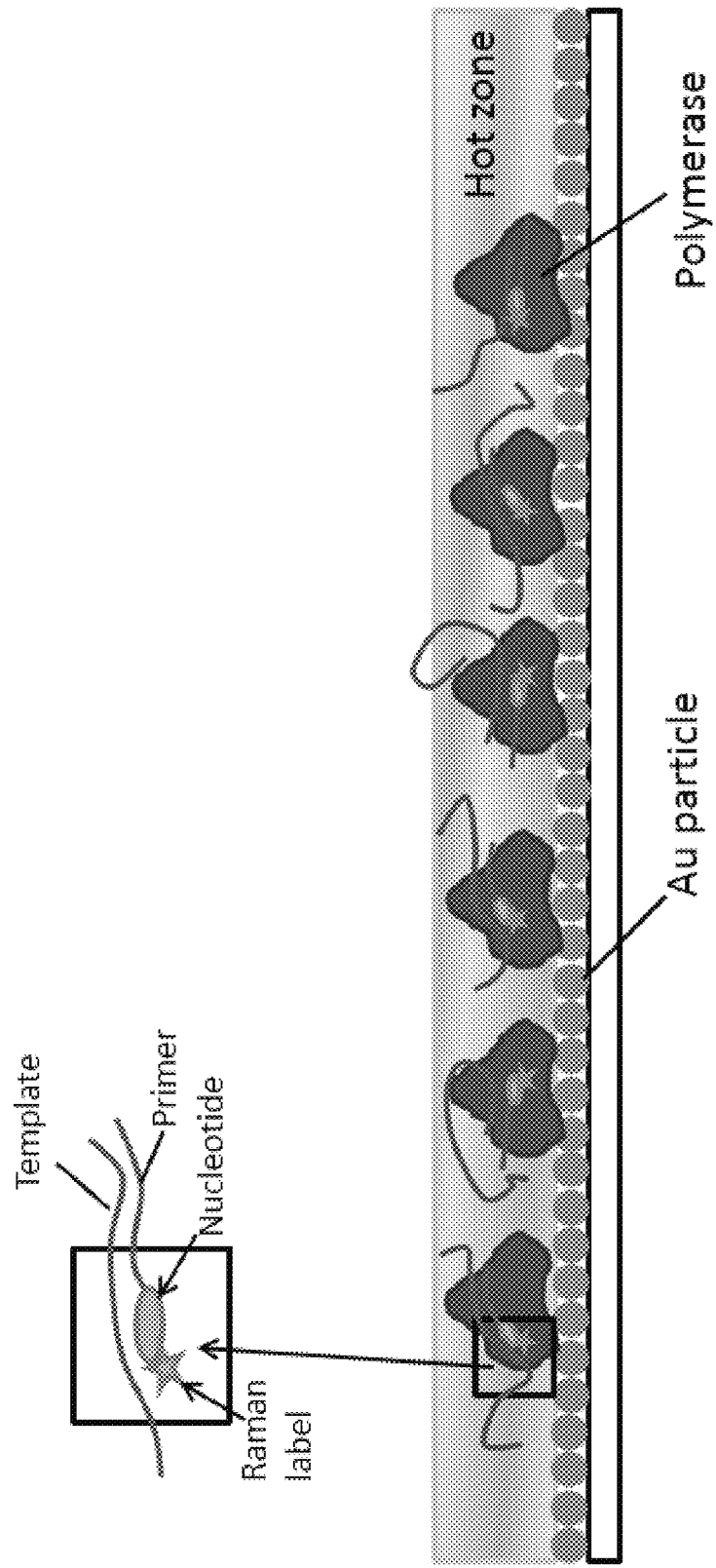
FIG. 3: Schematic of set-up for single molecule real-time SES on SERS substrate with polymerase bound to surface. Gold nanoparticles are distributed on a glass slide. Polymerase is directly chemically bound to the gold particles. DNA and primers are added, along with nucleotides bearing single Raman active groups (RAGs) or RAG clusters. Each of the four nucleotides bears a different RAG or RAG cluster. Constant monitoring under a Raman microscope allows sequence determination in real time.
Figure 5:
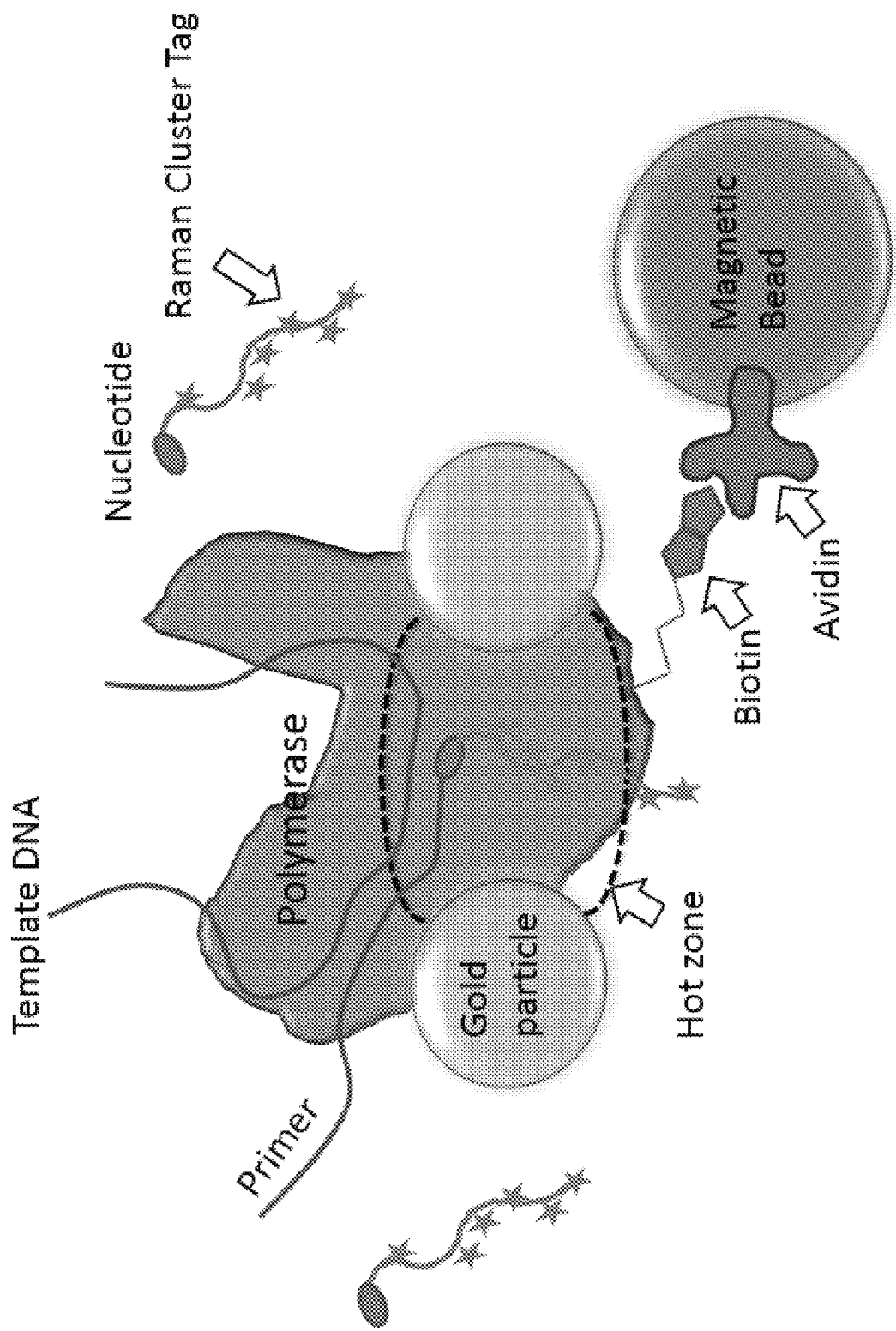
FIG. 5: Single molecule real-time Raman SBS with gold particles attached to polymerase, Raman active groups attached to nucleotide, and polymerase bound to magnetic beads. Gold particles conjugated to polymerase produce a hot zone within the enzyme. The biotin on the polymerase permits attachment to streptavidin beads allowing washing and maintaining the reaction in a specific localization for Raman detection over many sequencing cycles. Alternatively, the DNA may be directly attached to the surface of the reaction chamber. Four different nucleotides, each with different Raman cluster labels are added, along with template and primer. Nucleotides in solution are outside the hot zone and will not elicit a signal. Raman detection is carried out in real time.
Figure 6:
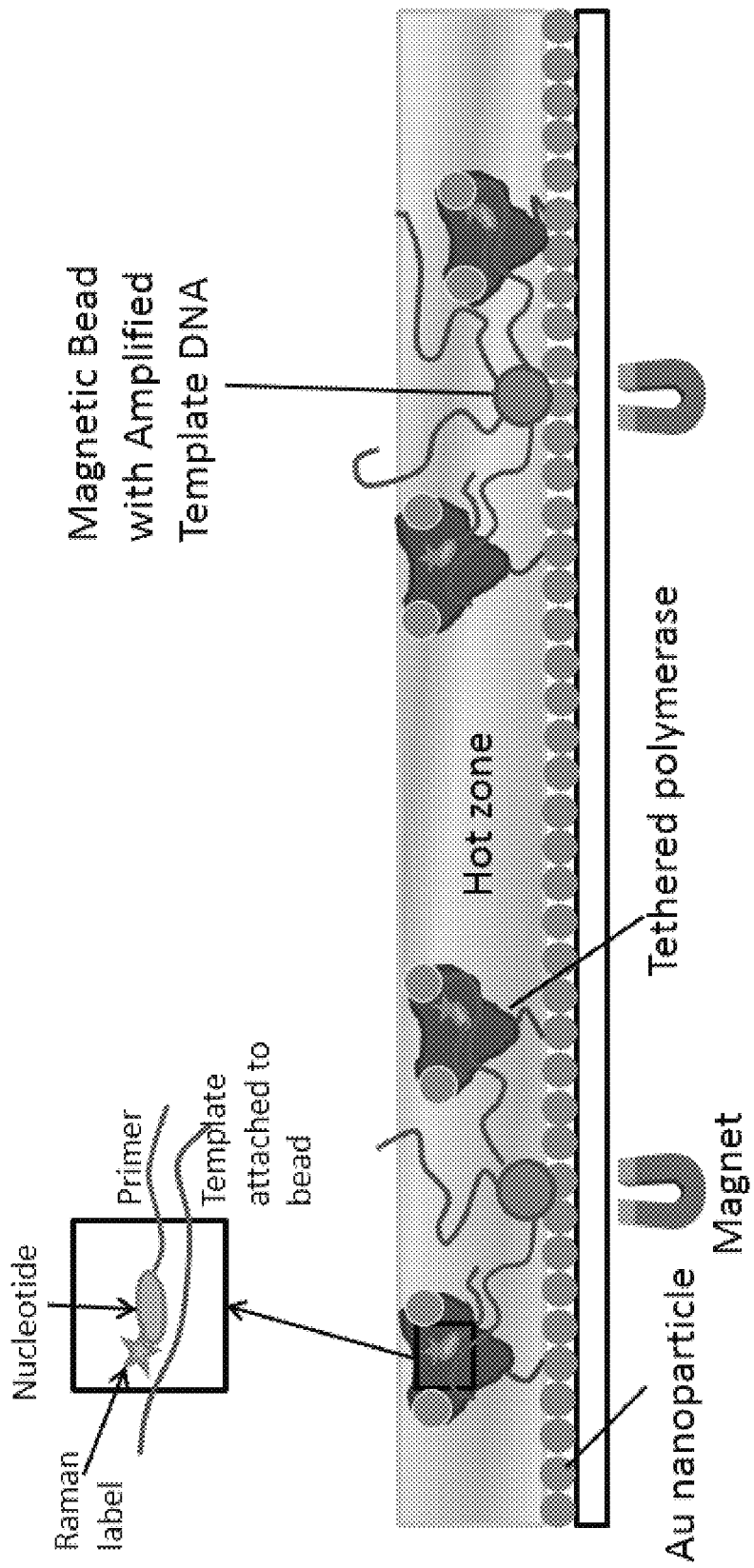
FIG. 6: Schematic of hybrid set-up for ensemble SBS using both a SERS substrate and gold nanoparticles attached to the polymerase. Gold nanoparticles are distributed on a glass slide. DNA is amplified on magnetic beads by emulsion PCR or equivalent approach and attracted to the gold surface by a magnetic field. The surface is derivatized with a large excess of tethered polymerases, which in this variant are decorated with gold nanoparticles. This keeps the enzyme's active site within the SERS hot zone and in addition produces a hot spot within the polymerase. The use of the magnetic beads permits washing and maintains the reactions in a particular location for multiple sequencing cycles. The solution contains primer and nucleotides bearing single Raman active groups (RAGs) or RAG clusters. After the first template complementary nucleotide is bound in the ternary complex where it is held either by the use of non-catalytic metals, unincorporable nucleotides, reversible terminators, or combinations of these, see Examples 1-10), the Raman signal is detected, and the block to incorporation of the current or subsequent nucleotide is removed, the next round is initiated.
Figure 7:
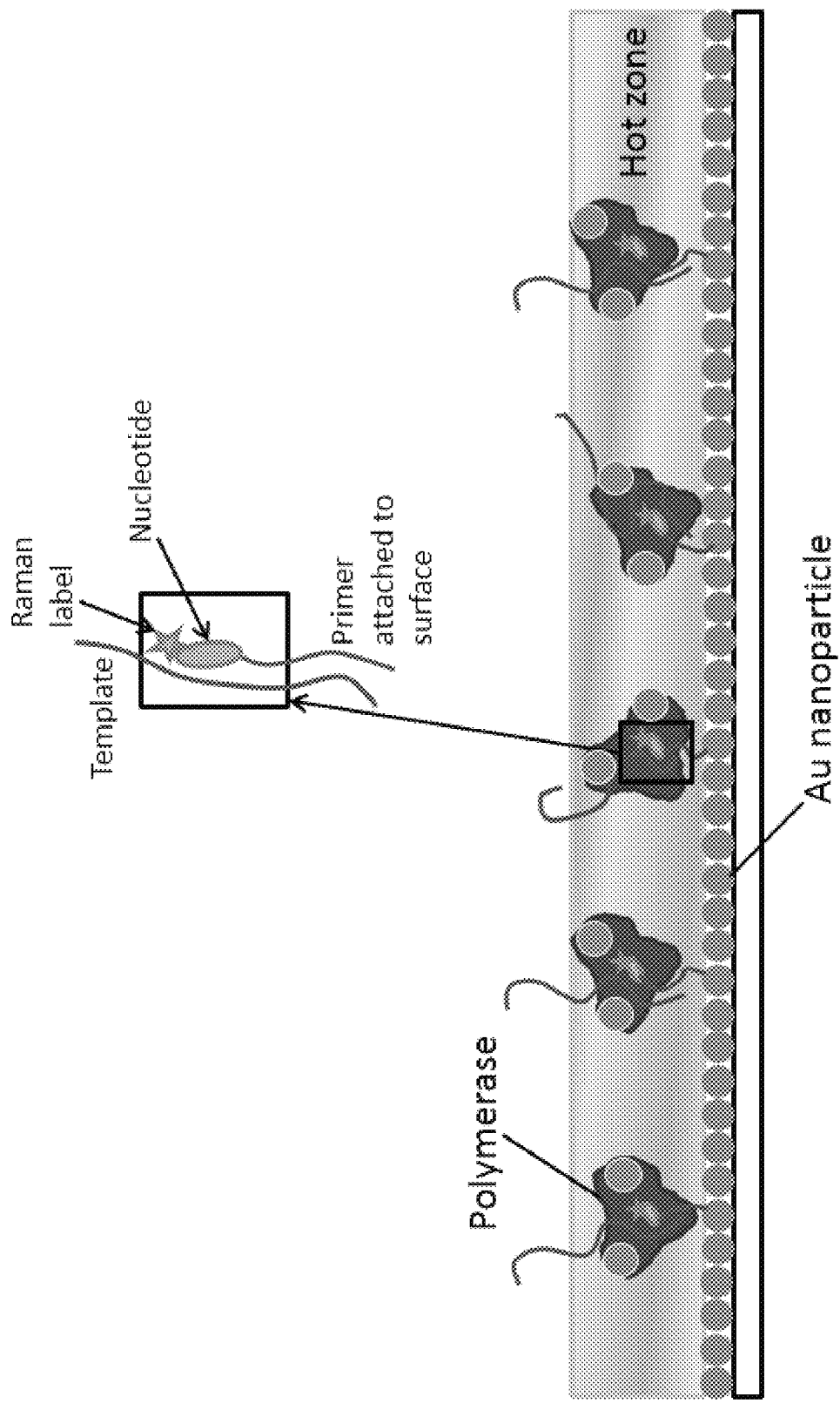
FIG. 7: Schematic of hybrid set-up for single molecule SBS using both a SERS substrate and gold nanoparticles attached to the polymerase. Gold nanoparticles are distributed on a glass slide. Primer DNA is chemically attached to the gold surface where it is maintained in a constant position. Following binding of template, polymerase decorated with gold nanoparticles and nucleotides bearing single Raman active groups (RAGs) or RAG clusters, the rest of the procedure is carried out as indicated in the legend to Figure S. The bound primer maintains the active site of the polymerase within the SERS hot zone, while the gold nanoparticles attached to the polymerase produce an additional hot spot directly within the enzyme.
Figure 9:
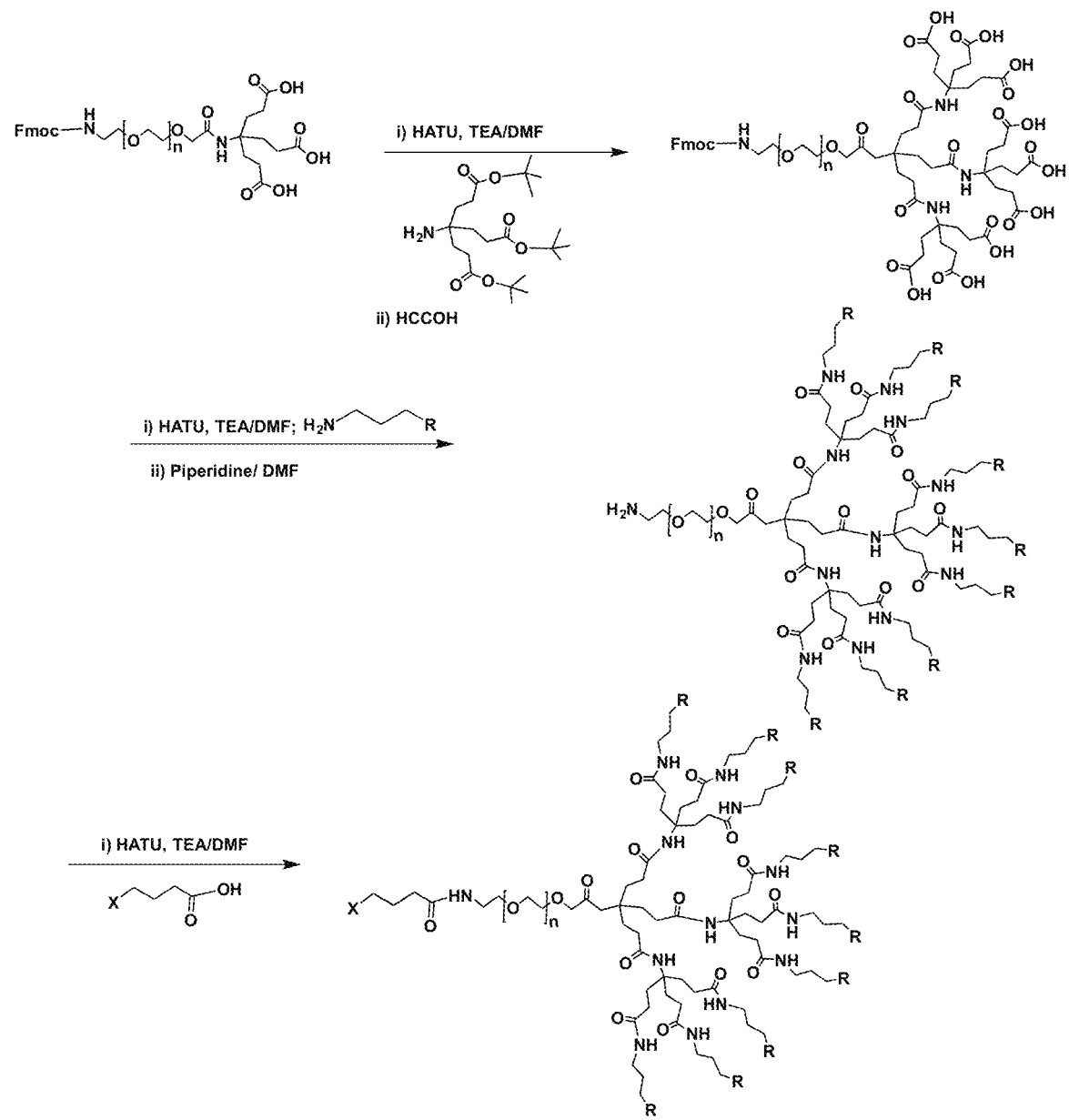
FIG. 9: Synthetic scheme for a dendrimer compound carrying 9 Raman active signal groups. X refers to any functional group which can be attached to the nucleotide.

The novel sequencing methods herein disclosed include (1) Raman-based sequencing by synthesis (SBS) on a surface-enhanced Raman substrate studded with noble metal nanoparticles which create a Raman hot zone above the gold layer generating SERS (FIGS. 1-3), (2) one in which noble metal nanoparticles are directly attached to the polymerase resulting in a Raman hot zone within the enzyme itself (FIGS. 4 and 5), and (3) a hybrid method in which noble metal nanoparticles are attached to both the substrate and the polymerase (FIGS. 6 and 7). In all cases, Raman active groups present on nucleotides and polymerase localized near or within SERS hot spots are key features of the invention disclosed herein. (These Raman groups are generally shown in the following examples as azido groups (—N=N$^+$=N$^-$), but can be any chemical moiety or combination of chemical moieties (—C≡CH, —C≡CD, —C≡C-alkyl, —C≡C-aryl and —C≡N) that produce a signal in a particular portion of the Raman spectrum where natural nucleotides, amino acids, nucleic acids and proteins do not. These Raman groups may be positioned on a nucleotide 2'- or 3'-OH group in some cases so that the resulting nucleotides are reversible terminators. Raman tags can also be attached to the terminal phosphate, or attached via cleavable or uncleavable bonds to the base of the nucleotides. The Raman active groups may be present singly or more typically in clusters such as dendrimers or bound to polynucleotide chains (FIGS. 8 and 9), the latter especially when they are linked directly to the terminal phosphate or the base. The nucleotides in turn may be ribonucleoside or deoxyribonucleoside triphosphates or polyphosphates, dNTPs, dNPPs, NTPs or NPPs, where N can indicate adenine, thymine, guanine, cytosine, uracil or common variants of these bases well known in the sequencing field. These nucleotides may be further modified with 3'-OH blocking groups or with uncleavable bonds between the α and β phosphates. The Raman SBS strategies may include detection of an ensemble of molecules or single molecules, and in a couple of cases are designed for real-time single molecule sequencing.

Finally, these methods can be "single color" in which a single Raman active group is used and these nucleotides are added sequentially one by one in the course of the sequencing reaction, or "four color" in which four different Raman active groups (RAGS) or combinations of RAGs are attached to each of the four nucleotides (e.g., A, C, G and T) which are added together in the reaction and can produce four distinct signatures. Approaches for carrying out Raman SBS utilizing most of the varieties of hot spot localization, types of nucleotides, positioning of Raman active chemical groups, ensemble or single molecule detection, number of RAGs and other features indicated above will be presented in the following section.

General Category 1: Raman-Based SBS with a SERS Substrate.

In this design (see FIGS. 1-3), a surface enhanced Raman substrate is first created by noble metal nanoparticles on a glass or other substrate. The glass surface may be derivatized with a sulfhydryl or equivalent chemical group to allow covalent binding of the noble metal particles. A wide variety of methods for generating clusters of noble metal particles for SERS are available. As one illustrative example, the colloidal gold particles may themselves be derivatized with chemical groups to permit self-assembly into a mono- or multilayer on the glass surface. Gaps of 1-5 nm between the noble metal particles are to serve as SERS hotspots, and a region of up to 10 nm above the noble metal surface forms a discontinuous hot zone (Chen et al 2015). The Raman signal enhancement at the hotspots may be as high as $10^8$-fold or more compared to the unenhanced Raman signal. Even at a distance of 5-10 nm from the hotspots, the hot zone, the signal enhancement should still be substantial, $\sim 10^6$-fold. As shown in FIG. 1, groups of templates are amplified onto a solid support by emulsion PCR on beads (Dressman et al 2003, Shendure et al 2005), by PCR-based bridge amplification (Bentley et al 2008), or by an isothermal amplification using walking strand displacement (Ma et al 2013) for ensemble sequencing. In this case, it is also necessary to tether the polymerase to the surface, preferably by a linker of up to 2 nm in length to keep the polymerase active center within the SERS hot zone. Alternatively (FIG. 2), the primers are immobilized to a solid support following the procedure of Harris et al (2008) in preparation for single molecule sequencing, although in this case they are modified so as to bind to the noble metal surface where the polymerase would be tethered as well; this keeps the polymerase active center within the hot zone. Finally (FIG. 3), just the polymerase can be directly attached to the noble metal surface following procedures in the literature for substrate attachment (Eid et al 2009, Korlach et al 2010) for real-time single molecule sequencing. Herein disclosed are 11 experiments under General Category 1. Experiments 1-10 will most use the ensemble setup shown in FIG. 1 in which the magnetic beads bearing amplified DNA and primers are attracted to the gold surface and nucleotides and polymerase are present in the solution but may also use the single molecule setup in FIG. 2 in which the primer is attached to the surface. In these experiments, RAG clusters are needed for single molecule sequencing. Experiment 11 (real-time single molecule sequencing) uses the set-up in FIG. 3 in which the polymerase is directly attached to the gold particles. Though not disclosed in the following experiments, RAGs (single or small clusters) can also be attached at the 2' position of the sugar.

Figure 10:
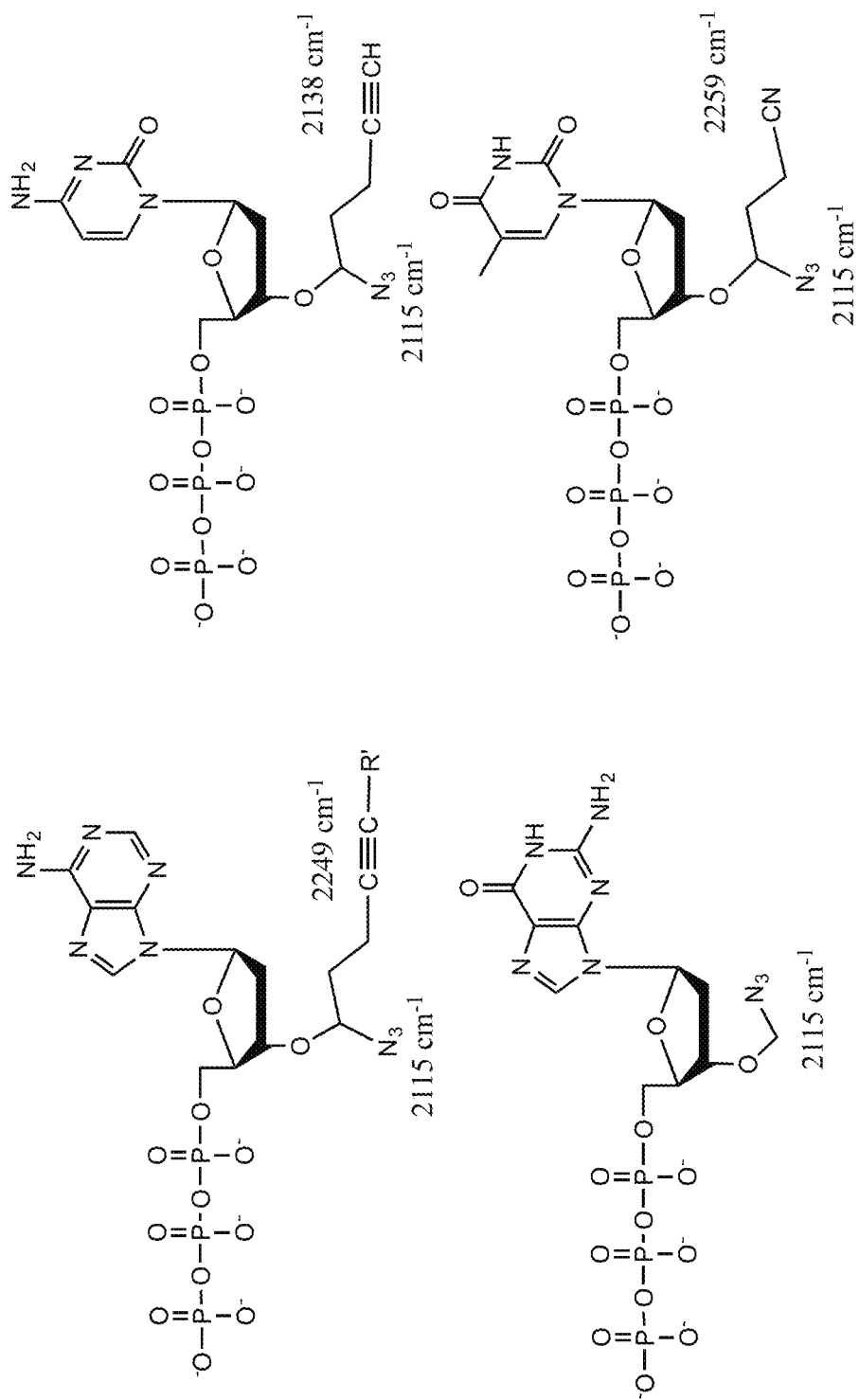
FIG. 10: Structures of 3'-O reversibly blocked dNTPs for Raman sequencing. The 3'-blocking groups also serve as Raman tags which will produce distinguishable combinations of Raman signals.

Experiment 1: Ensemble SBS in which the Raman Active Group Also Serves as the 3'-Blocking Group Here, a single moiety of one of the Raman active groups is attached to the 3'-OH of the sugar of the nucleotide as shown in FIG. 10, which depicts four examples. In the first step, beads bearing emulsion PCR-amplified (clonal) DNA molecules bearing adapters and adapter-based primers are deposited on the SERS surface, and the first of four 3'-azidomethyl dNTPs (NRTs), e.g., 3'-blocked dATP. Any small-sized Sepharose bead may be used for the emulsion PCR; paramagnetic beads might be particularly useful when a magnet is placed below the slide, to collect the maximum number of template-bearing beads near the polymerase molecules, which are present in excess and tethered to the gold substrate, as well as to keep them in place during washing and replacement of reagents. The azidomethyl group not only blocks the 3'-hydroxyl group, preventing additional incorporations beyond the initial nucleotide, but also serves as a Raman active group producing peaks with a wave number in the region of the Raman spectrum (2100-2300 cm$^{-1}$) where proteins and DNA do not. After sufficient time to collect the SERS signal, the slide is treated with TCEP to restore the 3'-hydroxyl group, washed, and the second NRT, e.g., 3'-blocked dCTP, is added. In the simplest scheme, nucleotides are added one at a time, all "labeled" with the same azidomethyl group. Because these nucleotides are reversible terminators, there are no difficulties in decoding the precise length of homopolymeric stretches of the same nucleotide. With potentially hundreds of millions or even billions of sites of active DNA-bound polymerases, this technique may allow human genome scale sequencing from a single chip so long as the region around each bead is monitored independently. In the case of single molecule sequencing, instead of using templates amplified on beads, templates are hybridized with primers bound to the gold surface.

In the above scenario, only a single Raman-active group is used. This necessitates adding NRTs one by one. However in addition to the azido (—N=N$^+$=N$^-$) moiety, other small chemical groups that produce distinct signals in the DNA/ protein-free region of the Raman spectrum such as —C≡CH, —C≡CD, —C≡C-alkyl, —C≡C-aryl and —C≡N, are also capable of being attached to the sugar or bases of the four nucleotides, singly or in combination with the 3'-azidomethyl group (FIG. 10). Thus the equivalent of four-color fluorescent SBS (Ju et al 2006) can is carried out where all four modified NRTs are added at the same time and the resulting Raman signals are base-specific.

Figure 11:
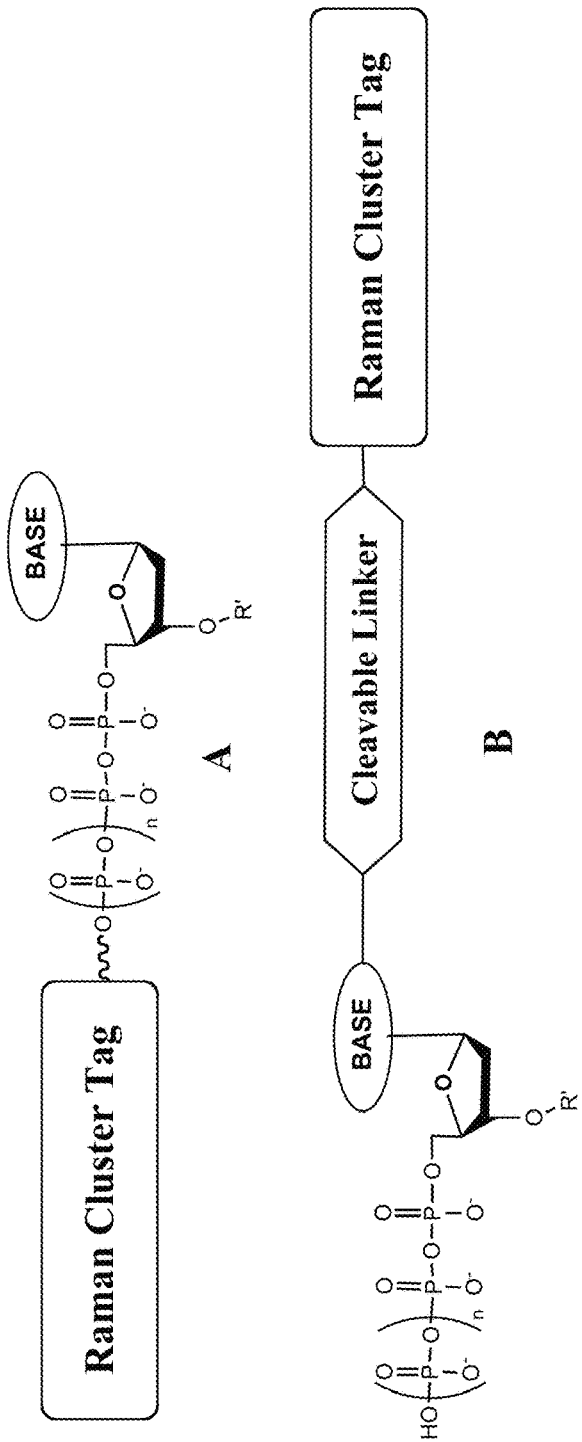
FIG. 11: Raman cluster (RC) labeled 3'-O reversibly blocked nucleotides. RC is attached to terminal phosphate (A) or attached to the base via a cleavable linker (B).
Figure 12:
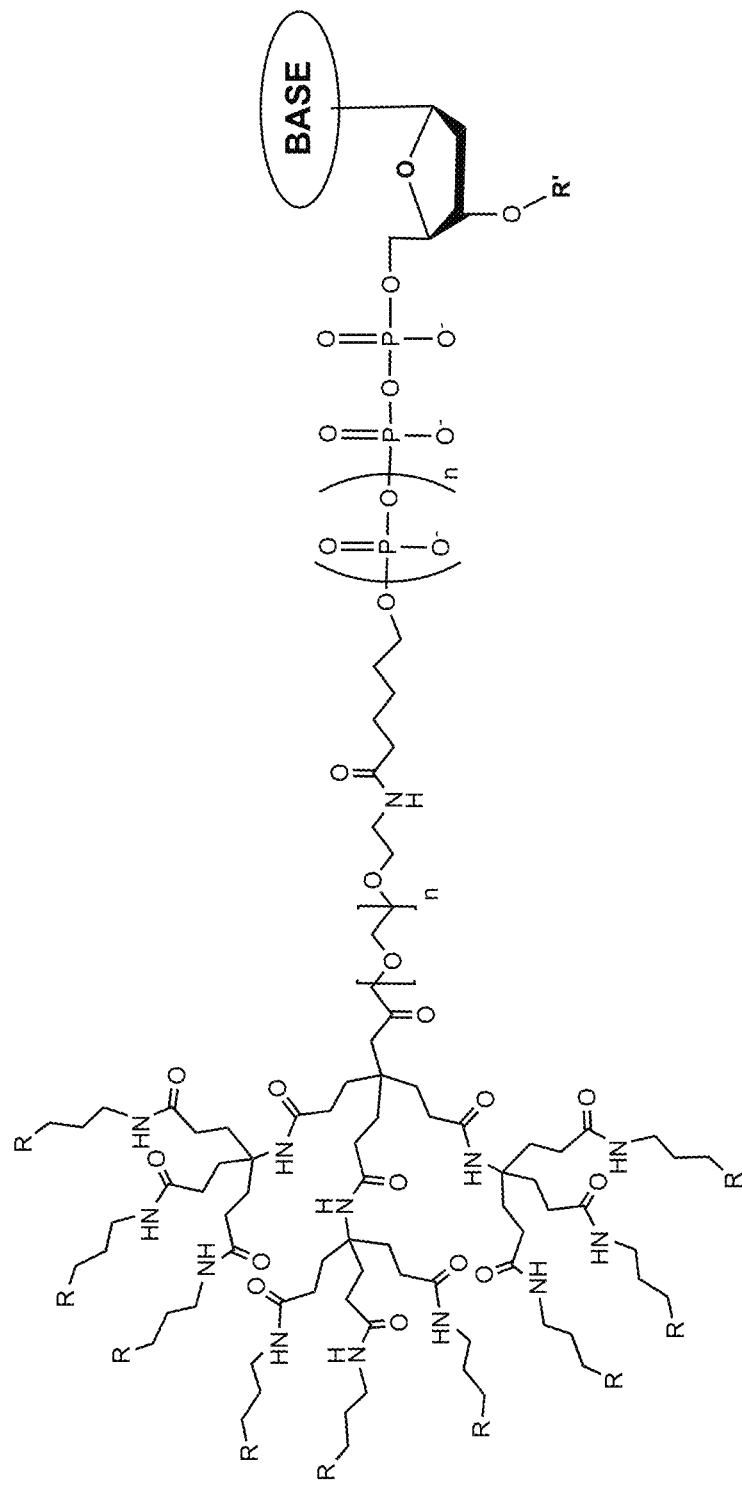
FIG. 12: Example Raman cluster (RC) labeled nucleotide in which RC is attached at the terminal phosphate and 3'-OH is reversibly blocked with a variety of removable groups.

Experiment 2: Ensemble or Single Molecule SBS Sequencing in which the Raman Active Group on the 3'-OH Also Serves as the 3'-Blocking Group and a Cluster of the Same Raman Groups is Present on the Terminal Phosphate Group The Raman active blocking groups on the 3'-OH have already been described in Experiment 1. In addition, clusters from 2-100 Raman active moieties, identical to each other and the 3' group moiety are present (similar to that shown in FIG. 11A). Examples of nucleotides with attached clusters of RAGs are shown in FIG. 12. It has been shown that nucleotides modified with very large polymers including PEG molecules with up to 36 ethylene glycol units (Kumar et al 2012) and nucleic acid chains of up to 30 nucleotides are still correctly recognized as substrates by a variety of polymerases (Fuller et al 2015). RAG clusters have important benefits for SERS detection. The more RAGs present, the more opportunity for some of them to be positioned within a Raman hot zone. Moreover, if measurements are taken over a sufficiently long period, molecular movements of the clusters further increase the likelihood that they will produce a Raman signal. In combination with SERS, this may approach the single molecule measurements scale. One way to increase the available measurement time is to maintain the clusters on the terminal phosphate. Normally, in the polymerase reaction, once a ternary complex consisting of polymerase, template, primer and incoming nucleotide is formed, rapid formation of a phosphodiester bond between the 3' OH on the primer and the α phosphate of the incoming nucleotide takes place, which is accompanied by cleavage of the bond between the α and β phosphates, and release of all the phosphates (pyrophosphate or polyphosphate) except the α phosphate. The incorporation reaction takes place in the presence of catalytic metal ions such as Mg$^{++}$ or Mn$^{++}$ which are positioned in the active site where they coordinate movements necessary for the polymerase reaction to occur (Yang et al 2004). However, non-catalytic metal ions such as Sr$^{++}$ and Ca$^{++}$ have the opposite effect, and in their presence the ternary complex is maintained (Vander Horn et al 2014). This experiment and resulting embodiment of the subject invention take advantage of this to achieve higher sensitivity, allowing enough time for signal acquisition, and approach the single molecule level.

After amplification of DNA on the beads by emulsion PCR, they are washed to remove Mg$^{++}$ and any other catalytic metal ions. When the beads are deposited onto the gold nanoparticle-studded surface containing tethered polymerase molecules, Sr$^{++}$ or Ca$^{++}$ is added along with the primer and the nucleotides bearing the Raman active 3' blocking group and the terminal phosphate-bound Raman cluster. After sufficient time to form the ternary complex, Raman measurements are made. Following measurement for as long as needed to obtain a convincing signature, Mg$^{++}$ is added to allow incorporation. Finally, TCEP is added to remove the blocking group. Sr$^{++}$ is added back to the solution in readiness for addition of the subsequent nucleotide for the next cycle of the sequencing process. Optionally, Sr$^{++}$ is added before addition of TCEP to improve in-phase reading by preventing incorporation of any remaining nucleotide in the case of homopolymers, but if washes are complete, this is less necessary. This method only requires a set of four nucleotides, and in each round it restores the growing DNA strand to a natural state, but it requires several washes. In the case of single molecule sequencing, instead of using templates amplified on beads, templates are hybridized with primers bound to the gold surface.

Experiment 3: Ensemble or Single Molecule Sequencing in which the Raman Active Group on the 3'-OH Also Serves as the 3'-Blocking Group and a Cluster of the Same Raman Groups is Attached Via a Cleavable Linker to the Base This variant, which is similar to Experiment 2 in that many RAGs are present on the nucleotide, does not require switching between non-catalytic and catalytic metal ions. If the cluster on the base is attached via a cleavable linker identical to the one used as a blocking group, cleavage of both can occur at the same time (FIG. 11B). If for example an azidomethyl group or a disulfide group is used to attach the blocking group and the linker on the base, TCEP can be used to remove both (Guo et al 2008). With an allyl group attachment, Pd(0) or tetrabutylammonium peroxydisulphate/iodine may be used (Ju et al 2006, Yang et al 2002). The 2-nitrobenzyl group undergoes photocleavage at 350 nm. Examples of 3'-reversibly blocked nucleotides with clusters on the base via a cleavable linker are shown in FIG. 13. It has been demonstrated the attachment of many large moieties to the 5 position of pyrimidines and the 7 position of purines (Guo et al 2008, Ju et al 2006, Ruparel et al 2005, Seo et al 2005); these do not prevent their ability to be recognized by several classes of polymerases. It should be noted that the azidomethyl group will also produce a peak in the Raman area of interest, though it can be readily resolved from the other Raman active groups. The overall procedure is identical to that in Experiment 1.

Experiment 4: Ensemble or Single Molecule Sequencing in which the Raman Active Group on the 3'-OH Also Serves as the 3'-Blocking Group and a Cluster of the Same Raman Groups is Attached Both to the Terminal Phosphate and Via a Cleavable Linker to the Base This method utilizes twice as many RAGs as either Experiment 2 or 3. The procedure is identical to that of example 2. The only difference is that TCEP (or other deblocking agent) is used to remove the blocking group and the cluster on the base simultaneously. Small remnants of the tag (a propargyl or other small chemical group) remain on the base after its incorporation. Despite these modifications, a substantial number of nucleotides can be added to the primer and the sequence determined (Ju et al 2006, Guo et al 2008).

Figure 14:
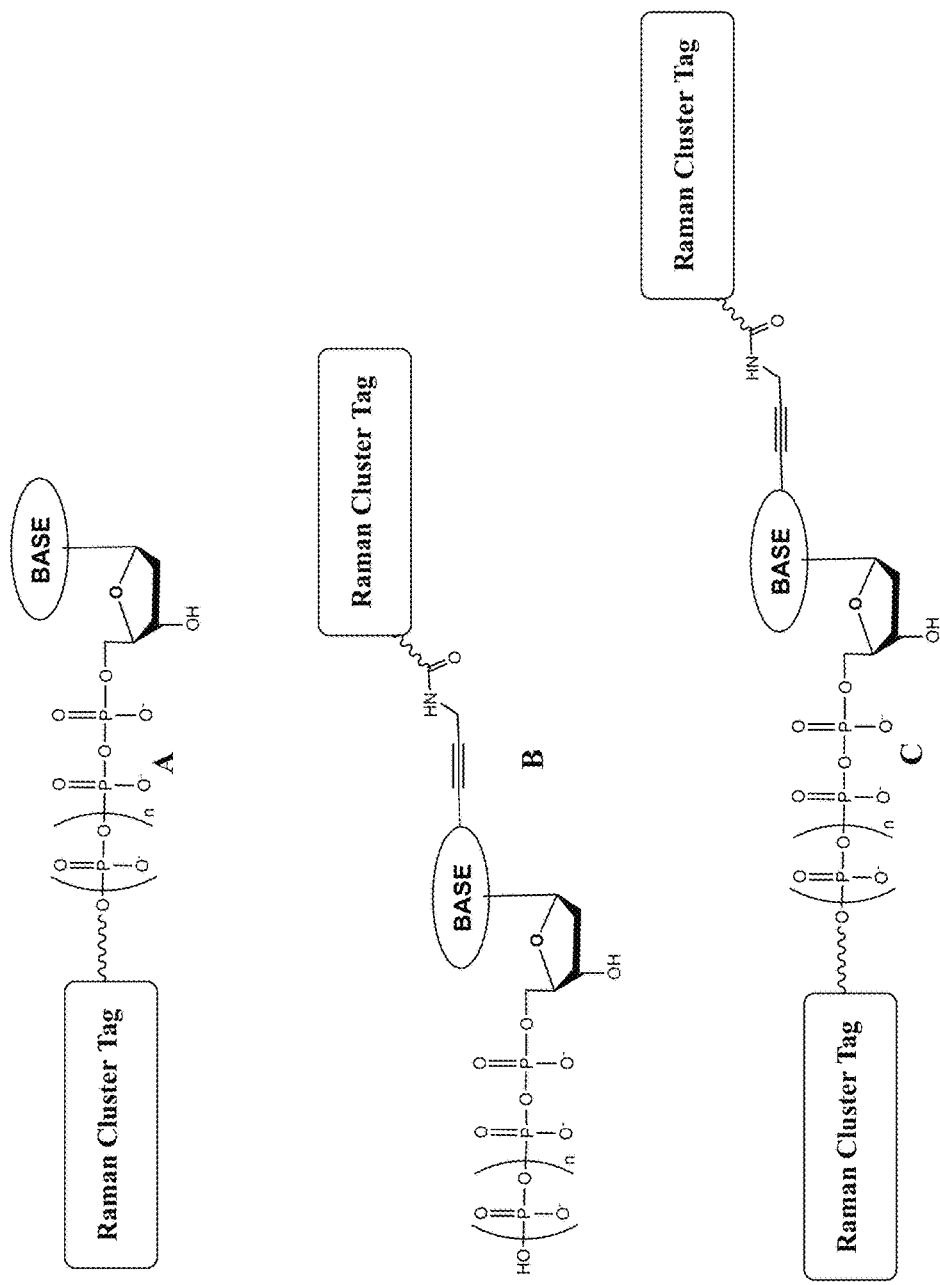
FIG. 14: Raman cluster labeled nucleotides for Raman SBS. RC can be attached at terminal phosphate (A), base (B) and or to both terminal phosphate and base (C).

Experiment 5: Ensemble or Single Molecule Sequencing Using a Cluster of Raman Active Groups on the Terminal Phosphate but No Blocking Group at the 3'-OH Position (FIG. 14A)

In this approach, the nucleotide is added in the presence of a non-catalytic metal ($Sr^{++}$ or $Ca^{++}$) to preserve the ternary complex as long as needed for Raman measurements, exactly as described for Experiment 2. This is necessary as otherwise the tag cluster would be released rapidly during the incorporation reaction. After obtaining the Raman reading, a large excess of nucleotide reversible terminators (NRTs), i.e., nucleotides with blocking groups are added so as to replace the phosphate-tagged nucleotides. Next $Mg^{++}$ or $Mn^{++}$ is added to the solution to allow incorporation of the NRTs. Then TCEP or other reagent to remove the blocking group from the NRT, $Sr^{++}$ or $Ca^{++}$ is added again, and finally the next tagged nucleotide is added to begin the second cycle. This method requires 2 sets of four nucleotides and several washes. Examples of such a nucleotide are shown in FIG. 8.

Experiment 6: Ensemble or Single Molecule Sequencing Using a Cluster of Raman Active Groups on the Base and No Blocking Group on the 3'-OH (FIG. 14B)

Figure 15:
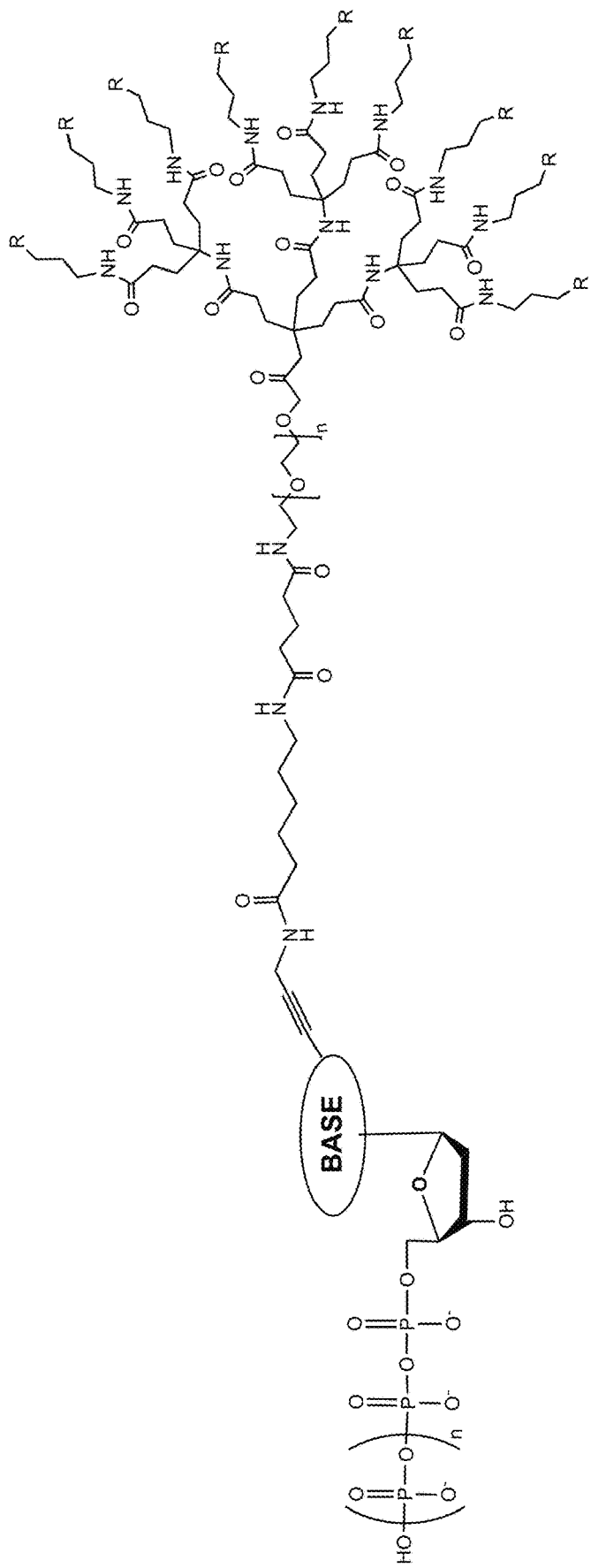
FIG. 15: Example Raman cluster (RC) labeled nucleotide in which RC is attached at the base.

In this variant, as in Experiment 5, there is a need for both the use of non-catalytic metal incubation and subsequent incubation with NRTs. The method is essentially identical to that of Experiment 3. Examples of such a nucleotide are shown in FIG. 15.

Experiment 7: Ensemble or Single Molecule Sequencing Using Clusters of Raman Active Groups on Both the Base and the Terminal Phosphate and No Blocking Group on the 3'-OH (FIG. 14C)

Figure 16:
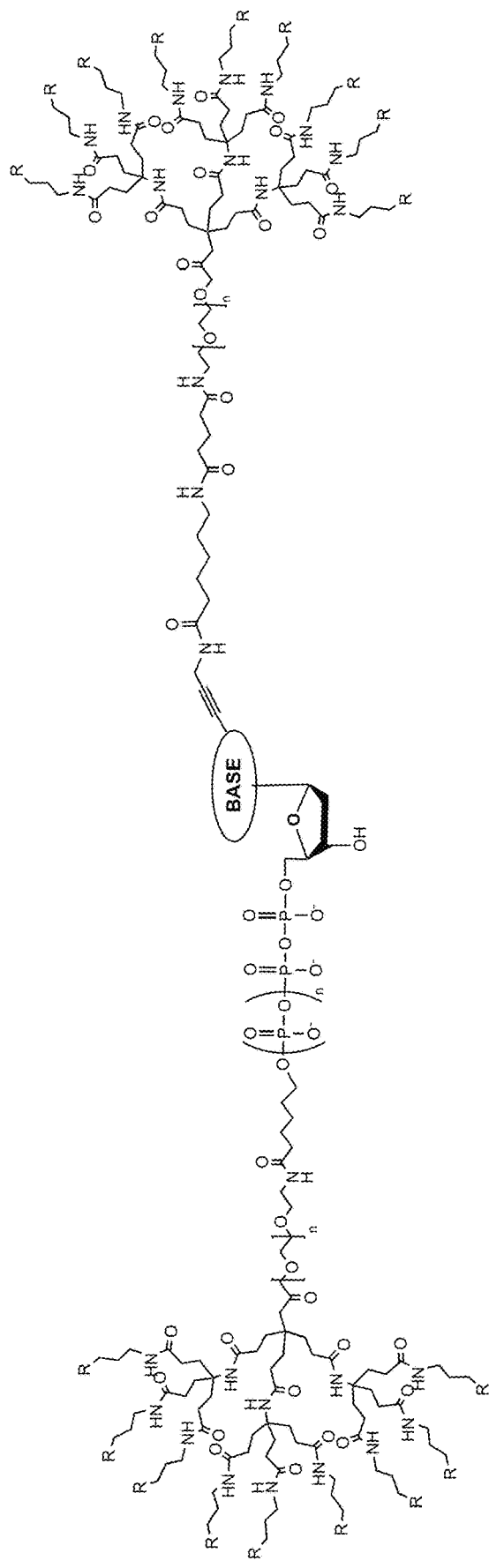
FIG. 16: Example Raman cluster (RC) labeled nucleotides in which RC is attached at both the base and the terminal phosphate.

In this variant, which maximizes the number of possible RAGs, the procedure requires both switching between catalytic and non-catalytic ion incubations and the use of NRTs, following an identical procedure to Experiment 5. Examples of such a nucleotide are shown in FIG. 16.

Figure 17:
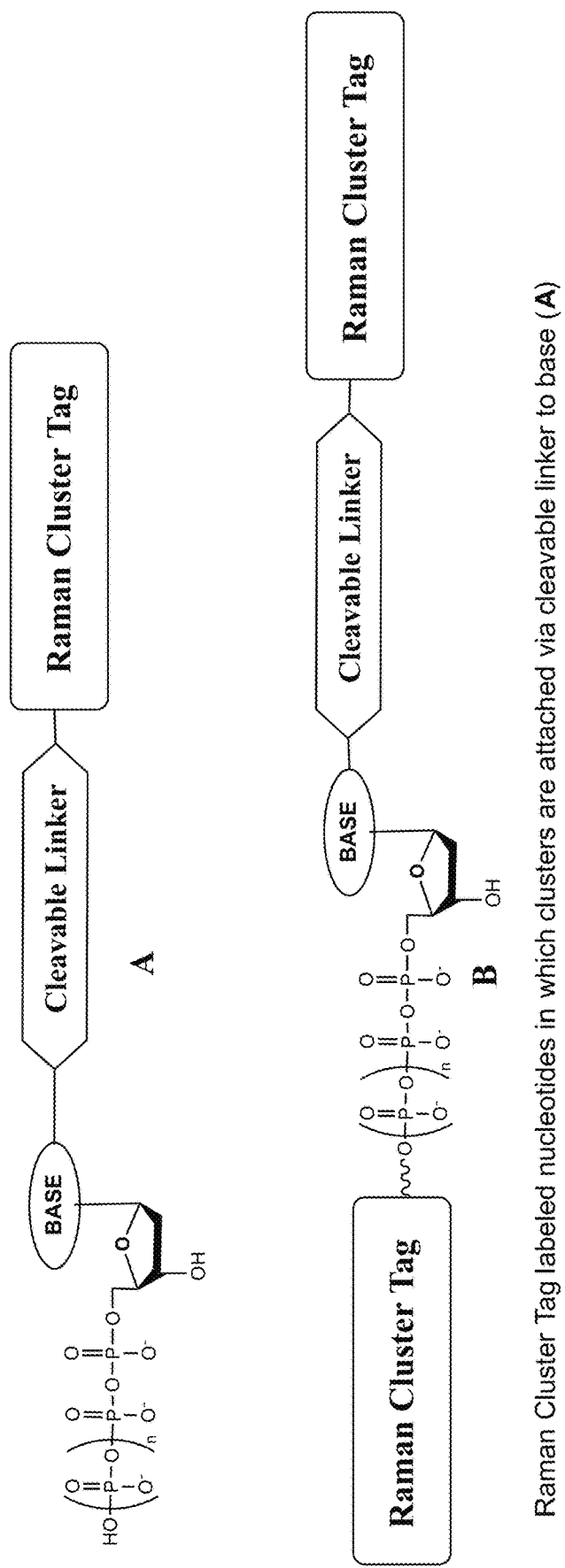
FIG. 17: Raman cluster (RC) labeled nucleotides. RC is attached to base via a variety of cleavable linkers (A) or to both the terminal phosphate and base (B).

Experiment 8: Ensemble or Single Molecule Sequencing Using Clusters of Raman Active Groups Attached to the Base Via Cleavable Linker and No Blocking Groups on the 3' OH (FIG. 17)

Once nucleotides with large clusters of RAGs attached to the base are incorporated, they prevent the entrance and incorporation of further nucleotides. These large RAGs are attached via a cleavable linker, and thus the nucleotides can be considered NRTs. In this case, after the nucleotide is incorporated into the priming strand, Raman detection is performed. Subsequently, the Raman cluster is removed by chemical or other agents depending on the cleavable moiety in the linker to allow entrance of the next nucleotide. This has the advantage of requiring only 2 steps, less than most of the other disclosed experiments, and concomitantly fewer washes. Examples of such nucleotides are shown in FIG. 18.

Experiment 9: Ensemble or Single Molecule Sequencing Using Clusters of Raman Active Groups Attached to the Base Via Cleavable Linker and on Terminal Phosphate and No Blocking Groups (FIG. 17B)

As in Experiment 8, with large enough clusters on the base, these nucleotides serve as NRTs. The following steps are required to take full advantage of these molecules: incubation in the presence of non-catalytic metal ions, measurement of Raman signal, incubation with catalytic metal ions to allow incorporation and release of the cluster on the terminal phosphate, treatment with the appropriate reagent for cleavage of the cluster on the base, and re-incubation with non-catalytic metal ions in preparation for the second cycle. Examples of such nucleotides are shown in FIG. 19.

Experiment 10: Ensemble or Single Molecule Sequencing Using Unincorporable Nucleotides, with Clusters of Raman Active Groups on the Terminal Phosphate, the Base, or Both the Terminal Phosphate and the Base (FIG. 20)

Figure 21:
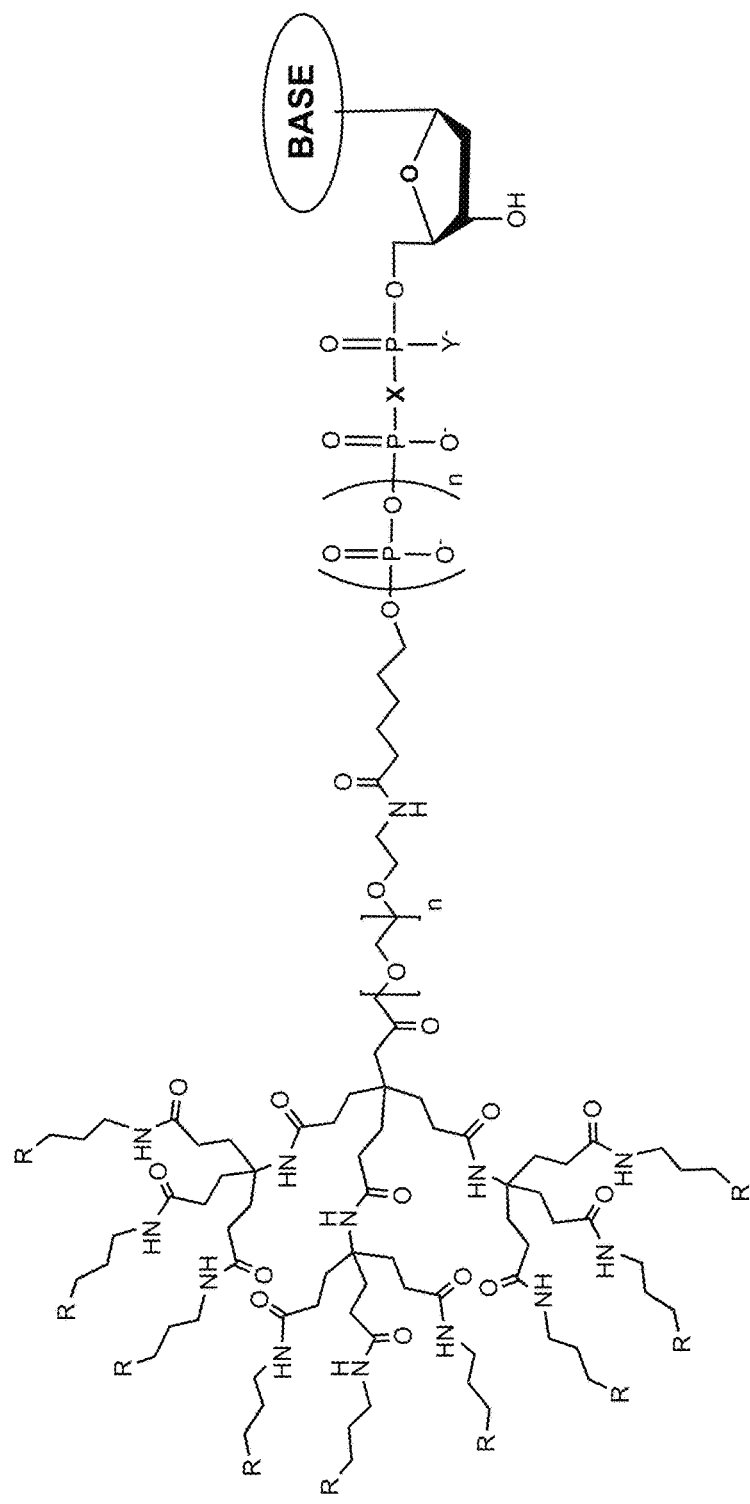
FIG. 21: Raman cluster (RC) labeled non-incorporable nucleotides. Shown is an example in which RC is attached to the terminal phosphate.
Figure 22:
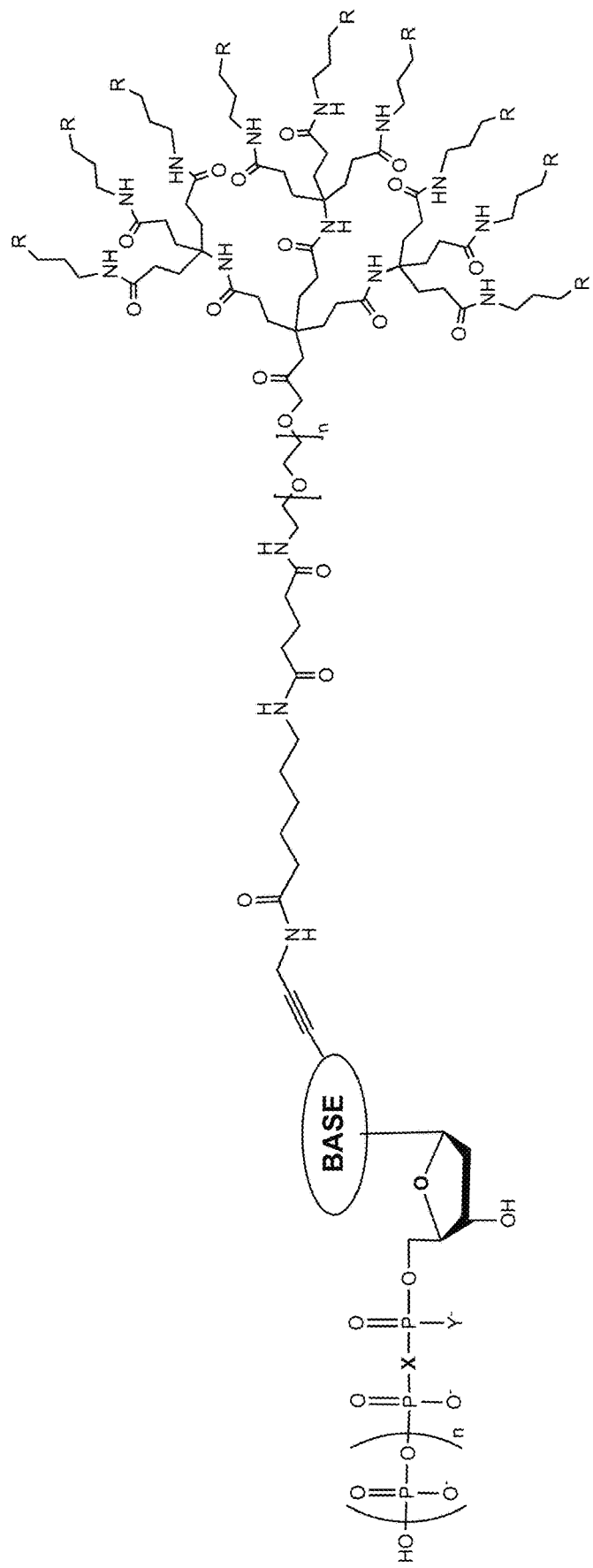
FIG. 22: Raman cluster (RC) labeled non-incorporable nucleotides. Shown is an example in which RC is attached to the base.
Figure 24:
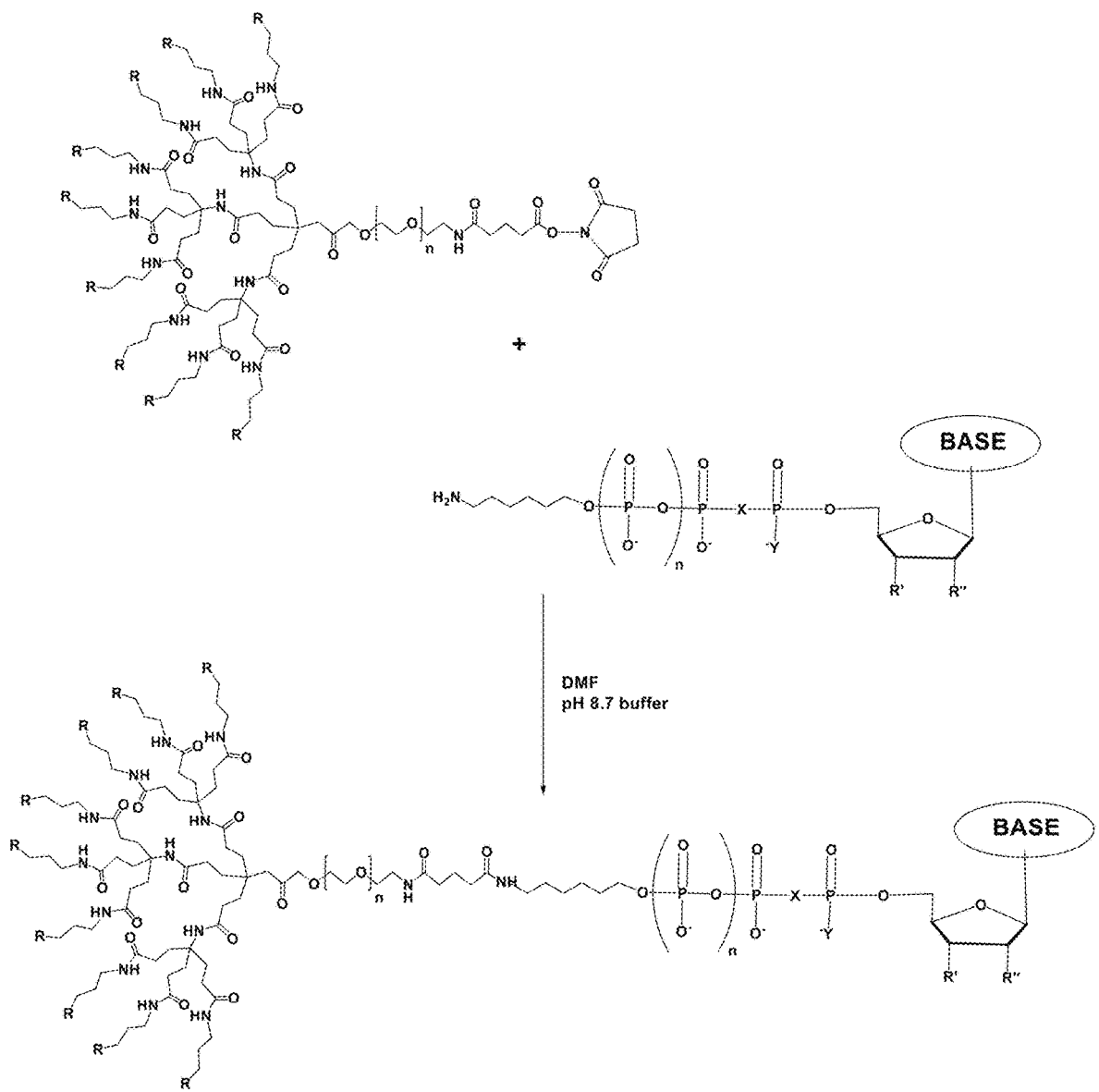
FIG. 24: Example synthesis of terminal phosphate labeled non-incorporable nucleotide for SERS.
Figure 25:
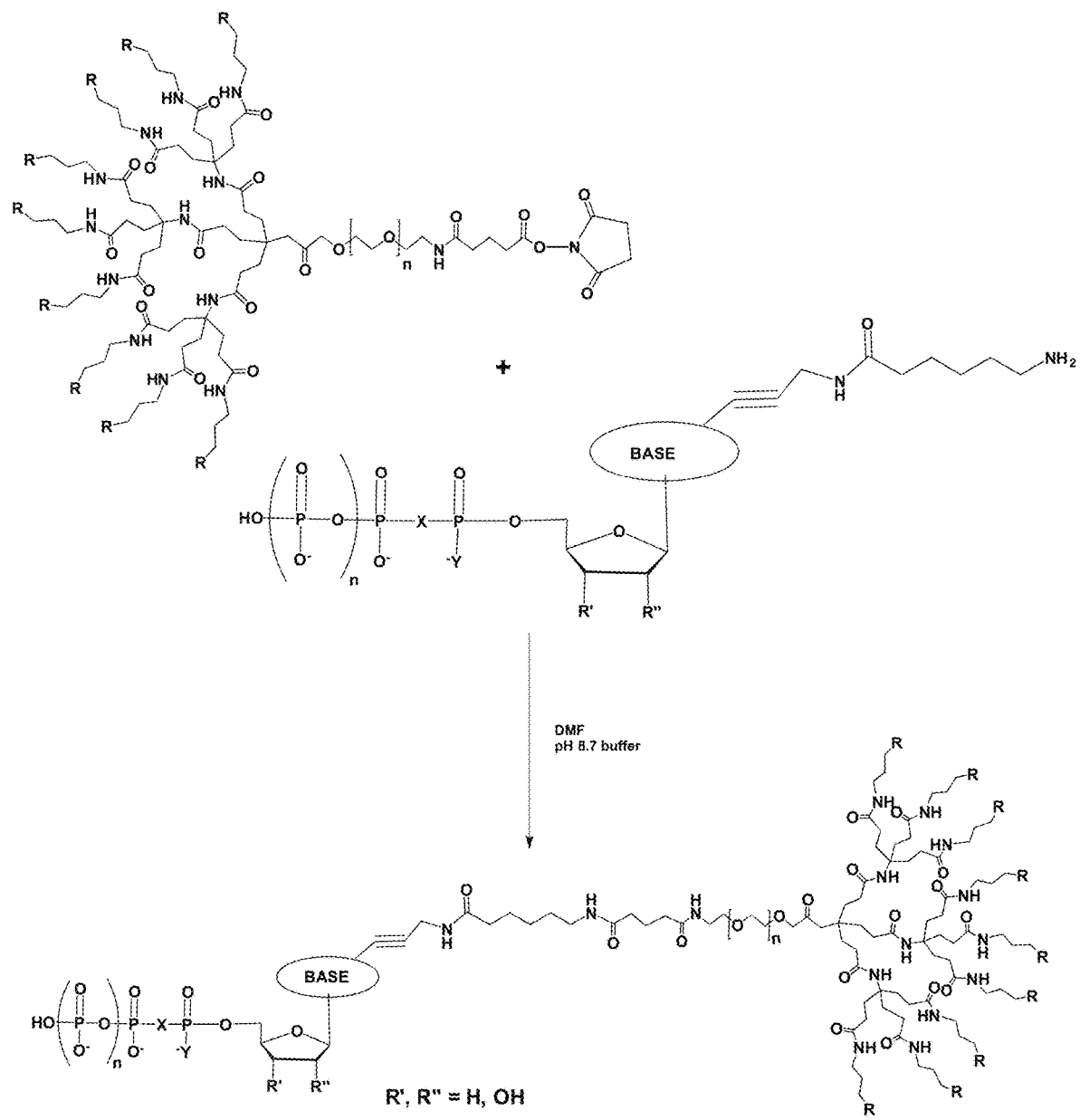
FIG. 25: Example of the synthesis of Raman cluster (RC) labeled non-incorporable nucleotide in which the RC is linked to base.
Figure 27:
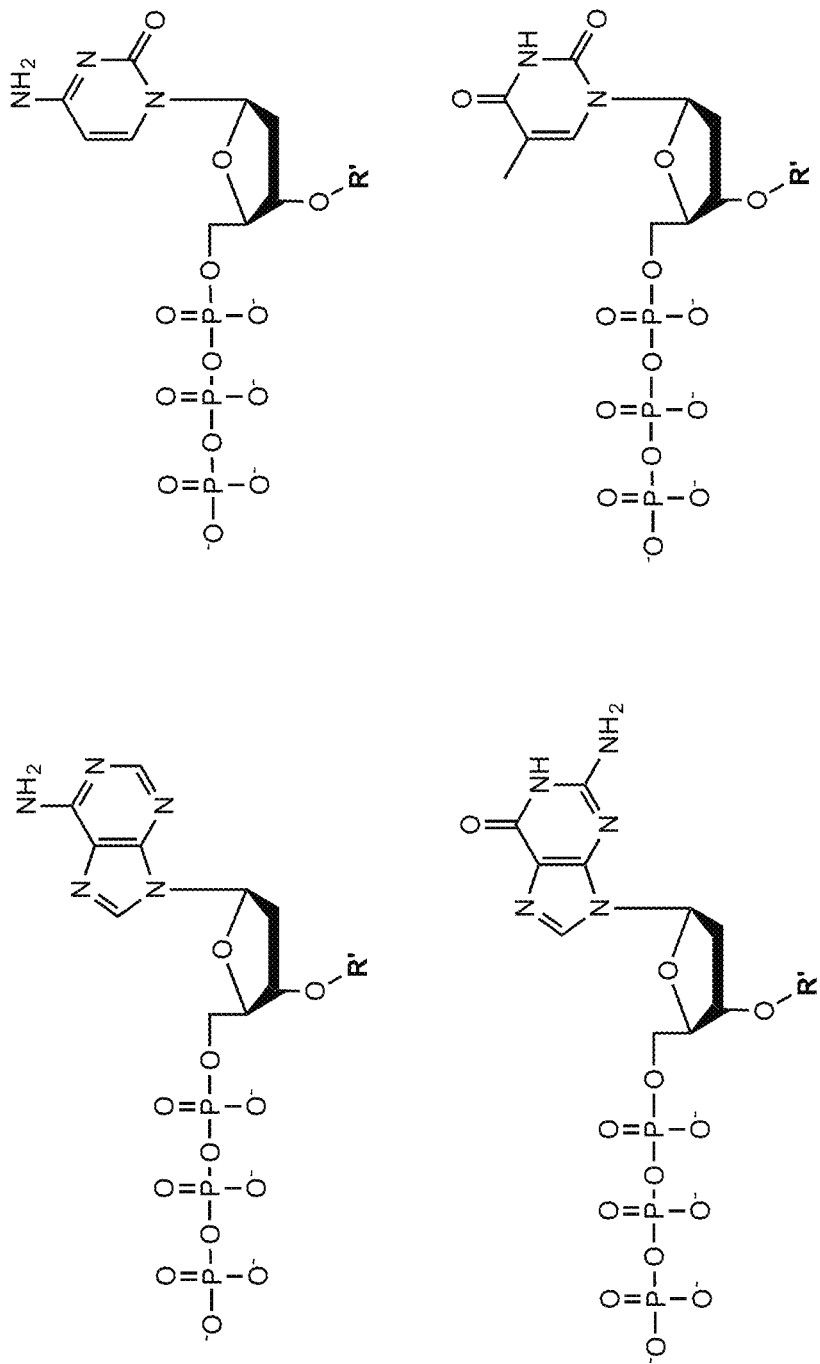
FIG. 27: Structures of 3'-O reversibly blocked nucleotides. A variety of functional groups can be used as reversible blocker including allyl, methoxymethyl, azidomethyl, disulfide and 2-nitrobenzyl which can be readily removed to restore 3'-OH.

In the presence of unincorporable nucleotides, α, β-X-2'-deoxynucleoside 5'-triphosphates (PCP-dNTPs) or polyphosphates (PCP-dNPPs), where X can be $CH_2$, NH, CHF or $CF_2$ (Upton et al 2009), and where the terminal phosphate and/or the base is derivatized with clusters of Raman active chemical moieties (see example structure in FIG. 21, 22, 23 and synthetic schemes shown in FIG. 24, 25, 26), a ternary complex consisting of polymerase, template, primer and nucleotide is formed (Yang et al 2004). Because cleavage of the α, β bond in these nucleotides cannot take place, they are unable to be incorporated into DNA. Thus the ternary complex is monitored for sufficient time to obtain a convincing Raman signal for sequence determination. Nucleotides in solution will usually be too far from the hot zone to give a strong signal. The reaction chamber is then flushed with a high concentration of unlabeled NRTs. These replace the non-hydrolyzable phosphate nucleotides in the ternary complex and are incorporated. The NRTs may have any of a variety of blocking groups attached to the 3'-OH as shown in FIG. 27, including allyl or azido-methyl groups. Following Pd(0) or tetrabutylammonium peroxydisulphate/iodine, or TCEP cleavage, respectively, to restore the 3'-OH group, another round with the next unincorporable nucleotide is initiated, and so forth. Buffer washes are carried out between each reagent addition to reduce background. The use of unincorporable nucleotides obviates the need to use non-catalytic metal ions, resulting in less overall solution changes and washes. Since the unincorporable nucleotides are replaced and washed away, there is no need to cleave or release the tags from the terminal phosphate or the base; indeed a non-cleavable linker can be used for attachment of the clusters on the base. In the case of single molecule sequencing, instead of using templates amplified on beads, templates are reacted with primers bound to the solid surface, e.g., gold or silver; all other steps are the same.

Experiment 11: Single Molecule Real-Time Sequencing on a Gold Surface

In this variant, the polymerase is directly linked to the gold nanoparticles. The template, primer and nucleotide are added to the solution and Raman signals are monitored in real time. Once the ternary complex is formed, the complementary nucleotide is within ~10 nm of the SERS surface for enhanced detection. In this case each of the 4 nucleotides has a cluster with a different set of Raman active groups on its terminal phosphate. For example, A may have a cluster of —N=$N^+$=$N^-$ moieties, C may have a —C≡CH cluster, G may have a cluster and T may have a —C≡C-aryl cluster. In this scenario, there is no need for buffer changes, no NRTs or cleavage steps are required, and sequence reads will be obtained very rapidly. The DNA sequence length is determined by the enzyme's processivity; once the enzyme falls off the DNA, the reaction is considered complete. When a new template subsequently binds to the same polymerase, a second sequence read is obtained. With the use of appropriately designed adapter-based primers, i.e., ones in which the primer only binds to the first half of the adapter sequence on the template strand, it is possible to tell when each new read begins.

General Category 2: Raman Based SBS with Gold Nanoparticle-Decorated Polymerase.

Figure 4:
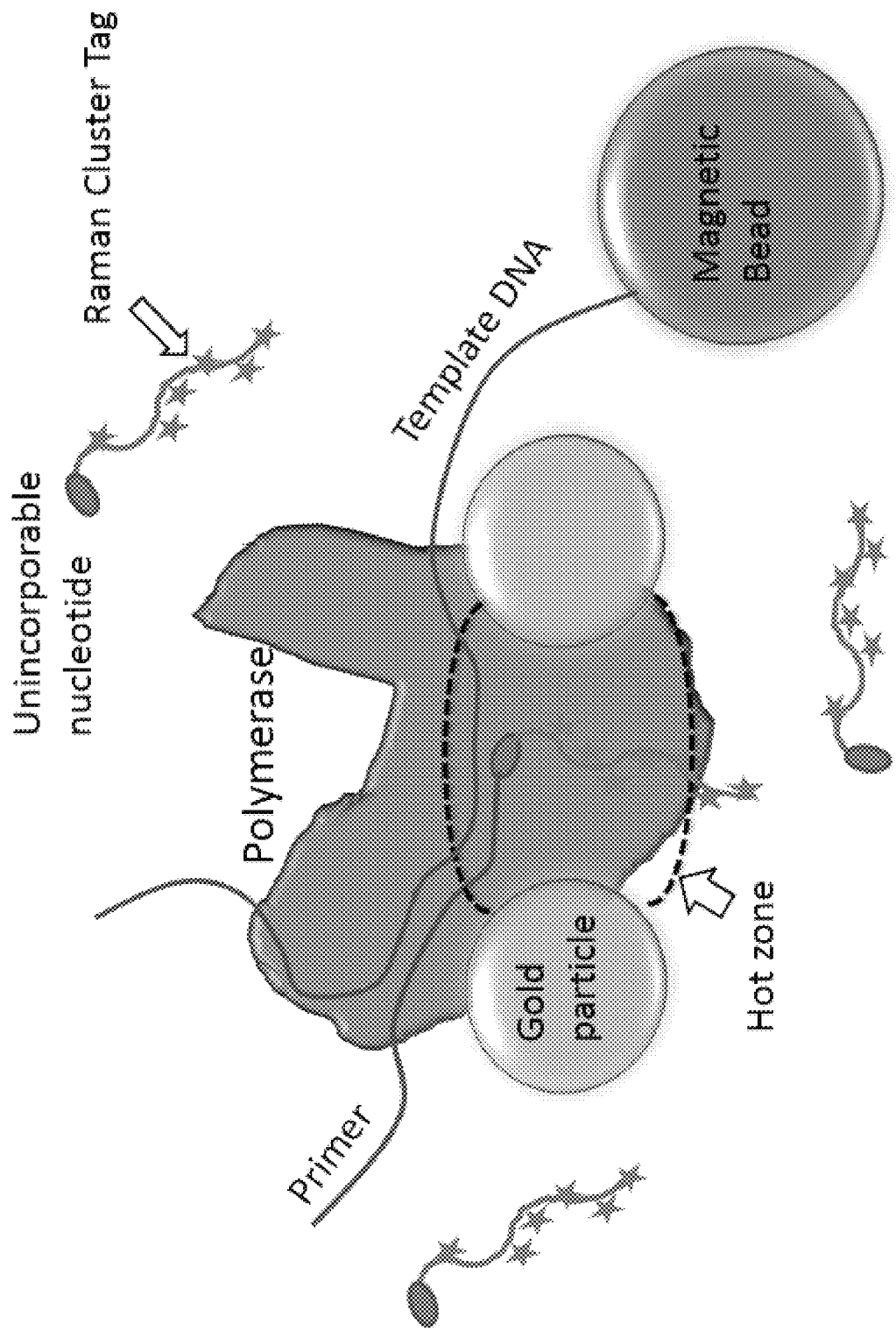
FIG. 4: Ensemble or single molecule Raman SBS with gold nanoparticles attached to polymerase, Raman active groups attached to nucleotide, and DNA bound to magnetic beads. Gold particles are attached to the polymerase as described in FIG. 4 and create a hot zone within the enzyme. Nucleotides in solution are outside the hot zone and will not generate a signal. A magnetic field is used to attract the template (or primer) bearing beads to the surface. Alternatively, the DNA may be directly attached to the surface of the reaction chamber. The solution contains primer, polymerase, and the primer (or template) DNA. Reactions are performed as described in FIG. 1.
Figure 28:
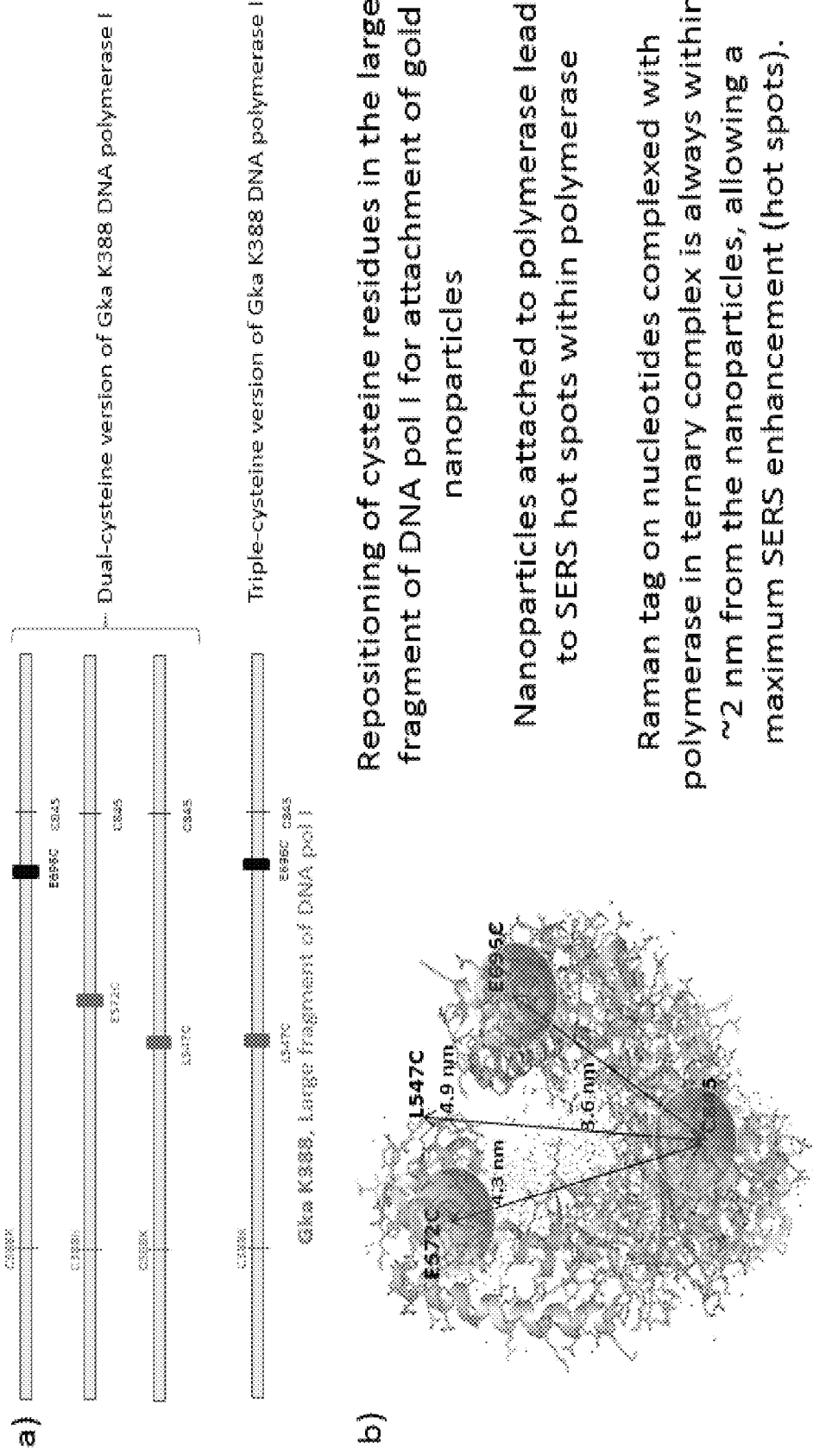
FIG. 28: SERS-active nanoparticles attached to polymerase forming a hot spot within the active center of the enzyme. Repositioning of cysteine in the large fragment of DNA pol I for attachment of gold nanoparticles was carried out. a) Amino acid positions for attachment of gold nanoparticles to the large fragment DNA polymerase I from *Geobacillus kaustophilus* were selected outside the enzyme's catalytic center. The cysteine at position C388 in a wild-type enzyme was substituted with lysine and the amino acids in the designated positions were in turn substituted with cysteines by means of recombinant DNA techniques and can now be used for attachment to gold nanoparticles along with C845. b) Distances of 4 to 5 nm between the wild type C845 and the various substituted designated cysteine positions ensure that the most sensitive SERS hot spot location will be close to the active center of the enzyme. In this way pairs of gold nanoparticles attached to the enzyme at these positions serve as SERS substrates in the detection of nucleotide tags using Raman spectroscopy. With ~1.5 nm gold nanoparticles, as shown here, the distance between gold nanoparticles and the active center where ternary complexes containing Raman-tagged nucleotides are localized is always ~2 nm.
Figure 29:
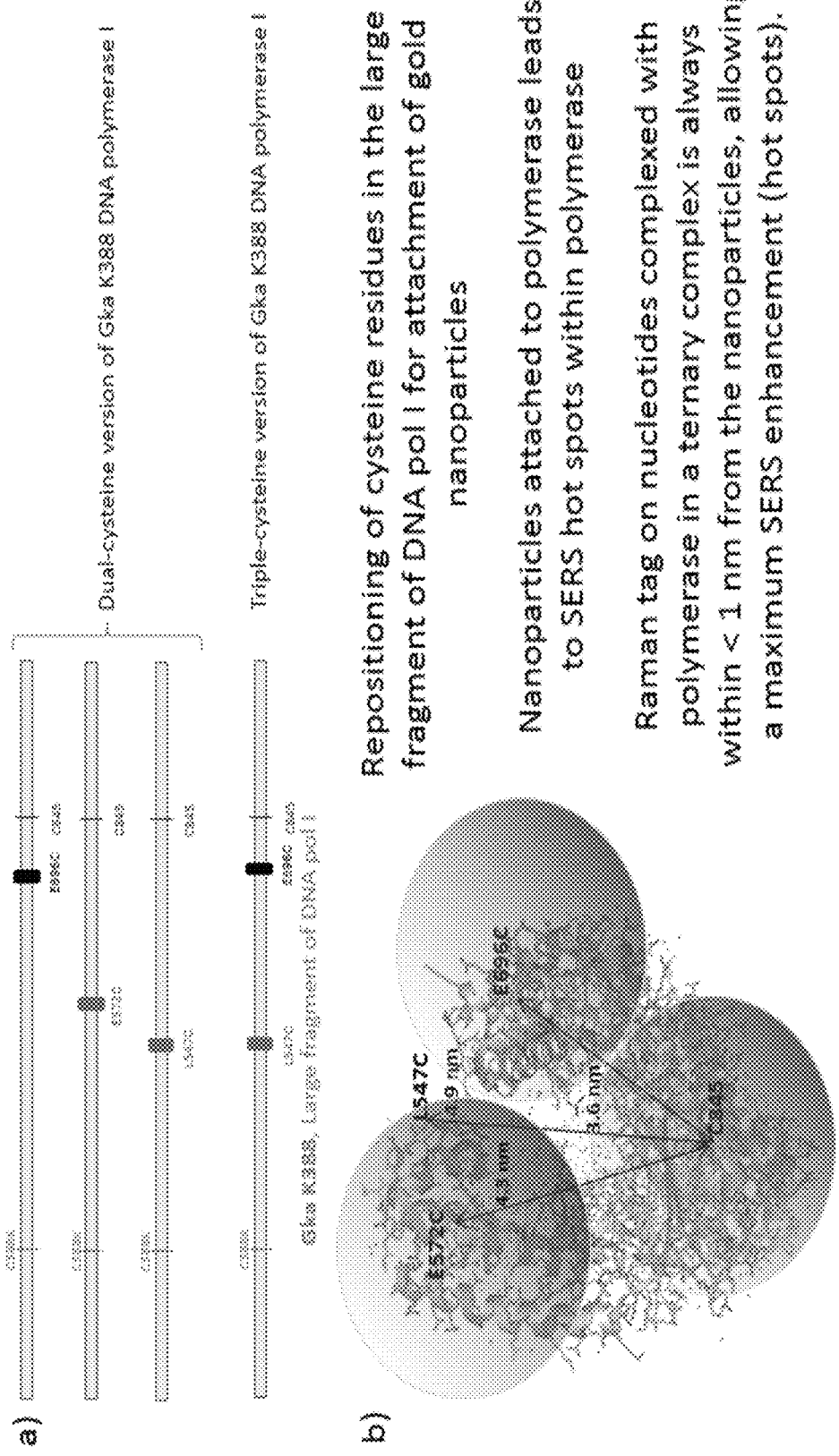
FIG. 29: This figure is identical to FIG. 28, except for the depiction of larger ~3.5 nm gold nanoparticles. In this case the distance between gold nanoparticles and the active center where ternary complexes containing Raman-tagged nucleotides are localized is always <1 nm.

In this second design (see FIGS. 4 and 5), a polymerase molecule is conjugated to 2, 3, 4 or 5 gold nanoparticles of approximately 3-10 nm size (FIGS. 28 and 29). The positions selected for attachment have the following properties: (1) they do not interfere with the polymerase function, i.e., they are excluded from the key binding pockets and active center of the enzyme as well other amino acids required for enzyme activity; and (2) they are distributed so as to produce a hot zone over the polymerase molecule: given that most polymerases have dimensions in the 4-10 nm range, a pair or triangle of gold particles accomplishes this objective, allowing the Raman-tagged nucleotide in the active site of the polymerase to be localized to within 1-3 nm from the nanoparticles for SERS tag detection. Herein disclosed are mutants of several DNA polymerases, having amino acid substitutions that do not inhibit enzyme activity and can be used to attach gold nanoparticles. As an example, herein disclosed are *Geobacillus kaustophilus* DNA polymerase I mutants with pairs of cysteines in various antipodal locations that are used for attachment of gold particles and produce a hot zone over the active center of the polymerase (FIGS. 28 and 29). Binding of ~1.5 nm (FIG. 28) or ~3.5 gold nanoparticles (FIG. 29) at all three positions depicted in those figures results in the Raman tag attached to the nucleotide in the ternary complex always being within 2 nm or <1 nm of the nanoparticles, respectively, for SERS detection. Many additional positions for attachment of the gold particle in this polymerase, and by extension other polymerases, meet these requirements. Two different setups for General Category 2 are depicted in FIGS. 4 and 5. In the first (FIG. 4), the DNA is linked to magnetic beads or the chamber surface. Either the template, as shown in FIG. 4, or the primer may be attached. Many different linkage strategies are available. For instance the DNA may be modified with amino, sulfhydryl, or biotin moieties and reacted with beads derivatized with NHS succinimide, maleimide and streptavidin, respectively. Other chemical pairs, including but not limited to azide-alkyne and trans-cyclooctene-tetrazine, are also feasible. Many homobifunctional and heterobifunctional cross-linkers of assorted lengths are commercially available, including photoactivatable ones. In the second setup (FIG. 5), the gold nanoparticle-decorated polymerases are directly conjugated to the paramagnetic beads or solid surface. Again, many linkage strategies are available in addition to the biotin-Streptavidin pair shown in FIG. 5. Herein disclosed are 10 experimental examples of sequencing approaches in this category. The first 9 experimental examples (Examples 12-20) utilize the setup shown in FIG. 4, while Experiment 11 uses the setup shown in FIG. 5. They may all be considered single molecule methods if random template libraries are added to each well. Alternatively, individual DNA molecules may be amplified on the magnetic beads for ensemble sequencing. Experiment 21 is a real-time single molecule sequencing approach. These examples are very similar to the examples in General Category 1, with nearly identical reagents and steps, hence the descriptions here will generally be shorter. Though feasible with amplification of template DNA and separate wells, the experimental examples herein disclosed do not present an example in this category equivalent to Experiment 1, an ensemble SBS only method in which single RAG molecules were present at the 3'-OH but no RAG clusters were used.

Experiment 12: Ensemble or Single Molecule SBS Sequencing in which the Raman Active Group on the 3'-OH Also Serves as the 3'-Blocking Group and a Cluster of the Same Raman Groups is Present on the Terminal Phosphate Group The template (or primer) DNA-containing beads, free primer (or template), excess polymerase decorated with gold nanoparticles, and nucleotides are added to the reaction chamber in a buffer containing non-catalytic metal ions such as $Sr^{++}$ or $Ca^{++}$. After sufficient time to form the ternary complex, Raman measurements are made. Following measurement for as long as needed to obtain a convincing signature, $Mg^{++}$ is added to allow incorporation. Finally TCEP is added to remove the blocking group. $Sr^{++}$ is added back to the solution in readiness for addition of the subsequent nucleotide for the next cycle of the sequencing process. $Sr^{++}$ may be added before addition of TCEP to improve in-phase reading by preventing incorporation of any remaining nucleotide in the case of homopolymers, but if washes are complete, this is unlikely to be necessary. This method only requires a set of four nucleotides, and in each round it restores the growing DNA strand to a natural state, but it requires several washes. Examples of such a nucleotide are shown in FIG. 11A.

Experiment 13: Ensemble or Single Molecule Sequencing in which the Raman Active Group on the 3'-OH Also Serves as the 3'-Blocking Group and a Cluster of the Same Raman Groups is Attached Via a Cleavable Linker to the Base This variant is similar to Experiment 12 in that many RAGs are present on the nucleotide, but does not require switching between non-catalytic and catalytic metal ions. If the cluster on the base is attached via a cleavable linker identical to the one used as a blocking group, cleavage of both can occur at the same time. If for example an azidomethyl group or a disulfide group is used to attach the blocking group and the linker on the base, TCEP can be used to remove both (Guo et al 2008). With an allyl group attachment, Pd(0) or tetrabutylammonium peroxydisulphate/iodine may be used (Ju et al 2006, Yang et al 2002). The 2-nitrobenzyl group undergoes photocleavage after irradiation at 350 nm. Examples of such a nucleotide are shown in FIG. 19. It has been demonstrated the attachment of many large moieties to the 5 position of pyrimidines and the 7 position of purines (Guo et al 2008, Ju et al 2006, Ruparel et al 2005, Seo et al 2005); these do not prevent their ability to be recognized by several classes of polymerases. It should be noted that the azidomethyl group produces a peak in the Raman area of interest, though it can be readily resolved from the other Raman active groups. In a slight variant of this method the blocking group on the NRT does not have to be a Raman active group.

Experiment 14: Ensemble or Single Molecule Sequencing in which the Raman Active Group on the 3'-OH Also Serves as the 3'-Blocking Group and a Cluster of the Same Raman Groups is Attached Both to the Terminal Phosphate and Via a Cleavable Linker to the Base This method takes advantage of having twice as many RAGs as in Experiment 12 or 13. The procedure is identical to that of Experiment 12. The only difference is that TCEP (or other deblocking agent) is used to remove the blocking group and the cluster on the base simultaneously. Small remnants of the tag (a propargyl or other small chemical group) remain on the base after its incorporation. Despite these modifications, a substantial number of nucleotides can be added to the primer and the sequence determined (Guo et al 2008, Ju et al 2006). In a slight variant of this method the blocking group on the NRT does not have to be a Raman active group.

Experiment 15: Ensemble or Single Molecule Sequencing Using a Cluster of Raman Active Groups on the Terminal Phosphate but No Blocking Group at the 3'-OH Position Initially, the solution contains magnetic beads with either template or primer, free primer or template depending on which is attached to the beads, nucleotides with RAG clusters on the terminal phosphate, polymerase decorated with gold nanoparticles, and non-catalytic metal ions such as $Sr^{++}$ or $Ca^{++}$, resulting in the formation of a ternary complex consisting of polymerase, template, primer and nucleotide (Vander Horn et al 2014). A magnetic field is applied to bring the bead with the DNA primer or template to the surface when the DNA is not directly attached to the surface. (This keeps the beads in a defined position despite multiple washes and cycles of incorporation.) After sufficient time to obtain a Raman signal for the first nucleotide, an excess of nucleotide reversible terminators (NRTs) bearing any of several reversible blocking groups at the 3'-OH position (allyl, methoxymethyl, azidomethyl, disulfide, 2-nitrobenzyl) is added, followed by the addition of a catalytic metal such as $Mg^{++}$ or $Mn^{++}$. This leads to the preferential binding and incorporation of the NRT which temporarily terminates the sequencing reaction at that step. Following the addition of the appropriate chemical (Pd(0) or tetrabutylammonium peroxydisulphate/iodine for allyl, $LiBF_4$ for methoxymethyl (Lipschutz et al 1982, Ireland and Varney 1986), TCEP for azidomethyl and disulfide) or light (in the case of the 2-nitrobenzyl blocker) to reverse the attachment of the blocking group, the non-catalytic metal ions are added back to the system in preparation for the second cycle, which begins with the addition of the next Raman cluster-tagged nucleotide. Examples of such a nucleotide are shown in FIG. 8.

Experiment 16: Ensemble or Single Molecule Sequencing with Incorporable Nucleotides with Raman Active Group Clusters Attached to the Base and No Blocking Group on the 3' OH In this approach, the nucleotide is added in the presence of a non-catalytic metal ($Sr^{++}$ or $Ca^{++}$) to preserve the ternary complex as long as needed for Raman measurements, exactly as described for Experiment 12. This is necessary as otherwise the tag cluster would be released rapidly during the incorporation reaction. After obtaining the Raman reading, a large excess of nucleotide reversible terminators (NRTs), i.e., nucleotides with blocking groups are added so as to replace the phosphate-tagged nucleotides. Next $Mg^{++}$ or $Mn^{++}$ is added to the solution to allow incorporation of the NRTs. Then, after washing out the catalytic metal ions, TCEP or other reagent is added to remove the blocking group from the NRT, $Sr^{++}$ or $Ca^{++}$ is added again, and finally the next tagged nucleotide is added to begin the second cycle. This method requires 2 sets of four nucleotides and several washes. Examples of such a nucleotide are shown in FIG. 15.

Experiment 17: Ensemble or Single Molecule Sequencing Using Clusters of Raman Active Groups on Both the Base and the Terminal Phosphate and No Blocking Group on the 3' OH In this variant, which maximizes the number of possible RAGs, the procedure requires both switching between catalytic and non-catalytic ion incubations and the use of NRTs, following an identical procedure to Experiment 15. Examples of such a nucleotide are shown in FIG. 16.

Experiment 18: Ensemble or Single Molecule Sequencing Using Clusters of Raman Active Groups Attached to the Base Via Cleavable Linker and No Blocking Groups on the 3' OH Once nucleotides with large clusters of RAGs attached to the base are incorporated, they prevent the entrance and incorporation of further nucleotides. These large RAGs are attached via a cleavable linker, and the nucleotides are considered NRTs. In this case, after the nucleotide incorporates into the growing primer strand, Raman detection is performed. Subsequently, the cluster is removed by chemical or other agents depending on the cleavable moiety in the linker to allow entrance of the next nucleotide. This has the advantage of requiring only 2 steps, less than most of the other examples, and concomitantly fewer washes. Examples of such a nucleotide are shown in FIG. 18.

Experiment 19: Ensemble or Single Molecule Sequencing Using Clusters of Raman Active Groups Attached to the Base Via Cleavable Linker and on Terminal Phosphate and No Blocking Groups As in Experiment 18, with large enough clusters on the base, these nucleotides serve as NRTs. The following steps are required to take full advantage of these molecules: incubation in the presence of non-catalytic metal ions, measurement of Raman signal, incubation with catalytic metal ions to allow incorporation and release of the cluster on the terminal phosphate, treatment with the appropriate reagent for cleavage of the cluster on the base, and re-incubation with non-catalytic metal ions in preparation for the second cycle. Examples of such a nucleotide are shown in FIG. 19.

Figure 23:
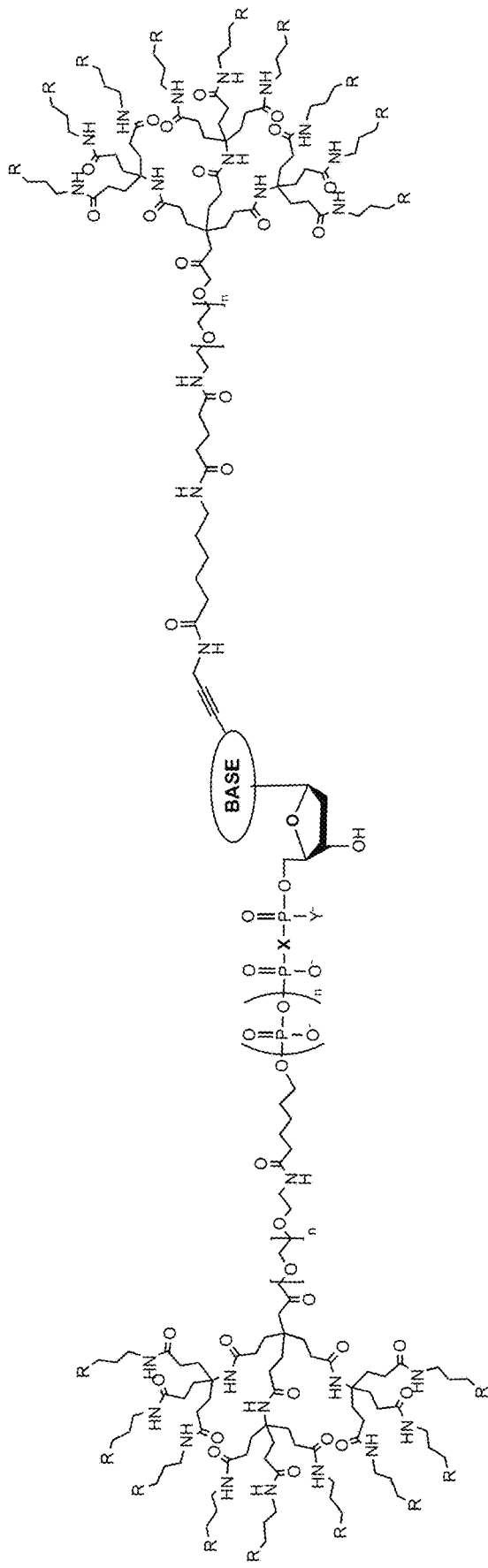
FIG. 23: Raman cluster (RC) labeled non-incorporable nucleotides. Shown is an example in which RC is attached to both the terminal phosphate and base.
Figure 26:
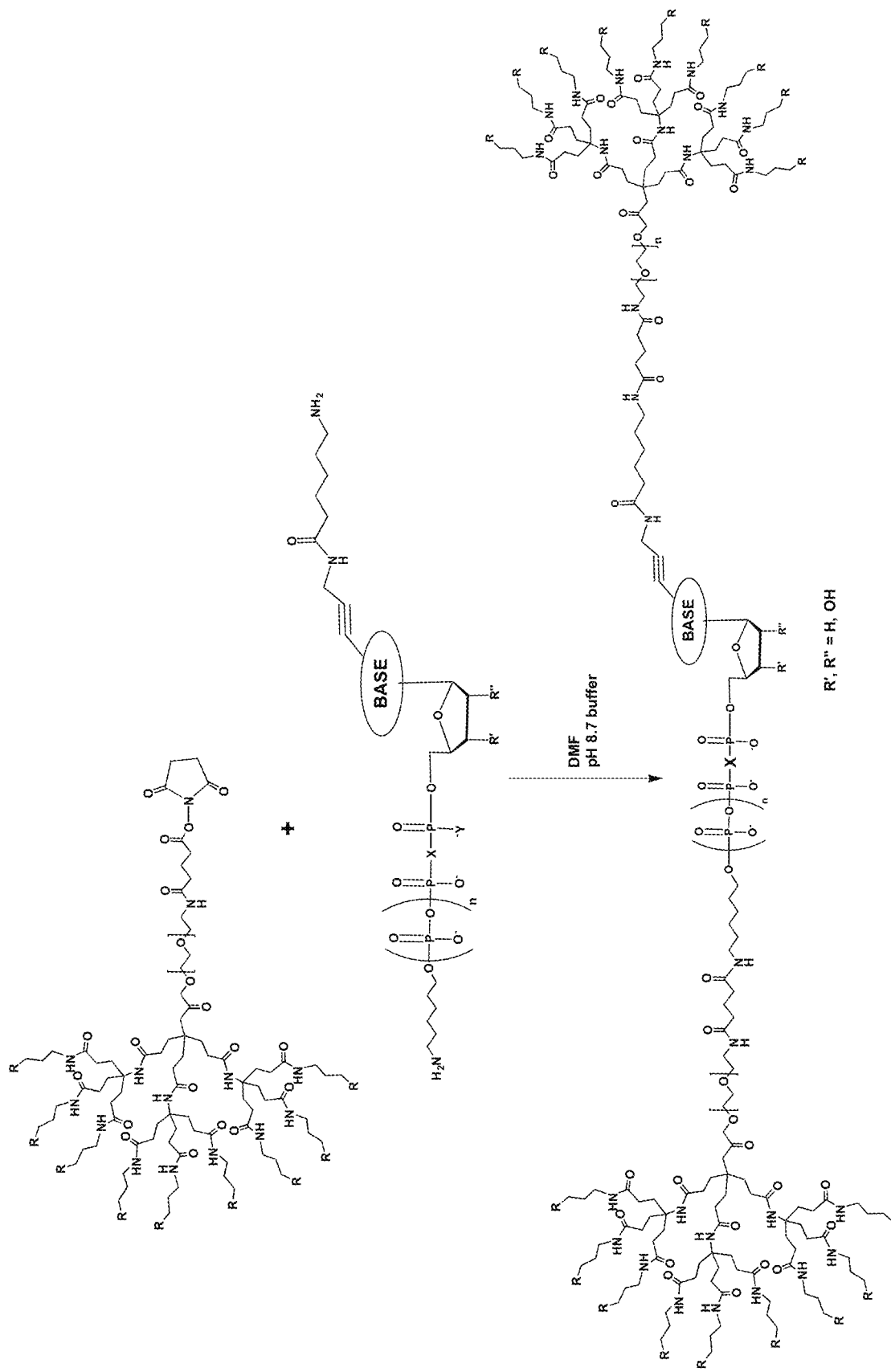
FIG. 26: Synthesis of Raman cluster (RC) labeled nucleotide in which RC is attached to both terminal phosphate and base.

Experiment 20: Ensemble or Single Molecule Sequencing Using Unincorporable Nucleotides, with Clusters of Raman Active Groups on the Terminal Phosphate, the Base, or Both the Terminal Phosphate and the Base In the presence of unincorporable nucleotides, $\alpha$, $\beta$-X-2'-deoxynucleoside 5'-triphosphates (PCP-dNTPs) or polyphosphates (PCP-dNPPs), where X can be $CH_2$, NH, CHF or $CF_2$ (Upton et al 2009), and where the terminal phosphate and/or the base is derivatized with clusters of Raman active chemical moieties (FIG. 20C) (see example structure in FIG. 23 and scheme for its synthesis in FIG. 26), a ternary complex consisting of polymerase decorated with gold beads, template (or primer) on magnetic beads or surface, primer (or template) and nucleotide will be formed (Yang et al 2004). Because cleavage of the $\alpha$, $\beta$ bond in these nucleotides cannot take place, they are unable to be incorporated into DNA. Thus the ternary complex can be monitored for sufficient time to obtain a convincing Raman signal. Nucleotides in solution are usually be too far from the hot zone to give a strong signal. The fluidic chamber is then flushed with a high concentration of unlabeled NRTs. These replace the non-hydrolyzable phosphate nucleotides in the ternary complex and are incorporated. The NRTs may have any of a variety of blocking groups attached to the 3'-OH as shown in FIG. 27, including allyl or azido-methyl groups. Following Pd(0) or tetrabutylammonium peroxydisulphate/iodine, or TCEP cleavage respectively, to restore the 3'-OH group, another round with the next unincorporable nucleotide will be initiated, and so forth. Buffer washes are carried out between each reagent addition to reduce background. The use of unincorporable nucleotides obviates the need to use non-catalytic metal ions, resulting in less overall solution changes and washes. Since the unincorporable nucleotides are replaced and washed away, there is no need to cleave or release the tags from the terminal phosphate or the base; indeed a non-cleavable linker can be used for attachment of the clusters on the base.

Experiment 21: Single Molecule Real-Time Sequencing with Bead-Decorated Polymerase Here the gold-decorated polymerase is itself attached to the magnetic beads or the surface via a biotin-avidin or other linkage and the DNA template, primer and nucleotides are in solution. The gold particles serve to localize the Raman detection to the active site of the enzyme. In this case unblocked nucleotides are used with each of the 4 nucleotides having a cluster with a different set of Raman active groups on its terminal phosphate. For example, A may have a cluster of —N=N$^+$=N$^-$ moieties, C may have a —C≡CH cluster, G may have a —C≡N cluster and T may have a —C≡C-aryl cluster. Raman monitoring takes place in real time. In this scenario, there is no need for buffer changes, no NRTs or cleavage steps are required, and sequence reads will be obtained very rapidly. The DNA sequence length is determined by the enzyme's processivity; once the enzyme falls off the DNA, the reaction is considered complete. If a new template subsequently binds to the same polymerase, a second sequence read is obtained. With the use of appropriately designed adapter-based primers, i.e., ones in which the primer can only bind to the first half of the adapter sequence on the template strand, it is possible to tell when each new read begins.

General Category 3: Raman SBS Using Hybrid SERS Formulation.

In this final category, gold nanoparticles are placed on both the substrate and the polymerase molecules to provide further SERS signal enhancement (FIGS. 6 and 7). Any of the protocols in Experiments 1 through 10 under General Category 1 may be utilized with this approach, exactly as described in that section.

REFERENCES

Ju, J. et al. DNA Sequencing by Synthesis Using Raman and Infrared Spectroscopy Detection. United States Patent Application 20150080232 (2015).

Ju, J. et al. Raman Cluster Tagged Molecules for Biological Imaging. United States Patent Application 20160024570 (2016).

Le Ru, E. C., Blackie, E., Meyer, M., Etchegoin, P. G. Surface Enhanced Raman Scattering Enhancement Factors: A Comprehensive Study. *J. Phys. Chem.* C 111, 13794-13803 (2007).

Palla, M., Guo, W., Shi, S., Li, Z., Wu, J., Jockusch, S., Guo, C., Russo, J. J., Turro, N. J., Ju, J. DNA sequencing by synthesis using 3'-O-azidomethyl nucleotide reversible terminators and surface-enhanced Raman spectroscopic detection. *RSC Advances* 4, 49342-49346 (2014).

Chen, H.-Y., Lin, M.-H., Wang, C.-Y., Chang, Y.-M., Gwo, S. Large-scale hot spot engineering for quantitative SERS at the single-molecule scale. *J. Am. Chem. Soc.* 137, 13698-13705 (2016).

Dressman, D., Yan, H., Traverso, G., Kinzler, K. W., Vogelstein, B. Transforming single DNA molecules into fluorescent magnetic particles for detection and enumeration of genetic variations. *Proc. Natl. Acad. Sci. U.S.A* 100, 8817-8822 (2003).

Shendure, J., Porreca, G. J., Reppas, N. B., Lin, X., McCutcheon, J. P., Rosenbaum, A. M., Wang, M. D., Zhang, K., Mitra, R. D., Church, G. M. Accurate multiplex polony sequencing of an evolved bacterial genome. *Science* 309, 1728-1732 (2005).

Bentley, D. R., et al. Accurate whole human genome sequencing using reversible terminator chemistry. *Nature* 456, 53-59 (2008).

Ma, Z., et al. Isothermal amplification method for next-generation sequencing. *Proc. Natl. Acad. Sci. U.S.A* 110, 14320-14323 (2013).

Harris, T. D. et al. Single-molecule DNA sequencing of a viral genome. *Science* 320, 106-109 (2008).

Eid, J. et al Real-time DNA sequencing from single polymerase molecules. *Science* 323, 133-138 (2009).

Korlach J., et al. Real-time DNA sequencing from single polymerase molecules. *Methods Enzymol* 472, 431-55 (2010).

Kumar, S. et al. PEG-labeled nucleotides and nanopore detection for single molecule DNA sequencing by synthesis. *Sci Rep* 2, 684 (2012).

Fuller, C. W., Kumar, S., Ju, J., Davis, R., Chen, R. Chemical methods for producing tagged nucleotides. Patent Application US20150368710 (2015).

Yang, L., Arora, K., Beard, W. A., Wilson, S. H., Schlick, T. Critical role of magnesium ions in DNA polymerase beta's closing and active site assembly. *J. Am. Chem. Soc.* 126, 8441-8453 (2004).

Vander Horn, P. B. Nucleotide transient binding for sequencing methods. U.S. Pat. No. 8,632,975 B2 (2014).

Lipshutz, B. H., Harvey, D. F. Hydrolysis of acetals and ketals using LiBF4, *Synth. Commun.* 12, 267-277 (1982).

Ireland, R. E., Varney M. D. Approach to the total synthesis of chlorothricolide: synthesis of (+/−)-19,20-dihydro-24-O-methylchlorothricolide, methyl-ester, ethyl carbonate. *J. Org. Chem.* 51, 635-648 (1986).

Guo J, et al. Four-color DNA sequencing with 3'-O-modified nucleotide reversible terminators and chemically cleavable fluorescent dideoxynucleotides. *Proc. Natl. Acad. Sci. U.S.A* 105, 9145-9150 (2008).

Ju, J., et al. Four-color DNA sequencing by synthesis using cleavable fluorescent nucleotide reversible terminators. *Proc. Natl. Acad. Sci. U.S.A* 103, 19635-19640 (2006).

Yang, S. G., Park, M. Y., Kim, Y. H. Facile and chemoselective cleavages of allyl ethers utilizing tetrabutylammonium sulfate radical species. *Synlett.* 2002, 492-494 (2002).

Ruparel, H., et al. Design and synthesis of a 3'-O-allyl photocleavable fluorescent nucleotide as a reversible terminator for DNA sequencing by synthesis. *Proc. Natl. Acad. Sci. U.S.A* 102, 5932-5937 (2005).

Seo, T. S., et al. Four-color DNA sequencing by synthesis on a chip using photocleavable fluorescent nucleotides. *Proc. Natl. Acad. Sci. U.S.A* 102, 5926-5931 (2005).

Upton, T. G., et al. Alpha, beta-difluoromethylene deoxynucleoside 5'-triphosphates: a convenient synthesis of useful probes for DNA polymerase beta structure and function. *Org. Lett.* 11, 1883-1886 (2009).

What is claimed is:

1. A compound having the structure:

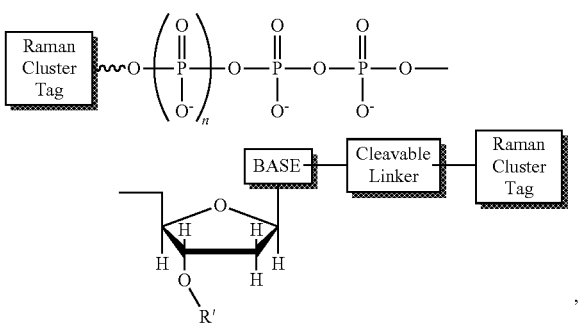

wherein the base is A, G, T, C, or U or an analogue of one of the foregoing, wherein R' is a reversible blocking moiety that prevents a polymerase from incorporating the compound into a growing polynucleotide strand, or R' is H, and wherein n=0, 1, 2, 3, 4, 5, or 6.

2. The compound of claim 1, having the structure:

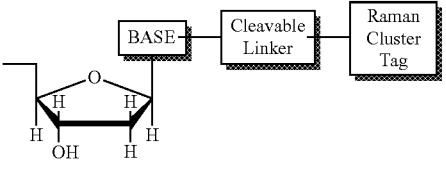

wherein n=1, 2, 3, 4, 5, or 6.

3. The compound of claim 2 having the structure:

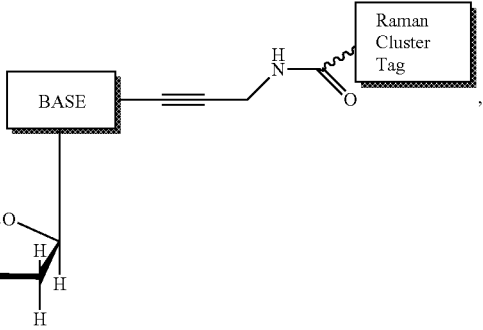

wherein n=0, 1, 2, 3, 4, 5, or 6.

4. The compound of claim 1 having the structure:

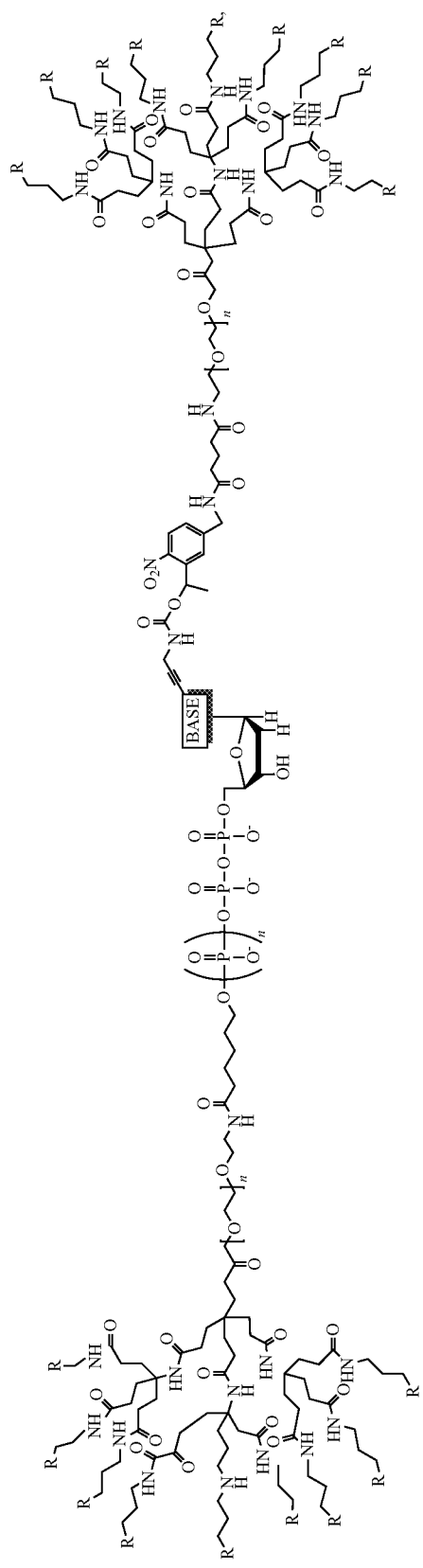
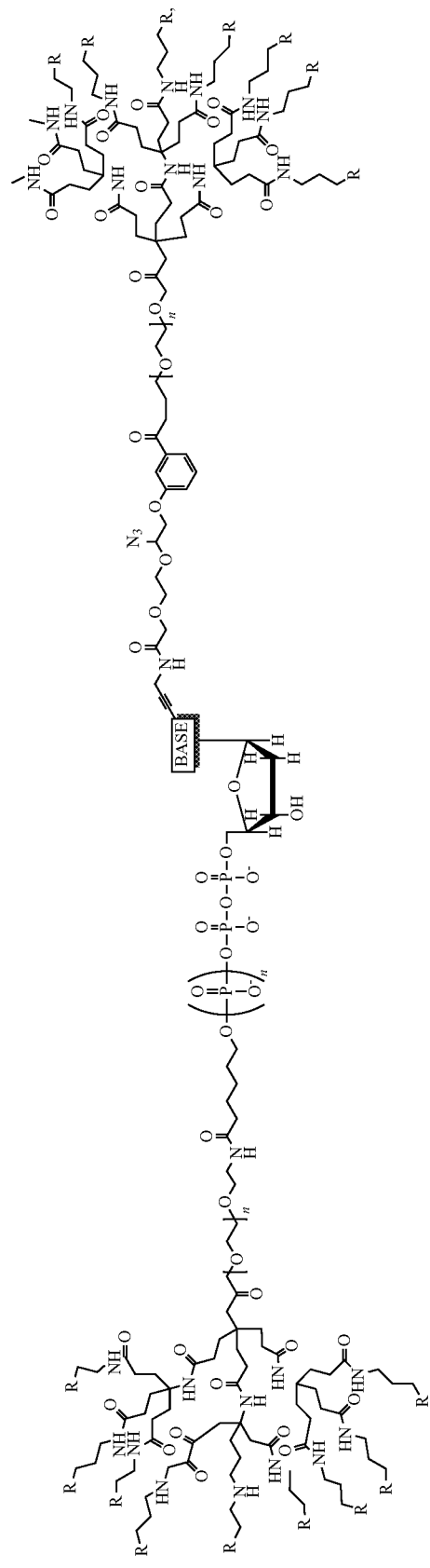

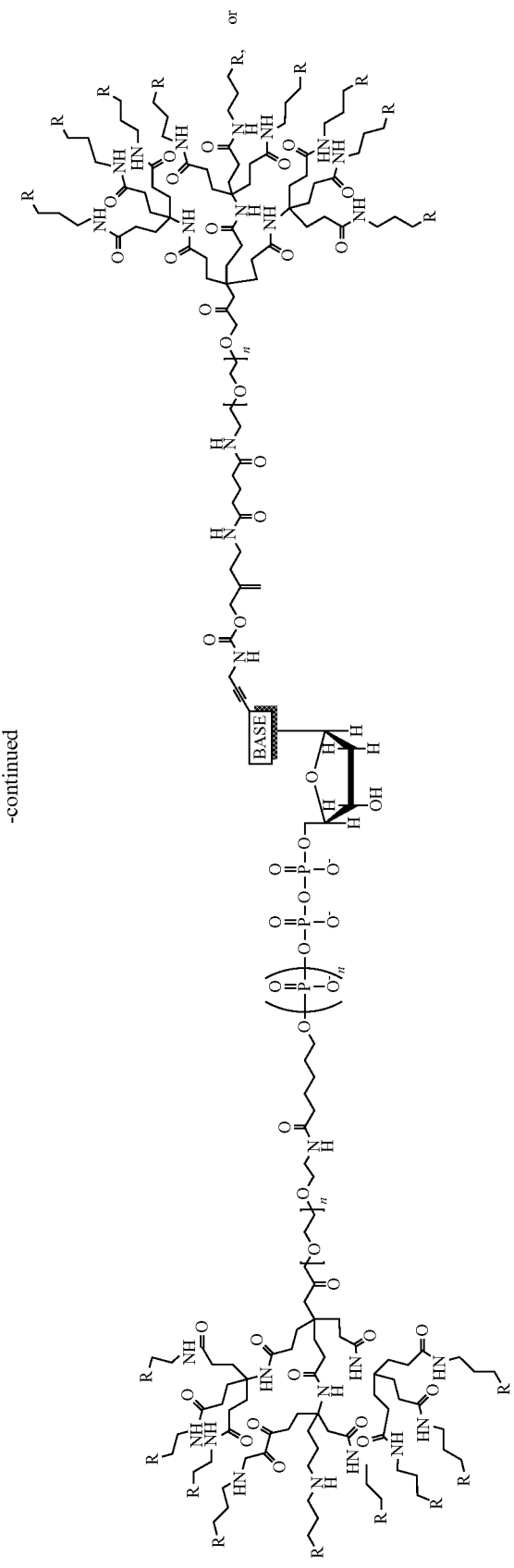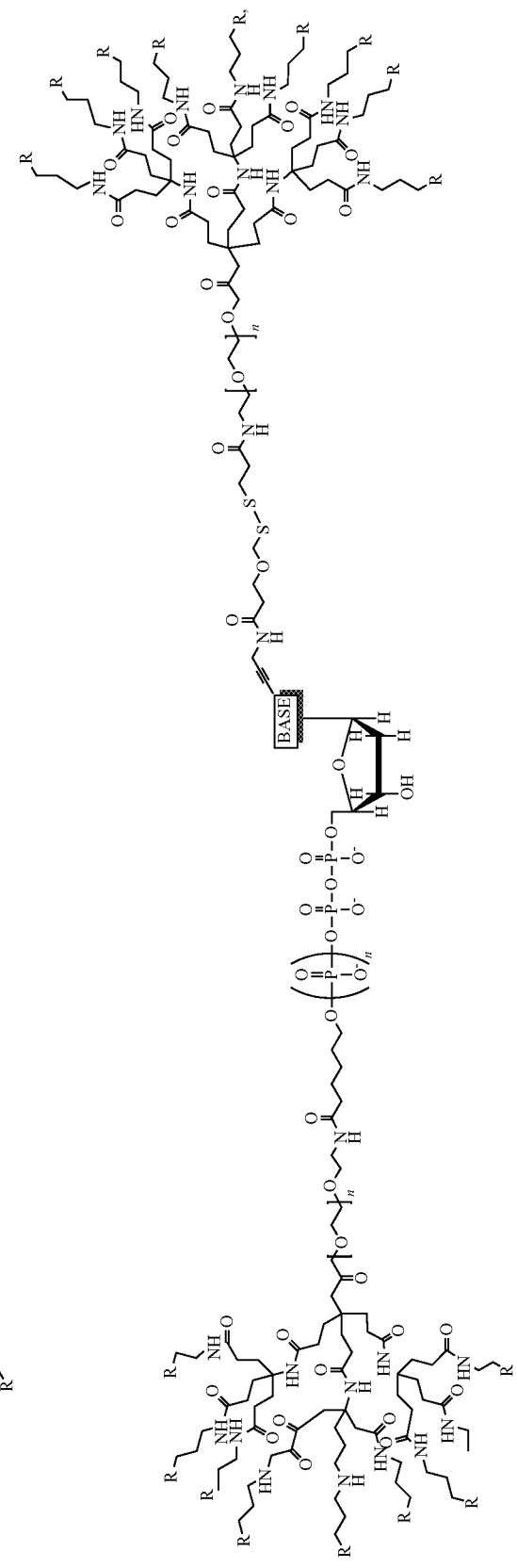

wherein R is a Raman active group and n=0, 1, 2, 3, 4, 5, or 6.

5. The compound of claim 1, wherein R' comprises a Raman cluster tag.

6. The compound of claim 1 wherein the cleavable linker and/or reversible blocking moiety independently comprise any one of an allyl, alkyl, carbonyl, Sieber linkers, indole, disulfide, dithiomethyl, azidomethyl, or nitrobenzyl.

7. The compound of claim 1, wherein the reversible blocking moiety may be cleaved, and thereby result in a 3'-OH.

8. The compound of claim 7, wherein the reversible blocking moiety is photo cleavable or chemically cleavable.

9. The compound of claim 8, wherein the reversible blocking moiety is cleavable with one or more of Pd(0), tetrabutylammonium, DTT, a triphosphine, peroxydisulphate, or iodine.

10. A compound having the structure:

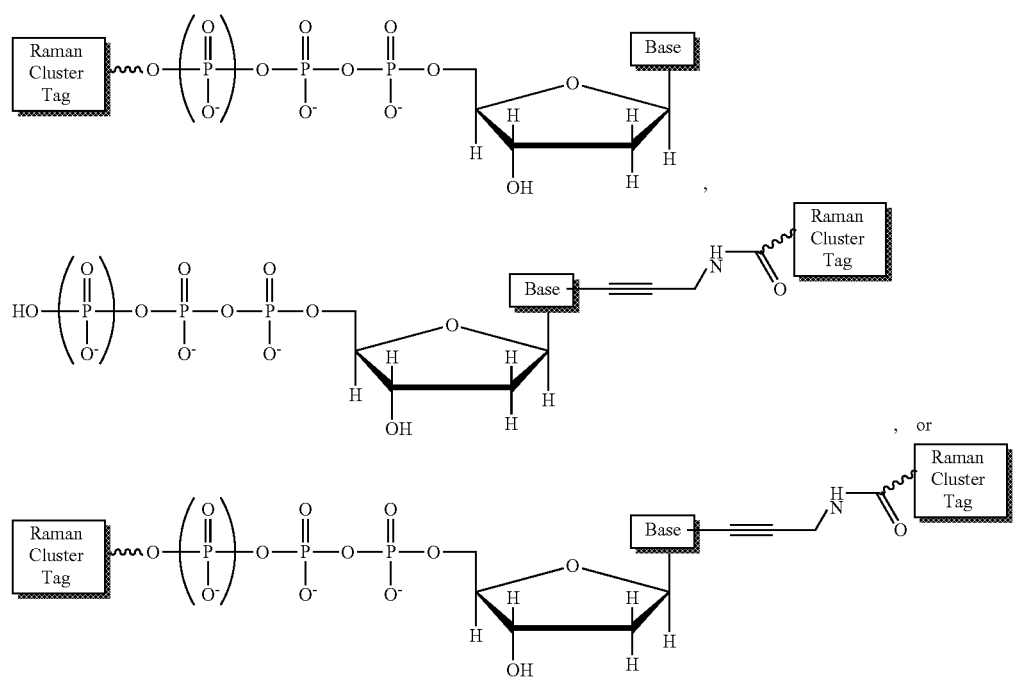

wherein base is any one of A, G, T, C, or U, wherein n=0, 1, 2, 3, 4, 5, or 6, wherein the Raman Cluster Tag comprises Raman active groups, wherein X is any one of $CH_2$, NH, CHF—, or $CF_2$, and wherein Y is any one of O, S, or $BH_3$.

11. The compound of claim 10 having the structure:

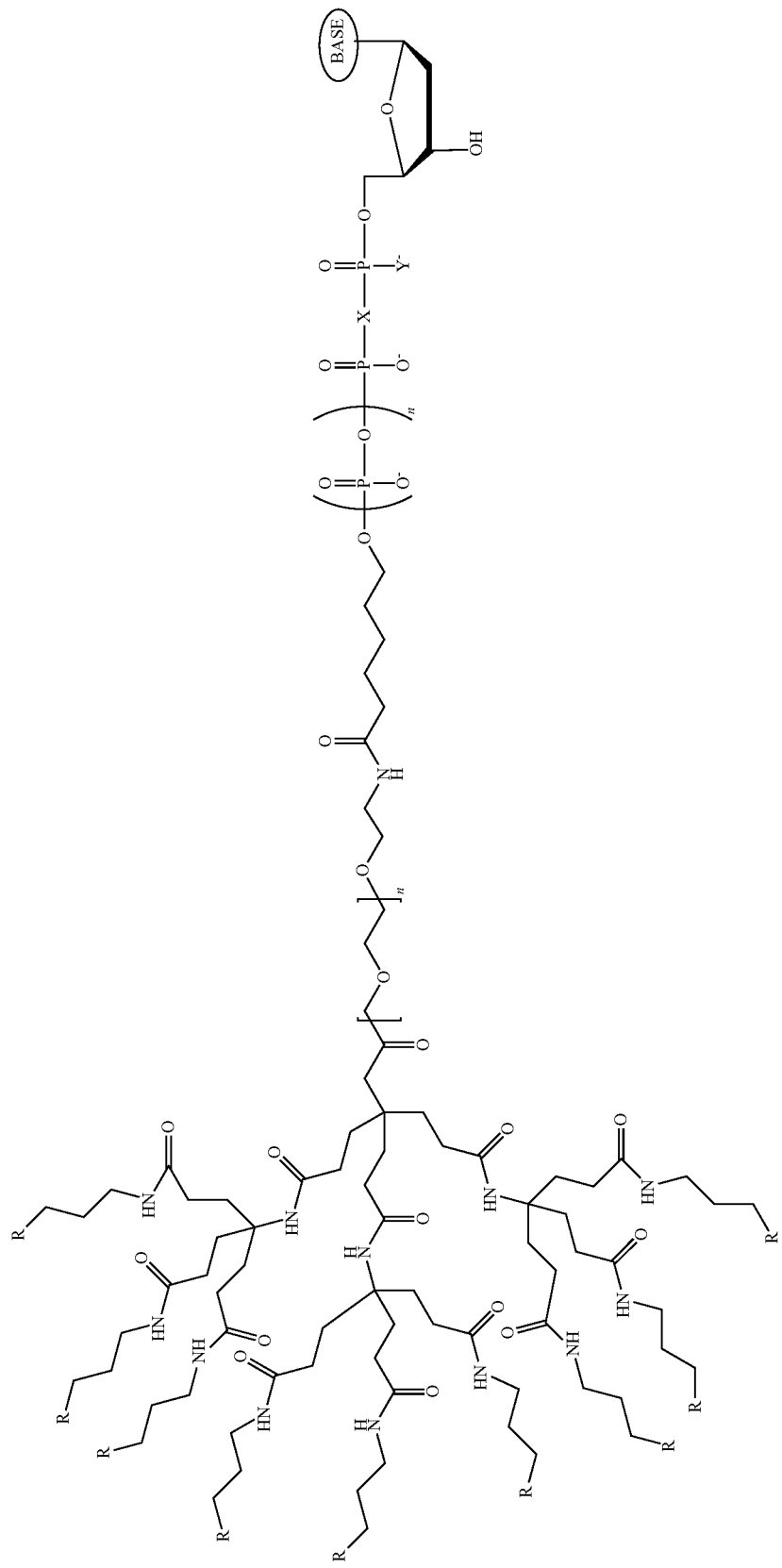

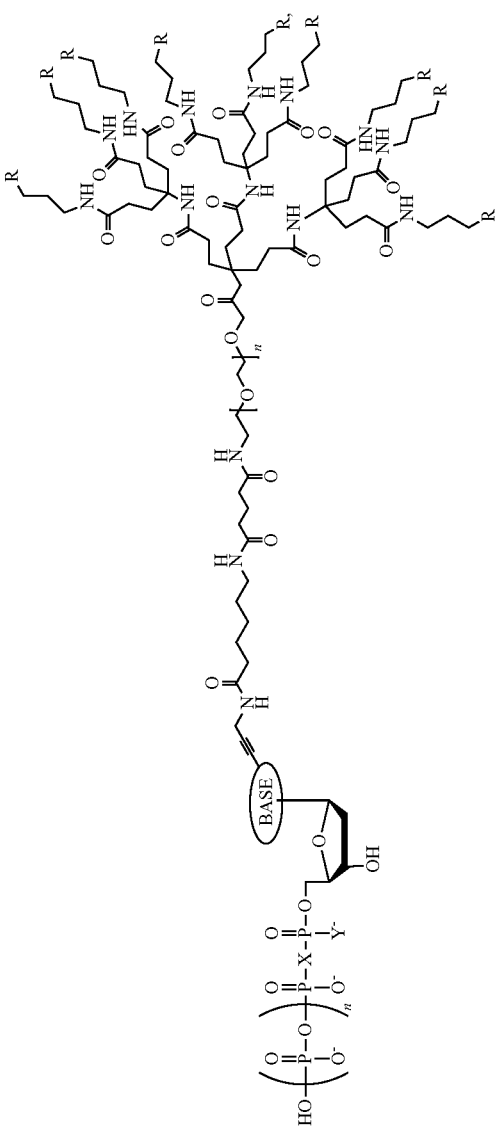
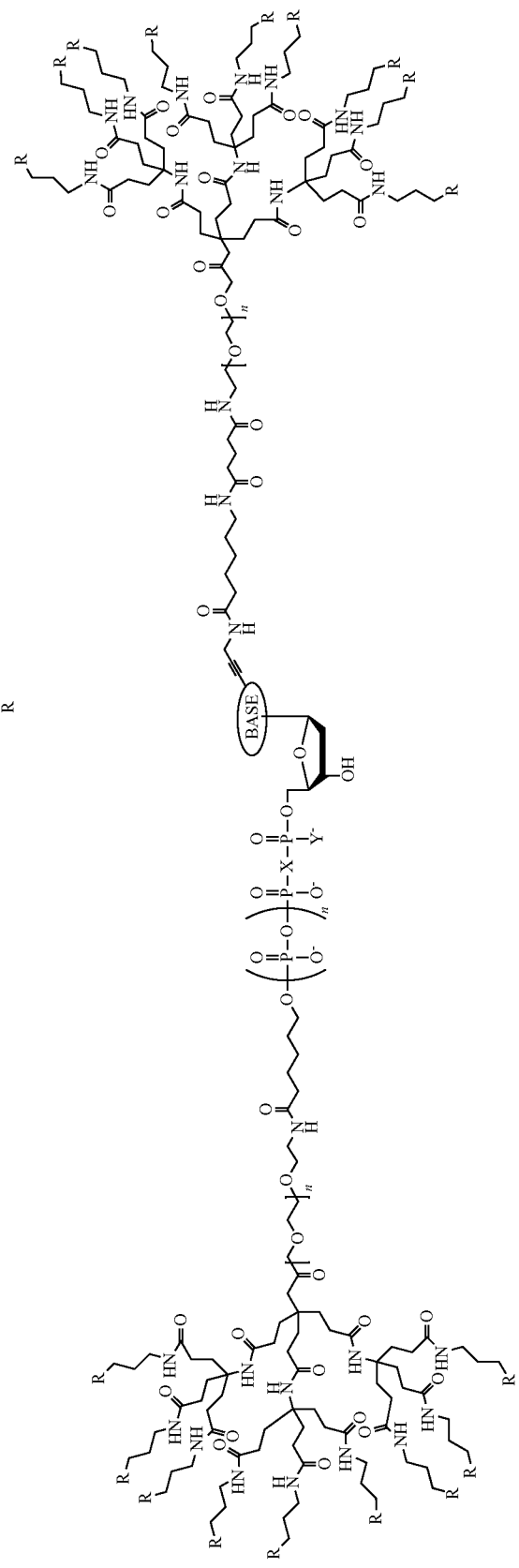

wherein n=1, 2, 3, 4, 5, or 6 and wherein R is a Raman active group.

12. The compound of claim 1, wherein the Raman cluster tag(s) comprises one or more Raman active groups.

13. The compound of claim 1, wherein the Raman active groups are selected from the following: —N=N$^+$=N$^-$, —C≡CH, —C≡CD, —C≡C-alkyl, —C≡C-aryl and —C≡N moieties.

14. The compound of claim 1, wherein the Raman cluster tag and/or tags has a Raman spectroscopy peak with a wave number from 2100 cm$^{-1}$ to 2300 cm$^{-1}$.

15. The compound of claim 1, wherein a Raman cluster tag is attached to the 2' position of the sugar.

16. The compound of claim 1, wherein the cleavable linker is either chemically cleavable or photo cleavable.

17. The compound of claim 16, wherein the cleavable linker comprises any one of an allyl, alkyl, carbonyl, Sieber linkers, indole, disulfide, dithiomethyl, azidomethyl, or nitrobenzyl.

18. The compound of claim 16, wherein the cleavable linker is cleavable with one or more of Pd(0), tetrabutylammonium, DTT, a triphosphine, peroxydisulphate, or iodine.

19. A compound having the structure:

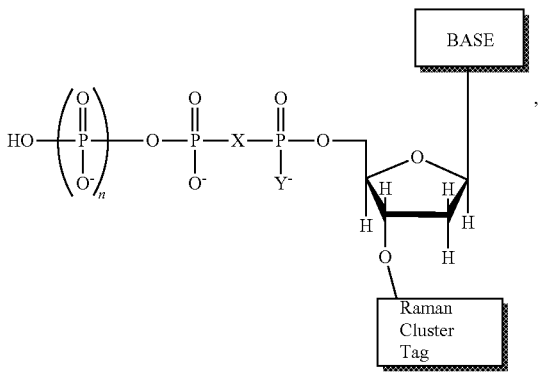

wherein base is any one of A, G, T, C, or U, wherein n=0, 1, 2, 3, 4, 5, or 6, wherein X is any one of CH$_2$, NH, CHF—, or CF$_2$, wherein Y is any one of O, S, or BH$_3$, and wherein the Raman Cluster Tag comprises Raman active groups, and optionally the Raman cluster tag comprises a cleavable linker wherein cleaving the linker results in a 3'-OH.

* * * * *